US011193161B2

(12) United States Patent
Kim et al.

(10) Patent No.: US 11,193,161 B2
(45) Date of Patent: Dec. 7, 2021

(54) METHOD FOR DETECTING TARGET NUCLEIC ACID SEQUENCE USING CLEAVED COMPLEMENTARY TAG FRAGMENT AND A COMPOSITION THEREFOR

(71) Applicant: GENEMATRIX, INC., Seongnam-si (KR)

(72) Inventors: Soo Ok Kim, Seoul (KR); Suk Joon Kim, Seongnam-si (KR); Sun Pyo Hong, Seoul (KR); Hyun Jae Chung, Gunpo-si (KR); Woo Jae Cho, Anyang-si (KR); Jae Il Kim, Seoul (KR); Seung Min Yang, Gwangju-si (KR); Ae Ri Cho, Seongnam-si (KR); Seong Soo Hong, Seoul (KR); Jeong Woo Kim, Yongin-si (KR); Sun Young Jeong, Hwaseong-si (KR)

(73) Assignee: GENEMATRIX INC., Seongnam-si (KR)

( * ) Notice: Subject to any disclaimer, the term of this patent is extended or adjusted under 35 U.S.C. 154(b) by 176 days.

(21) Appl. No.: 16/095,695

(22) PCT Filed: Apr. 21, 2017

(86) PCT No.: PCT/KR2017/004297
§ 371 (c)(1),
(2) Date: Oct. 23, 2018

(87) PCT Pub. No.: WO2017/188669
PCT Pub. Date: Nov. 2, 2017

(65) Prior Publication Data
US 2019/0177768 A1 Jun. 13, 2019

(30) Foreign Application Priority Data
Apr. 25, 2016 (KR) .................. 10-2016-0050313

(51) Int. Cl.
*C12Q 1/683* (2018.01)
*C12Q 1/6806* (2018.01)
*C12Q 1/686* (2018.01)
*C12Q 1/6816* (2018.01)
*C12Q 1/70* (2006.01)
*C12Q 1/6853* (2018.01)
*C12Q 1/6872* (2018.01)

(52) U.S. Cl.
CPC ........... *C12Q 1/683* (2013.01); *C12Q 1/6806* (2013.01); *C12Q 1/686* (2013.01); *C12Q 1/6816* (2013.01); *C12Q 1/6853* (2013.01); *C12Q 1/6872* (2013.01); *C12Q 1/705* (2013.01); *C12Q 1/708* (2013.01); *C12Y 207/07007* (2013.01)

(58) Field of Classification Search
CPC ........................... C12Q 1/6853; C12Q 1/6806
See application file for complete search history.

(56) References Cited

U.S. PATENT DOCUMENTS

| 8,383,348 B2 * | 2/2013 | Willis ................... C12Q 1/686 435/6.12 |
| 2016/0194695 A1 * | 7/2016 | An ....................... C12Q 1/6858 506/26 |

FOREIGN PATENT DOCUMENTS

| CN | 103534358 | 1/2014 |
| CN | 105229170 | 1/2016 |
| JP | 2006-508632 | 3/2006 |
| JP | 2006-508677 | 3/2006 |
| KR | 10-1999-0021950 | 3/1999 |
| KR | 10-2005-0028904 | 3/2005 |
| KR | 10-2010-0018327 | 2/2010 |
| KR | 10-2011-0048734 | 5/2011 |
| KR | 10-1503726 B1 | 3/2015 |
| KR | 10-2015-0088772 | 8/2015 |
| KR | 10-1569479 B1 | 11/2015 |
| KR | 10-2015-013916 A | 12/2015 |
| WO | WO03/074723 A2 | 9/2003 |
| WO | WO2004/053159 A2 | 6/2004 |
| WO | WO-2014163225 A1 * | 10/2014 ........... C12Q 1/6858 |

OTHER PUBLICATIONS

Stovall, In Vitro Selection Using Modified or Unnatural Nucleotides, Curr Protoc Nucleic Acid Chem, 56:9.6.1-9.6.33, 2014. (Year: 2014).*

(Continued)

*Primary Examiner* — Samuel C Woolwine
*Assistant Examiner* — Carolyn L Greene

(57) ABSTRACT

The present invention relates to a method and a composition for detecting a target nucleic acid sequence using a cleaved complementary tag fragment. Specifically, the present invention relates to a method for linking a complementary tag sequence to a PCR primer so that a tagging can be produced by a restriction enzyme during a PCR reaction, diversifying the complementary tag sequence to be linked to each primer by utilizing factors such as length and nucleic acid combination, etc., and distinguishing the target sequence using the same.

According to the present invention, a cleaved complementary tag fragment (CCTF) under stringent conditions is a complementary sequence to any sequence at the 5' end linked to the primer and cannot be formed unless a PCR reaction and a restriction enzyme reaction occur, and the cleaved single strand is formed only when hybridization to the target sequence occurs and a primer extension product complementary to the target sequence is formed, so as to have a higher degree of accuracy secured by reading the cleaved single strand. In addition, the CCTF can be used to identify a plurality of target nucleic acid sequences by selecting various analytical techniques and analysis equipment according to a user's intention. For example, a result can be confirmed rapidly and accurately in genetic testing, identification of organisms in a sample, diagnosis of microbial or viral infection, etc.

1 Claim, 8 Drawing Sheets

Specification includes a Sequence Listing.

(56) References Cited

OTHER PUBLICATIONS

Office Action for China Patent Application No. 201780025886.7, dated Jun. 2, 2021.

* cited by examiner

[Fig. 1]
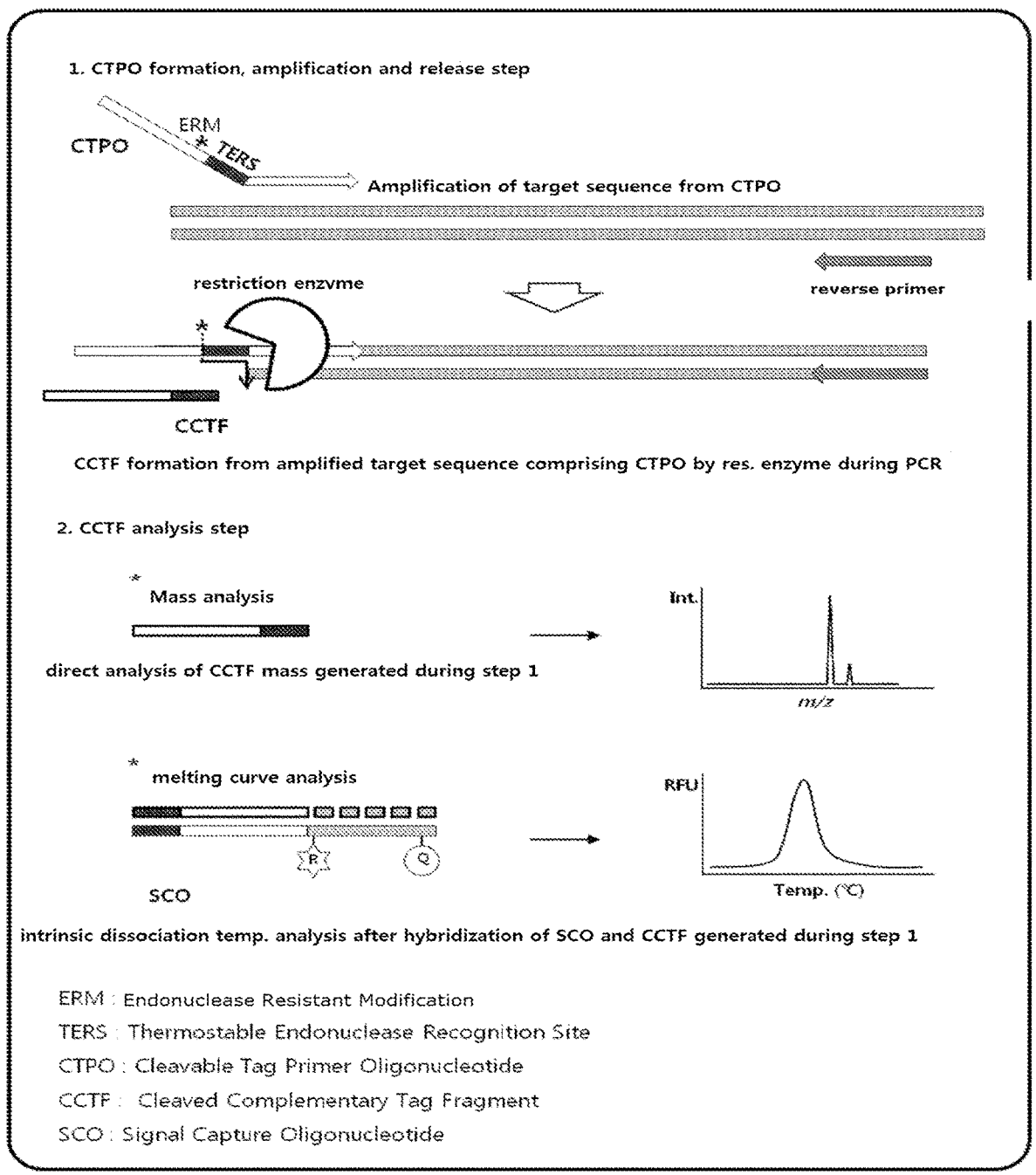

[Fig. 2]
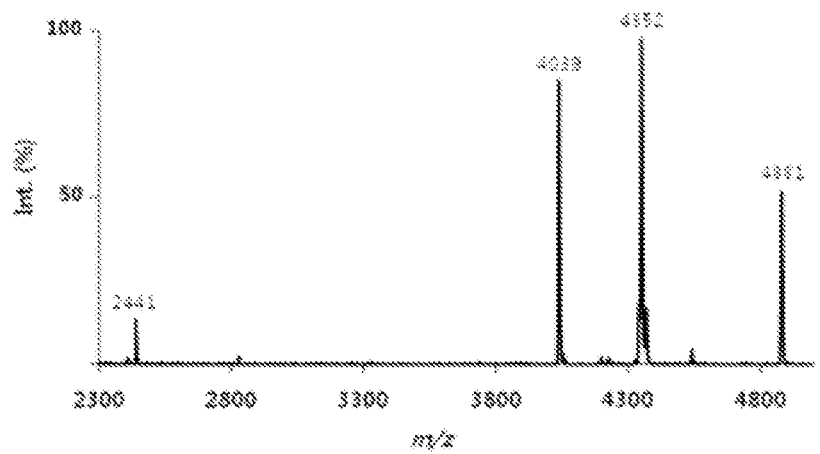

[Fig. 3]
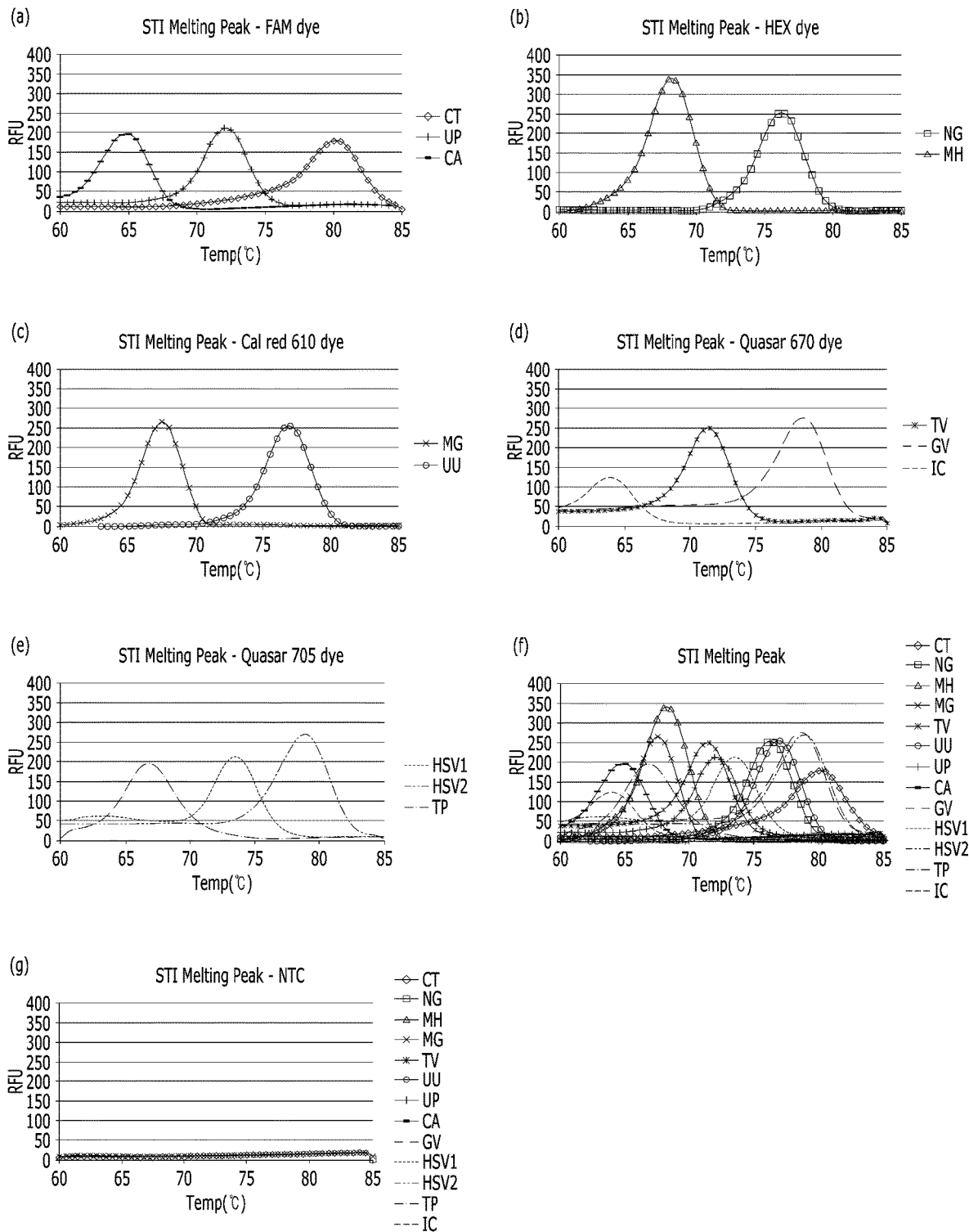

[Fig. 4]
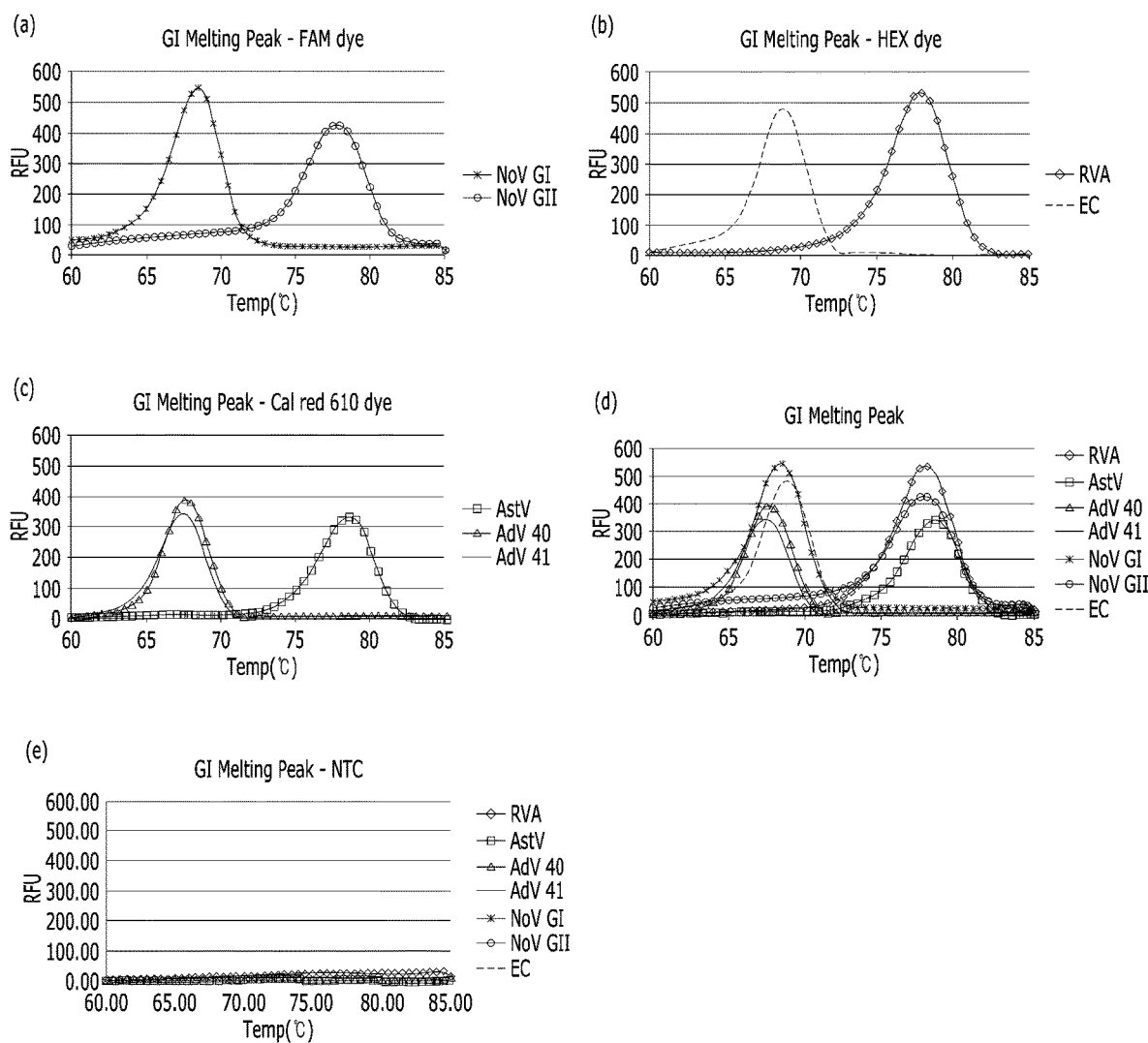

[Fig. 5]
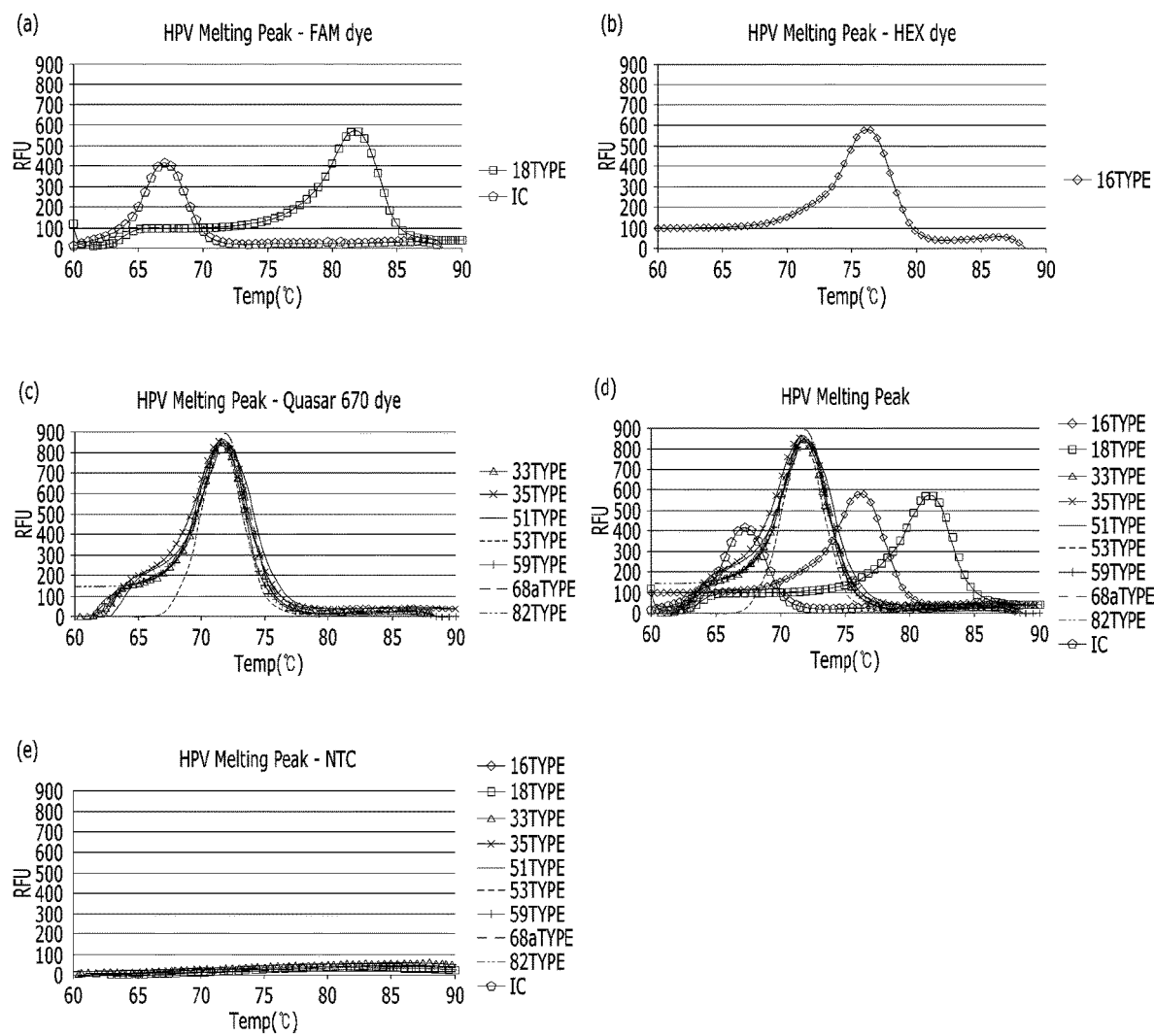

[Fig. 6]
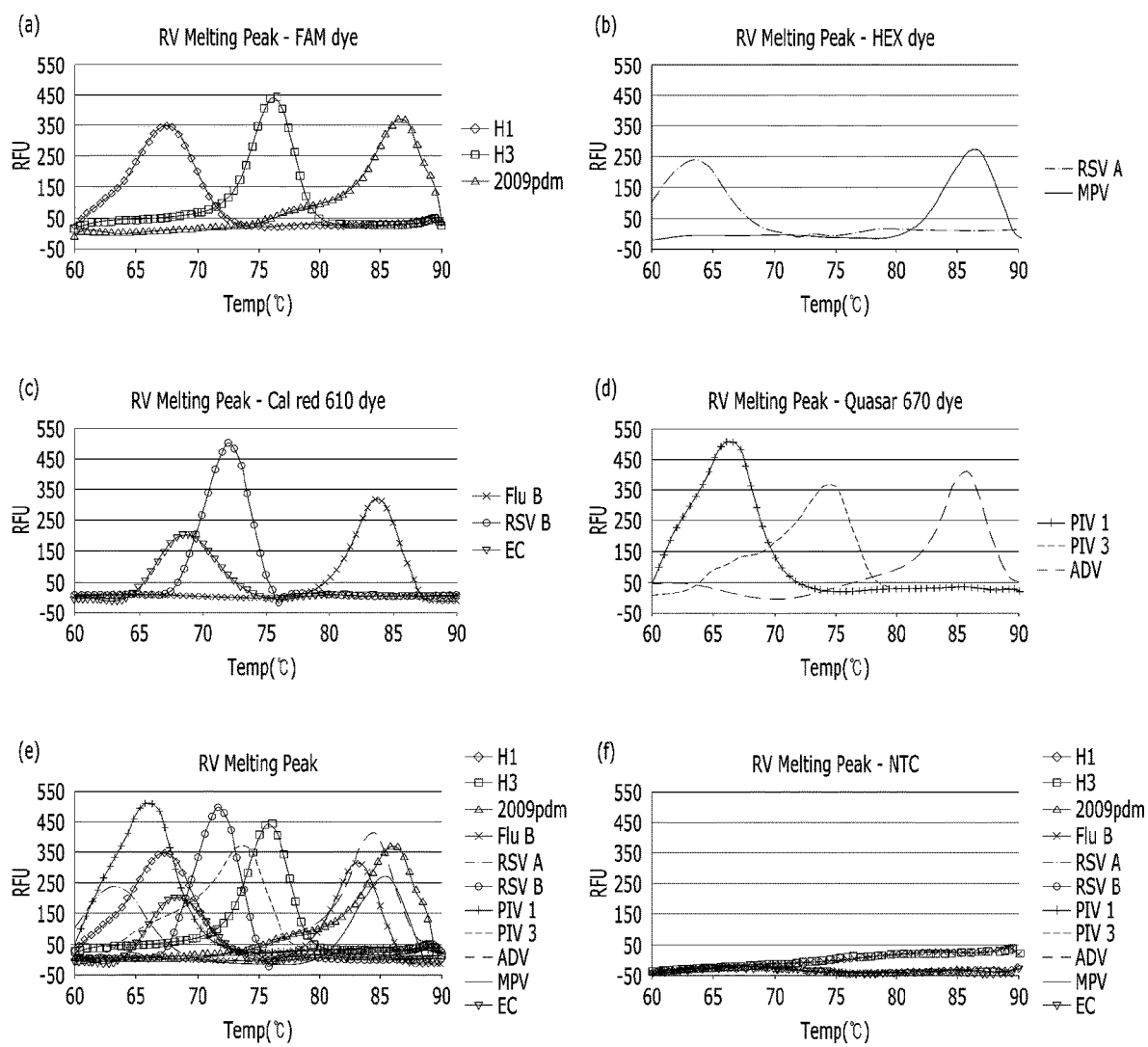

[Fig. 7]
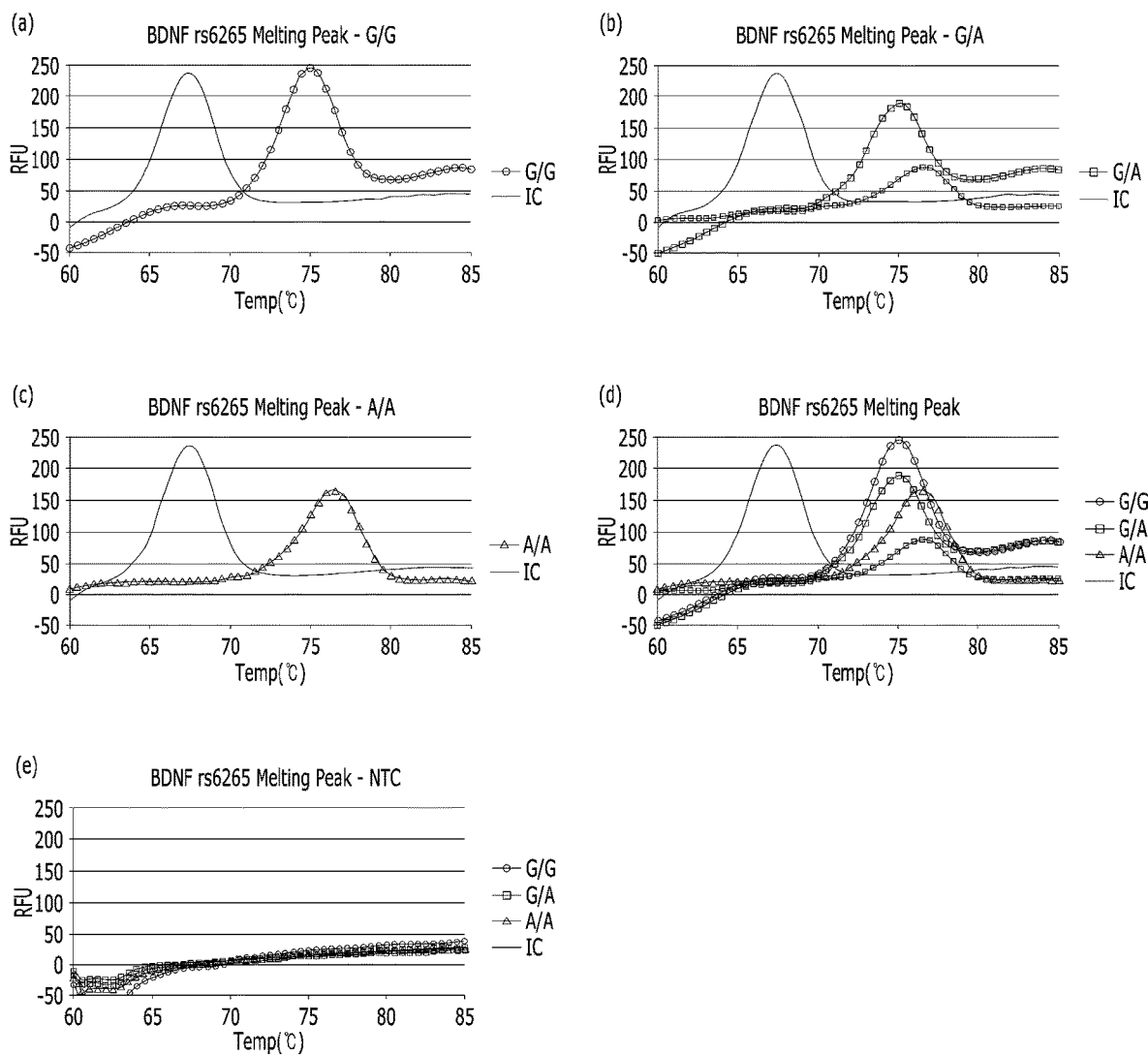

[Fig. 8]
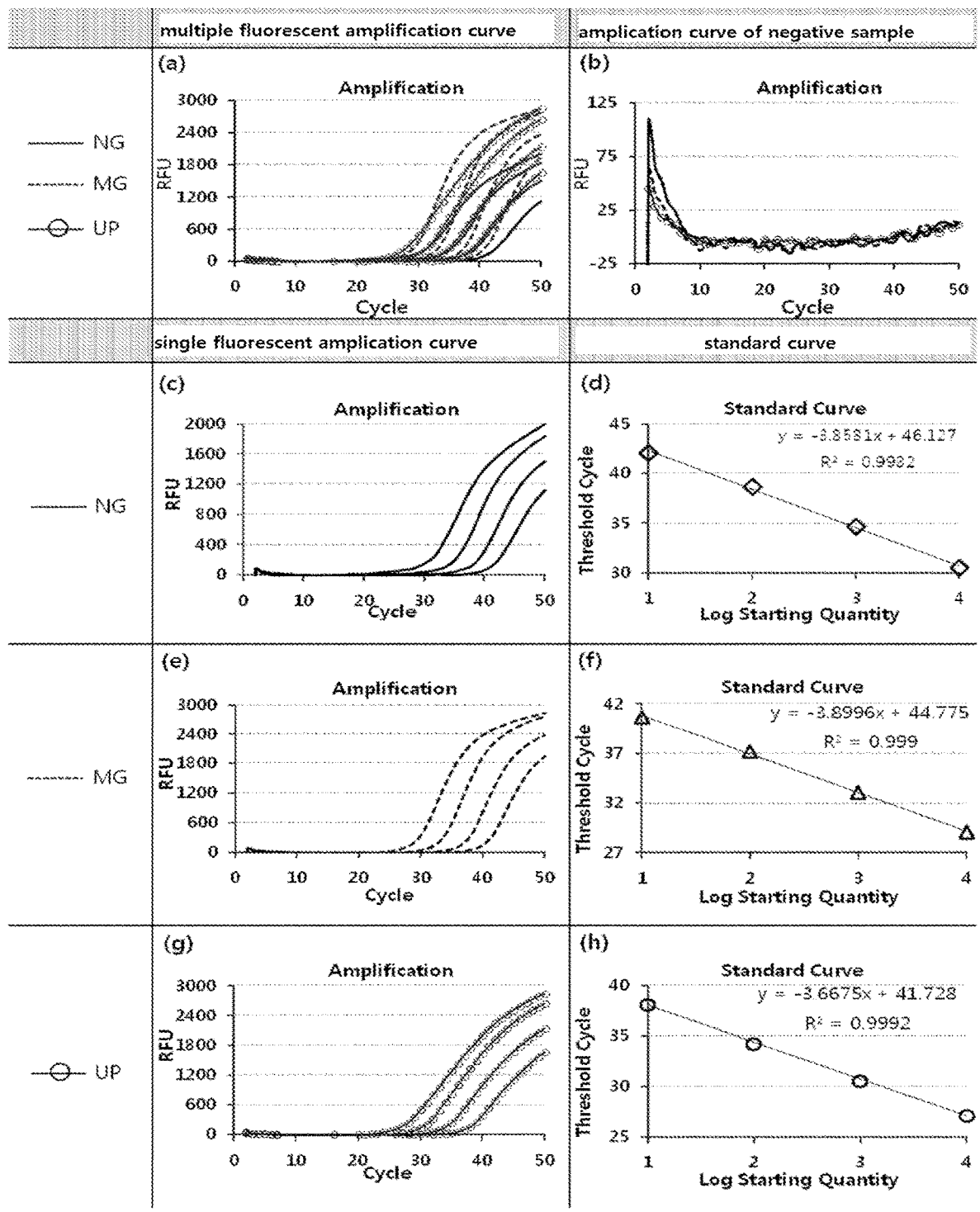

METHOD FOR DETECTING TARGET NUCLEIC ACID SEQUENCE USING CLEAVED COMPLEMENTARY TAG FRAGMENT AND A COMPOSITION THEREFOR

TECHNICAL FIELD

The present invention relates to a method for detecting target nucleic acid sequence using cleaved complementary Tag fragment and a composition therefor, and specifically relates to a method of identifying the amplified product by ligating a template of tag capable of producing a marked substance to a primer that specifically reacts with the target sequence, thereby synthesizing and releasing the tag by restriction enzyme activity in the PCR reaction and introducing it into the reaction solution. Also, the present invention relates to a method for generating and identifying a tag characterized in that the tag generated during a reaction using only one kind of template sequence of a tag for one target sequence is analyzed in various analyzing apparatuses to identify the tag, and a composition used in the method.

BACKGROUND ART

Polymerase Chain Reaction (PCR) is one of techniques very usefully utilized in detecting and analyzing low concentration nucleic acids. The detection of the nucleic acid is based on the complementarity of the double strand oligonucleotide sequences and the extension reaction of each DNA polymerase, and the target nucleic acid sequence can be detected using this (Barry et al., Current Opinion in Biotechnology, 12; 21, 2001).

Multiple PCR is a method that can simultaneously amplify nucleic acids of multiple target sequences, and is relatively fast and simple compared to other methods, and thus plays a very large role in diagnosis field such as genetic test, identification of organisms in samples, and microbial or viral infection, etc.

The most common method for confirming the results of such multiplex PCR is to design primers by varying an amplification product size of the target sequence as desired in PCR, and to analyze the size of the amplified product by electrophoresis of the PCR result, and then to confirm as to whether amplification of the target sequence is made. In this case, the number of genes that can be amplified at one time is limited to 3 to 4 experimentally because there is a restriction that the size of the amplification product should be limited within a narrow range, due to that the efficiency of amplification depends on the size of the amplification product that can be generated during the PCR reaction and thus a uniform amplification efficiency cannot be guaranteed. In this case, it also occurs the case that the size of the desired gene amplification product may overlap. Therefore, there is a limit to the interpretation of the detection method when the multiple PCR is analyzed depending on the size.

Real-time PCR guarantees a confirmation of a rapid PCR result in confirming the PCR results, and it can identify as to whether the amplification is made by marking fluorescent material regardless of the size of the amplified product. The methods performing and detecting Real-time PCR can be divided into intercalating method and probe method, wherein the intercalating method is referred to a method of confirming fluorescence intensity by inserting fluorescent substance between double-stranded base sequences. Since this method cannot distinguish the amplification products forming the double strands, and can observe all of them as the fluorescence of the same wavelength. Therefore, it has a limit on identifying the amplification product by each target sequence to detect and identify at least one amplified product simultaneously. The probe method is a method of detecting the amplified product by reading the fluorescence value of the probe designated for each target sequence and, in the case of using this method, since the amplification product can be detected only in the number of analyzable fluorescence channels of a device to be used, the multiple analysis over the number of fluorescent channels is not suitable for this.

Therefore, studies were continuously carried out to insert the tag during PCR to enable the maximum number of multiple analysis.

In the case of Luminex's xTAG technology, a constant base sequence comprised of a random array of thymine (T), adenine (A), and guanine (G), which constitutes the nucleic acid, was set and named xTAG. It is a method comprising inserting xTAG sequence into the primer to be located the xTAG sequence at the end in the amplification of the target sequence to be observed, so that the xTAG was inserted into the amplification product during the PCR procedure, and secondarily joining the xTAG with a bead to which the complementary sequence to xTAG attached to form a complementary bond between the two base sequences, detecting the target using the same, and analyzing the target sequence with fluorescence of the bead. In this method, even though the xTAG does not participate in the amplification, if the primer is not completely removed after the amplification, it has problems that there is a possibility that it binds to the complementary xTAG of the bead to recognize the mark, and an error occurs that the complementary sequence of xTAG forms non-specific reaction by PCR and thus non-specific target is detected (U.S. Pat. Nos. 7,645,868 and 8,624,014).

In order to solve this problem, studies have been continuously performed that a tag is constructed during the PCR reaction, the tag does not affect the PCR reaction, the maximum numbers of multiple detections are possible.

DISCLOSURE

Technical Problem

The present invention is derived to solve the above problems and to meet the above needs and the object of the present invention is to provide a method for solving the uncertainty which can be occurred when the results are determined depending on the length of the generated product in amplifying and analyzing a target sequence using an amplification reaction such as PCR, and for solving the restriction to the maximum numbers of amplification that can be identified in multiple detection.

The another object of the present invention to provide a method for improving accuracy by solving errors due to non-specific amplification which can be caused by the use of artificial sequence as a tag itself in identifying a target sequence amplification by forming the tag.

Technical Solution

In order to accomplish the above object, the present invention provides a primer with the structure comprising a target sequence and a non-complementary random nucleic acid sequence and sequentially comprising a restriction enzyme recognition sequence and a nucleic acid sequence complementary to the target sequence.

In one embodiment of the present invention, the restriction enzyme recognition sequence is preferably one selected from the group consisting of Pho I, PspGI, BstNI, TfiI, ApeKI, TspMI, BstBI, BstEII, BstNI, BstUI, BssKI, BstYI, TaqI, MwoI, TseI, Tsp45I, Tsp509I, TspRI, Tth111, Nb.BsmI, Nb.BsrDI, Nt.BspQI, Nt.BstNBI restriction enzymes and Nick restriction enzymes, but is not limited thereto.

In another embodiment of the present invention, the said primer is preferably one that a modified dNTP inserted at the cleavage site of the restriction enzyme recognition sequence of the primer, for the purpose of that a cleaved by-product other than the cleaved complementary tag fragment allow not to participate in the reaction, and the modified dNTP to be inserted into the cleavage site is phosphorothioated dNTP, dNTP containing 7-deazapurine, or a 2'-O-methyl nucleotide (2'-OmeN) in a DNA template, but is not limited thereto.

In another embodiment of the present invention, it is preferable, but not limited, that the primer is from 5 mers or more to 50 mers or less in length of the cleaved complementary tag fragment as generated.

In one embodiment of the present invention, the primer is one or more one selected from the group consisting of SEQ ID NOS: 1, 3, 9, 11, 13, 15, 17, 19, 21, 23, 25, 27, 29, 31, 33, 74, 76, 78, 80, 82, 86, 115, 117, 119, 121, 123, 125, 127, 129, 131, 151, 153, 155, 156, 159, 161, 164, 166, 168, 170, 204, 205, 207, 218, 220 and 222, but is not limited thereto.

Furthermore, the present invention provides a method for forming a tag to be used in classifying and analyzing the kinds of the target sequences amplified in the Polymerase Chain Reaction, and identifying it, comprising:

a) hybridizing a target sequence with a primer of the present invention comprising a template of a tag for generating the tag that is a cleaved complementary tag fragment, b) generating the complementary tag fragment cleaved from the primer by the activity of a restriction enzyme when the amplification procedure is proceeded by the hybridization of a) and introducing it into a reaction solution, and c) identifying the generated cleaved complementary tag fragment through an analyzer to confirm the presence of the target sequence.

In one embodiment of the present invention, it is preferable to analyze the mass of the cleaved complementary tag fragment to identify the cleaved complementary tag fragment in the above method, and the instrument used for the mass spectrometry is preferably a matrix-assisted laser desorption-ionization-time-of-flight mass spectrometer ((MALDI-TOF MS), a Liquid Chromatography Mass Spectrometer, or a High Performance Liquid Chromatography Mass Spectrometer, but is not limited thereto.

In another embodiment of the present invention, the mass per unit electric charge (m/z) of the cleaved tag fragment to be used for mass spectrometry is preferably from greater than 0 to 10000 Da or less, but is not limited thereto.

In another embodiment of the present invention, in order to preserve the mass of a cleaved complementary tag fragment to be used in mass analysis during the amplification process, it is preferable to use DNA polymerase that the function of adenine-addition elongation effect (A tailing) at the 3'end, which is an intrinsic property of the nucleic acid polymerase, is inhibited, but is not limited thereto.

In another embodiment of the present invention, it is preferable to analyze the fluorescence signal using the oligonucleotide that is tagged by fluorescence and Quencher and has the complementary sequence of the cleaved complementary tag fragment as the identification method of the cleaved complementary tag fragment, but it is not limited thereto.

In another embodiment of the invention, it is preferable to analyze the dissociation temperature and melting peak by varying the inherent dissociation temperature at which the double strand of the oligonucleotide and the cleaved complementary tag fragment are dissociated into a single strand, and to identify the presence of the target sequence by identifying the cleaved complementary tag fragment in the method, but is not limited thereto.

In yet another embodiment of the present invention, the oligonucleotide is preferably 5 or more in length, but is not limited thereto.

In another embodiment of the present invention, it is preferable to attach a quencher to the nucleotide at the 3'end of the oligonucleotide in order to prevent elongation of the base sequence from the oligonucleotide in the method, but is not limited thereto.

In another embodiment of the present invention, it is preferable to identify the complementary tag fragment cleaved by analyzing the cycle threshold (Ct) value of the fluorescence signal of the oligonucleotide, but not limited thereto.

In a preferred embodiment of the present invention, it is preferable to identify causative organisms of a sexually transmitted disease in the said method, and the sexually transmitted disease causative organism is preferable one selected from the group consisting of *Chlamydia trachomatis, Neisseria, Gonorrhea, Mycoplasma hominis, Mycoplasma genitalium, Trichomonas vaginalis, Ureaplasma urealyticum, Ureaplasma parvum, Candida albicans, Gardnerella vaginalis*, Herpes simplex virus 1, Herpes simplex virus 2, *Treponema pallidum*, but is not limited thereto.

The present invention also provides a composition for diagnosing sexually-transmitted diseases, comprising the primer of the present invention as an effective component.

In another embodiment of the present invention, it is preferable to identify the causative organism of gastrointestinal tract disease, wherein the causative organism of gastrointestinal tract disease is selected from the group consisting of Rotavirus A, Astrovirus, Adenovirus F40, Adenovirus F41, Norovirus GI and Norovirus GII, but is not limited thereto.

The present invention also provides a composition for diagnosing a gastrointestinal disease agent comprising the primer of the present invention as an effective component.

In another preferred embodiment of the present invention, it is preferable to identify a human papilloma virus in the method, and the subpopulations of the human papilloma virus is preferably selected from the group consisting of types 16, 18, 33, 35, 51, 53, 59, 68a, and 82, but is not limited thereto.

The present invention also provides a composition for diagnosing HPV comprising the primer of the present invention as an effective component.

In another preferred embodiment of the present invention, it is preferable to identify a causative organism of the respiratory disease in the method, and the causative organism of the respiratory disease is one being selected from the group consisting of Influenza A/H1N1, Influenza A/H3N2, Influenza A/HIN/2009pdm, Influenza B, Parainfluenza 1, Parainfluenza 3, Respiratory syncytial virus A, Respiratory syncytial virus B, Human metapneumovirus, Adenovirus, but is not limited thereto The present invention also provides a composition for the diagnosis of respiratory diseases, comprising the primer of the present invention as an effective component.

In another preferred embodiment of the present invention, the method is preferably a single nucleotide polymorphism (SNP), wherein the single base mutation is preferably one selected from the group consisting of r6265 of the Brain-derived neurotrophic factor gene (BDNF gene), but is not limited thereto.

The present invention also provides a composition for analyzing the BDNF gene rs6265 gene comprising the primer of the present invention as an effective component.

Hereinafter, the present invention will be described.

The present inventors have tried our best to develop the method that can perform a multiplex amplification reaction on a large number of targets at one time by clearly distinguishing each amplification product through an easier, faster and more efficient method in preforming the amplification reaction and can analyze the results.

As a result, so as to be able to generate a nucleic acid sequence which can be used as a tag in an amplification reaction, when a sequence serving as a template for a tag was inserted into a primer, and only tag was cleaved by a restriction enzyme, we confirmed that the generated tag can play a role as the tag for detecting the target sequence and also identified that it can identify the amplification efficiently and rapidly than other existing methods in the multiplex amplification reaction analysis by applying it to various analysis methods, and thus, has been completed the present invention.

The present invention relates to a method of forming tags to be used for sorting and analyzing kinds of amplified target sequences during a PCR reaction.

In particular, the present invention is characterized in comprising the steps of: (1) hybridizing a target sequence with a primer comprising a template of a tag for generating the tag, (2) generating the tag from the template of the tag using a restriction enzyme during the PCR reaction, and (3) analyzing the generated tag with various analysis equipment to identify the tag.

(1) As the step for hybridizing a target sequence with a primer (CTPO-Cleavable Tag Primer Oligonucleotide, hereinafter referred to as CTPO) comprising a template of a tag for generating the tag (CCTF-Cleaved Complementary Tag Fragment, hereinafter referred to as CCTF); wherein CTPO comprises a sequence non-complementary to the target sequence (the template of CCTF), followed by a restriction enzyme recognition sequence and a nucleic acid sequence complementary to the target sequence, and the nucleic acid sequence site complementary to the target sequence located at the 3'end hybridizes with the target sequence, thereby playing a role as a primer during the PCR reaction, (2) as a step for generating and releasing CCTF from CTPO by the activity of a restriction enzyme in the amplification process; wherein the restriction enzyme recognition sequence is inserted into the amplified product elongated from the above-described CTPO, and CCTF is generated by the activity of the thermostable restriction enzyme recognizing it and introduced into the reaction solution.

(3) as the step for analyzing and identifying the generated CCTF through various analysis equipment to confirm existence of a target nucleic acid sequence; wherein the mass of the generated CCTF is measured to identify the type of CCTF, and the amplified product is sorted to confirm the presence of the target nucleic acid sequence, or the fluorescence is emitted during the procedure that the oligonucleotide composed of the sequence complementary to the generated CCTF and tagged with the fluorescence and the quencher (Signal Capture Oligonucleotide—SCO, hereinafter referred to as SCO) and CCTF are hybridized to form a double strand and dissociate again into a single strand, and such inherent dissociation temperature is analyzed to identify the type of CCTF, and to identify whether the amplification of the target nucleic acid sequence is occurred or not.

Hereinafter, the present invention will be described in detail.

In step (1), prior to hybridizing the CTPO and the target sequence, the structure of CTPO is divided into a template portion of the CCTF, a restriction enzyme recognition sequence, and a sequence complementary to the target as shown in the following Formula 1.

$$5'\text{-A-B-}3'$$ Formula I

The A site in the structural formula 1 is comprised of a random sequence to be a template of the CCTF, and the complementary sequence of the CCTF template, that is, the CCTF site, is elongated by amplifying it after annealing with the target sequence and then the CCTF site is released by the restriction enzyme during the amplification. The released CCTF is characterized by being a random sequence having 5 or more oligonucleotides in length so that it can be specifically analyzed as a tag. Random sequences can be used in any sequence that does not create a by-product during the PCR reaction. The nucleotide sequence to be used as a template for CCTF is free from any sequence that does not cause a hybridization reaction during the amplification reaction.

B is a restriction enzyme recognition sequence, which means a specific recognition sequence of restriction enzymes and Nick restriction enzymes having thermal stability that can be used during amplification. For example, it includes Pho I, PspGI, BstNI, TfiI, ApeKI, TspMI, BstBI, BstEII, BstNI, BstUI, BssKI, BstYI, TaqI, MwoI, TseI, Tsp45I, Tsp509I, TspRI, Tth111I. Nb.BsmI, Nb.BsrDI, Nt.BspQI, Nt.BstNBI, etc.

Most preferably, among them, PspGI can be used, and the restriction enzyme used in Example of the present invention is PspGI.

The modified dNTP is inserted into a site cleaved by the restriction enzyme in the restriction enzyme recognition sequence of CTPO so as not to exist and participate the cleaved by-products other than CCTF in the reaction. Examples thereof include phosphorothioated dNTPs, dNTPs containing 7-deazapurine, or 2'-O-methyl nucleotides (2'-OMeN) in DNA templates, etc. The prior art, PNAS 89 (1992) 392-396 and Nucleic Acids Research 20 (1) 1991 55-61 can be applied to the present invention. Most preferably, a phosphothiolated bond is inserted into the cleavage site among the recognition sequence to prevent the cleavage of the template of CCTF by a restriction enzyme, thereby securing a template capable of generating CCTF and to prevent a by-product which can be generated by releasing the template of CCTF into the reaction solution, thereby increasing the efficiency of the reaction. It represents the effects of the invention different from the prior art, SDA (Strand Displacement Amplification) method (US Pat. No. 92,819,358) in view of that it generates CCTF and prevents the template to inflow to the reaction solution.

The C site shown in the structural formula 1 means a part after the restriction enzyme recognition sequence up to the 3'end, and is composed of a target specific sequence so that it binds specifically to the target during amplification so as to maintain its role as a primer.

In step (2), when the amplification product is formed by CTPO, and the amplified product present in the double strand is cleaved to CCTF by the restriction enzyme and released into the reaction solution, the appropriate concentration of the restriction enzyme to be used can be varied depending on the purpose of use. In addition, the results are different depending on the type of polymerase to be used, which can be also varied depending on the purpose of use. For example, when CCTF is formed for the purpose of mass spectrometry, it is preferable that the weight of CCTF should be kept constant regardless of the amplification process and should not reflect the intrinsic property of the nucleic acid polymerase. Therefore, a nucleic acid polymerase having no adenine addition extension effect (A tailing) at the 3'end, which is an intrinsic property of the nucleic acid polymerase, should be selected and used. Among the nucleic acid polymerase enzymes that do not make A tailing, Phusion polymerase, Vent polymerase, Deep Vent polymerase, Bst polymerase, etc. are present.

However, when CCTF analysis method using other techniques than mass analysis is applied, there is no variation in the results due to the A tailing effect, and thus, any polymerase can be used.

In order to increase the efficiency of the restriction enzyme to generate CCTF and to maximize the effect by promoting the influx into the reaction solution, a restriction enzyme reaction time can be further added during the PCR process. Reaction time, reaction temperature, etc. can be applied differently depending on the kind of the specific restriction enzyme and the reaction intention.

In step (3), as the step that the generated CCTF is analyzed through various analysis equipment to identify the target nucleic acid sequence, when the mass of the generated CCTF is directly analyzed, the kinds of CCF are diversified through recombination of length and sequence, Mass spectrometry such as MALDI-TOF MS, LC MS and HPLC MS can be used to observe the intrinsic mass of the generated CCTF, and the amplified target sequence can be identified and identified using the said mass. It is preferable to observe it through MALDI-TOF MS, the range of mass of CCTF which is easy to observe is 1200 Da or more. The amplification products can be observed by forming various CCFs in the mass range as above.

The amplified target sequence can be identified by observing the fluorescence signal of CCTF, and this is the method which comprises hybridizing CCTF with SCO which is tagged with the fluorescence and the quencher so that the generated CCTF can provide the fluorescence signal at the inherent dissociation temperature, and is the sequence complementary to the CCTF having the inherent dissociation temperature, analyzing the fluorescence signal at the inherent dissociation temperature, and confirming the generation of CCTF, thereby identifying the presence of the target nucleic acid sequence.

For the release of CCTF, as described above, the use concentration of the restriction enzyme is designated according to the purpose of use, and the kind of the polymerase is not related to the A tailing unlike the mass analysis. The CCTF released from the amplification product and introduced into the reaction solution reacts with the SCO present in the reaction solution, wherein the component of the SCO is as follows.

The complementary sequence of CCTF exists to enable hybridization with CCTF from the 5'end to the 3' end and the sequence of SCO is determined by CCTF length, sequence recombination depending on CCTF. In order to diversify the kinds of tags in step (1), the combination of the length and the sequence may be designed differently to give the inherent dissociation temperature of CCTF and SCO, such as in the case using the method such the length of CCTF and the method of sequence recombination, etc. In this case, the SCO is composed of a complementary sequence of CCTF, and the fluorescent substance is contained in the sequence, and the position of the fluorescent substance is possible in anywhere at least a certain length apart from the quencher. At the 3'end of the SCO, a blocker is positioned so that SCO serves as a primer during the reaction to prevent the nucleotide sequence from elongation. Spacer C3, Phosphat, ddC, Inverted END and Quencher, etc. may be used as the blocker, but not limited thereto. In particular, when the quencher is located at the 3'end of SCO, the SCO is served as a primer during the reaction to prevent the nucleotide sequence from elongation, and simultaneously hybridizes with CCTF to suppress the emission of the fluorescent material by the FRET phenomenon, before it forms a double strand with CCTF. By using a quencher in combination with a substance preventing nucleotide sequence elongation, an unnecessary modification reaction can be shortened in the production of SCO, thereby increasing the yield of the production reaction and further reducing the manufacturing cost. By using the hybridization of CCTF generated during the reaction with SCO contained in the reaction, it can be identified as to whether CCTF is generated by identifying the dissociation of the double strand with the fluorescence and analyzing it to confirm whether CCTF is generated due to the target sequence, and then the target sequence can be identified. The range of temperature that can be defined by the inherent dissociation temperature of the SCO is ~95° C., and if there is no interference of the dissociation temperature of each double strand, there is no limitation in defining the inherent dissociation temperature for each fluorescent substance.

The combination of SCO's fluorophore and quencher can be exemplified as Alexa Fluor 350, Alexa Fluor 405, Alexa Fluor 430, Alexa Fluor 488, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, Alexa Fluor 790, ATTO 390, ATTO 425, ATTO 465, ATTO 488, ATTO 495, ATTO 514, ATTO 520, ATTO 532, ATTO Rho6G, ATTO 540Q, ATTO 550, ATTO 565, ATTO Rho3B, ATTO Rho11, ATTO Rho12, ATTO Thio12, ATTO 580Q, ATTO Rho101, ATTO 590, ATTO Rho13, ATTO 594, ATTO 610, ATTO 612Q, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740, ATTO MB2, AMCA, AMCA-S, BODIPY FL, BODIPY R6G, BODIPY 530/550, BODIPY TMR, BODIPY 558/568, BODIPY 564/570, BODIPY 576/589, BODIPY 581/591, BODIPY TR, BODIPY 630/650, BODIPY 650/665, Biosearch Blue, CAL Fluor Gold 540, CAL Fluor Orange 560, CAL Fluor Red 590, CAL Fluor Red 610, CAL Fluor Red 635, Pulsar 650, Quasar 570, Quasar 670, Quasar 705. FAM, Fluorescein, Fluorescein-C3, Calcein, Carboxyrhodamine 60, Carboxy-X-rhodamine (ROX), Cascade Blue, Cascade Yellow, Cy2, Cy3, Cy5, Cy3.5, Cy5.5, Cy7, Dansyl, Dapoxyl, Dialkylaminocoumarin, 4',5'-Dichloro-2',7'-dimethoxy-fluorescein, DM-NERF, Eosin, Erythrosin, HEX, Hydroxycoumarin, IRD40, IRD 700, IRD 800, JOE, Lissamine rhodamine B, LC Red 610, LC Red 640, Marina Blue, Methoxycoumarin, Naphthofluorescein, NED, Oregon Green 488, Oregon Green 500, Oregon Green 514, Pacific Blue, PyMPO, Pyrene, Phycoerythrin, Rhodamine 6G, Rhodamine Green, Rhodamine Red, Rhodol Green, 2',4',5',7'-Tetra-bromosulfonefluorescein, Tetramethyl-rhodamine (TMR), Carboxytetramethylrhodamine (TAMRA), Texas Red, Texas Red-X. TET, VIC, Yakima Yellow, BMN-Q460, DDQ-1, Dabcyl, BMN-Q530, BMN-Q535, Eclipse, Iowa Black FQ, BHQ-1, TQ2, IQ4, QSY-7, BHQ-2, TQ3, DDQ-II, BBQ-650, Iowa Black RQ, QSY-21, BHQ-3, etc., and may also include any fluorescent material and quencher.

In addition, the reaction between SCO and CCTF occurs simultaneously with the amplification reaction and the CCTF formation reaction, and in this case, by utilizing the fact that the double strand formation ratio of SCO represents a similar efficiency to the amplification amount of the target sequence, the Ct graph of the SCO having the inherent dissociation temperature can be made, and by using this, it is possible to identify the target sequence in a different manner from the inherent dissociation temperature analysis method.

The above content made by the solving means of the present invention will be described in more detail as the most preferable embodiment through the Examples of the present invention.

Advantageous Effects

In the method of the present invention, since an arbitrary tag (CCTF) is generated and cleaved by restriction enzymes during the amplification reaction, the double strand of the restriction enzyme recognition sequence is not formed before the amplification reaction of the artificial sequence (CTPO) added to form the tag and thus, there is no possibility that it is randomly cleaved; since the tags are generated only by the reaction products specifically generated to the target sequence during PCR, the method of the present invention has the high accuracy for forming CCTF, and can obtain more delicate analysis results than the existing PCR result analysis depending on the length of the PCR amplification product or the specificity of the specific sequence; and the method of the present invention can distinguish and interpret amplification products specifically even if various kinds of amplification products are produced in the same length. In addition, since the analysis of the resultant CCTF can be applied to most of the analysis using base sequence, the device for interpretation can be selected and applied ordinarily. In particular, the method of the present invention can be used in the fields of diagnosis, etc., which require rapid multiple analysis using an amplification reaction.

DESCRIPTION OF DRAWINGS

FIG. 1 is a representative diagram illustrating the formation process of CTPO and CCTF used in a PCR reaction, and an example for the analysis of CCTF, as a schematic diagram of CCTF formation.

FIG. 2 shows the results of the formation of CCTF and MALDI analysis in dual target PCR. CTPO was designed to form different CCTFs for each target sequence, amplified, and analyzed by MALDI, and as a results, a peak corresponding to the masses of CCTF 1 obtained by amplifying *Neisseria gonorrhoeae* (NG) and cleaving it and CCTF2 obtained by amplifying *Mycoplasma hominis* (MH) and cleaving it, were observed.

FIG. 3 shows the results of Real-time PCR Melting Peak analysis for causative organisms of sexually transmitted diseases. As the results representing the multiple target dissociation temperature measurements to each target of *Chlamydia trachomatis*(CT), *Neisseri gonorrhea* (NG) *Mycoplasma hominis*(MH), *Mycoplasma genitalium*(MG), *Trichomonas vaginalis*(TV), *Ureaplasma urealyticum*(UU), *Ureaplasma parvum*(UP), *Candida albicans*(CA), *Gardnerella vaginalis*(GV), Herpes simplex virus 1(HSV 1), Herpes simplex virus 2(HSV 2), *Treponema pallidum*(TP) and Internal Control (IC), the peak was observed at the inherent dissociation temperature that each SCO has (CT: FAM 80° C., NG: HEX 76.5° C., MH: HEX 68° C., MG: CalRed610 67.5° C., TV: Quasar670 71.5° C., UU: CalRed610 77° C., UP: FAM 77° C., CA: FAM 65° C., GV: Quasar670 78.5° C., HSV 1: Quasar705 73.5° C., HSV 2: Quasar705 79° C., TP: Quasar705 66° C., IC: Quasar670 63.5° C.) (a)(b)(c)(d)(e)(f), and no peak of SCO that visualized CCTF was observed when the target sequence was not added in the same composition (g).

FIG. 4 shows the results of Real-time PCR Melting Peak analysis for the causative organism of the gastrointestinal diseases. As the results representing the multiple inherent dissociation temperature measurements to each target of Rotavirus A(RVA), Astrovirus(AstV), Adenovirus F40(AdV 40), Adenovirus F41(AdV 41). Norovirus GI(NoV GI), Norovirus GII(NoV GII) and External Control, the peak was observed at the inherent dissociation temperature that each SCO has (RVA: HEX 78° C., AstV: CalRed610 78° C., AdV 40: CalRed610 67° C., AdV 41: CalRed610 67° C., NoV GI: FAM 68° C., NoV Gil: FAM 84° C., EC: HEX 69° C.) (a)(b)(c)(d), and no peak of SCO that visualizes CCTF was observed when the target sequence was not added in the same composition (e).

FIG. 5 shows the results of Real-time PCR Melting Peak analysis for Human Papilloma Virus (HPV) detection. As a result of multiple inherent dissociation temperature measurements of each target of type 16, type 18, type 33, type 35, type 51, type 53, type 59, type 68a, type 82 and IC, the peak was observed at the inherent dissociation temperature that each SCO has (type 16: HEX 76.5° C., type 18: FAM 78° C., type 33: Quasar670 71° C., type 35: Quasar670 710° C., type 51: Quasar670 71° C. type 53: Quasar670 710° C., type 59: Quasar670 71° C., type 68a: Quasar670 71° C., type 82: Quasar670 71° C., IC: Quasar670 67.5° C.) (a)(b)(c)(d), and no peak of SCO that visualizes CCTF was observed when the target sequence was not added in the same composition (e).

FIG. 6 shows the result of Real-time PCR Melting Peak analysis for detection of respiratory disease-induced virus. As a result of multiple inherent dissociation temperature measurements of each target of Influenza A/H1N1(H1), Influenza A/H3N2(H3), Influenza A/H1N1/2009pdm (2009pdm), Influenza B(Flu B), Parainfluenza 1(PIV 1), Parainfluenza 3(PIV 3), Respiratory syncytial virus A(RSV A), Respiratory syncytial virus B(RSV B), Human metapneumovirus(MPV), Adenovirus(AdV), External control (EC), the peak was observed at the inherent dissociation temperature that each SCO has (H1: FAM 67.5° C., H3: FAM 76.5° C., 2009pdm: FAM 86.5° C., Flu B: CalRed610 83.5° C., PIV 1: Quasar670 66° C., PIV 3: Quasar670 74° C., RSV A: HEX 63.5° C., RSV B: CalRed610 72° C., MPV: HEX 86° C., ADV: Quasar670 85° C., EC: CalRed610 68.5° C.) (a)(b)(c)(d)(e), and no peak of SCO that visualizes CCTF was observed when the target sequence was not added in the same composition (f).

FIG. 7 shows the results of Real-time PCR Melting Peak analysis to analyze the genotpe of rs6265, a single nucleotide polymorphism of BDNF gene. As a result representing the multiple inherent dissociation temperature measurements of each target of mutant A/A, wild type G/G and heterozygote A/G, the peak was observed at the inherent dissociation temperature that each SCO has (A/A: 76.5° C., A/G: 76.5° C. ≠ 75° C., G/G 75° C., IC: 66° C.) (a)(b)(c)(d), and no peak of SCO that visualizes CCTF was observed when the target sequence was not added in the same composition (e).

FIG. 8 shows the results of real-time PCR Ct graph. As a result, representing fluorescent amplification curves and standard curves of SCO under the experimental condition of a multi-real-time polymerization chain reaction experiment of *Neisseria. gonorrhea* (NG), *Mycoplasma. hominis* (MH), *Ureaplasma. parvum* (UP) in which genomic DNA of each of the above causative organism was diluted by 10-folds from 100 pg/ul concentration, (a) graph shows the results of fluorescence amplification curves plotted when three target sequences are present at each concentration simultaneously, (b) graph shows a negative result plotted when all three target sequences are not included. When the standard curve is represented by a single fluorescence amplification curve of the graph corresponding NG of (a) graphs, it can be represented as (c) and (d), and the graph corresponding to MG graph can be represented as (e) and (f), and the curve corresponding to UP can be represented as (g) and (h).

MODE FOR INVENTION

Hereinafter, the present invention will be described in detail with reference to Examples. These examples are for illustrative purposes only and thus, are not interpreted to limit the scope of the present invention.

Example 1. Formation of CCTF and MALDI Analysis in Dual Target PCR

This experiment was conducted to prove that the CCTF formed during the PCR reaction for the detection of multiple target sequences can be detected in a target-specific manner by analyzing the mass using MALDI-TOF MS. In Example 1, the causative organism of sexually transmitted diseases, DNAs of *Neisseria. gonorrhoeae* (NG) and *Mycoplasma. Hominis* (MH) were used as the targets.

1. Target Template DNA and Primers Manufactured by Sequence Specific Manner

The forward primers of NG and MH targeting in this example were manufactured based on the method described in the Detailed Description of the Invention as CTPO. The 5'end of the forward primer was an arbitrary nucleotide sequence consisting of a sequence non-complementary to the DNA of NG and MH so that it could be used as a template of CCTF, and a restriction enzyme recognition sequence was consecutively located thereon. The sequence after the restriction enzyme recognition sequence up to the 3'end is composed of a sequence complementary to the target region of the DNA of NG and MH, and plays a role as a primer. In addition, the 5'end of forward primer is composed of a different number of nucleotides with each other and has a different mass value for each CCTF generated, in order to design that the amplification products can be distinguished from each other as the mass when CCTF is formed. The reverse primer is consisted of a sequence complementary to the target site of the DNA of NG and MH.

Primer information and target sequence information being amplified and generated are as follows.

```
Primer 1:
                                        (SEQ ID. NO: 1)
5'-TGAACTAT * CCTGG
TCCGACGTTTCGGTTGTGTTGAAACACCGCCCGG-3'
```

```
Primer 2:
                                        (SEQ ID. NO: 2)
5'-GCTCCTTATTCGGTTTGACCGG-3'
```

```
Primer 3:
                                        (SEQ ID. NO: 3)
5'-ATCTATGATA* CCTGG
TTTAGCTCCTATTGCCAACGTATTGG-3'
```

```
Primer 4:
                                        (SEQ ID. NO: 4)
5'-TGTGTGGAGCATCTTGTAATCTTTGGTC-3'
```

Amplified product 1: GenBank: CP012028.1/Position (start-end): 251416-251506

```
                                        (SEQ ID. NO: 5)
5' TGAACTAT * CCTGGTCCGACGTTTCGGTTGTGTTGAAACACCGC
CCGGAACCCGATATAATCCGCCCTTCAACATCAGTGAAAATCTTTTTTT
TAACCGGTCAAACCGAATAAGGAGC-3'
```

Amplified product 2: GenBank: AJ243692.1/Position (start-end): 835-944

```
                                        (SEQ ID. NO: 6)
5' ATCTATGATA* CCTGGTTTAGCTCCTATTGCCAACGTATTGGAA
AAAAACTTTGGTATTGAAAAAGGATTTATGACAACAGTCCACTCATAT
ACAGCAGACCAAAGATTACAAGATGCTCCACACA-3'
```

The bold and slanted font of the Primer sequence means the restriction enzyme recognition sequence, and the underline is the complementary sequence of the CCTF produced thereby. In the examples of the present invention, the part represented by * is a tag that modified dCTP was inserted into C in the recognition sequence to block the site cleaved by the PspGI restriction enzyme.

The sequence and mass of the CCTF produced in the amplified product are as follows.

```
CCTF 1:
                                        (SEQ ID. NO: 7)
5'-CCAGGATAGTTCA-3'/4038.6 Da

CCTF 2:
                                        (SEQ ID. NO: 8)
5'-CCAGGTATCATAGAT-3'/4351.8 Da
```

2. PCR Amplification

Primer 1 and Primer 3 as forward primers, and Primer 2 and Primer 4 as reverse primers were subjected and PCR reaction was performed simultaneously, and then, the formation of CCTF was determined.

20 μl Of the total reaction solution comprising each Primer 3 μM, PspGI (NEB, USA) 2U, PCR buffer (1×), MgSO$_4$ 3 mM, dNTP 400 μM, Vent Polymerase (NEB, USA) 1 U and NG, MH template DNA 100 pg/ul was subjected to PCR reaction using C1000 PCR (Bio-Rad, USA) under the following conditions:

94° C. 10 mins,
94° C. 30 secs, 62° C. 30 secs 72° C. 30 secs (35 cycles),
85° C. 2.5 hours 3. Purification and Desalting of the Cleaved Fragments During the PCR Reaction Oasis (Waters) C18 reverse phase column chromatography was used to isolate the DNA fragments cleaved by treatment with a restriction enzyme during the PCR reaction from the above solution. To the solution treated with the restriction enzyme, 70 µl of 0.15 M triethylammonium acetate (TEAA, pH 7.6) was added and allowed to stand for 1 minute. Resin was activated by passing 1 ml of 100% acetonitrile (ACN; Sigma. USA) and 0.1 M TEAA to the column, and then, 100 µl of a mixed solution of the solution treated with the restriction enzyme and 0.15M TEAA, 2 ml of 0.1M TEAA and 1 ml of the third distilled water were passed through in this order. The column was placed on a Collection Plate and 100 µl of 70% ACN was passed. When the eluate was collected on the collection plate, the collection plate was dried at 120° C. for 60 minutes.

4. MALDI-TOF MS Analysis

4 µl of MALDI matrix [22.8 mg ammonium citrate, 148.5 mg hydroxypicolinic acid, 1.12 ml acetonitrile, 7.8 ml $H_2O$] was previously dotting on Anchor chip plate of MALDI-TOF mass spectrometry (Biflex IV, Bruker), and then, was dried at 37° C. for 30 minutes. 10 µl of the third distilled water was dissolved in a sample of the collection plate after the purification and desalting procedure, and 2 µl of the solution was dropped onto the dried MALDI Matrix, the Maldin Matrix was dried again at 37° C. for 30 minutes, and then was analyzed by MALDI-TOF mass spectrometry. The analysis method follows the manual of the MALDI-TOF mass spectrometry.

The result of analyzing the CCTF produced by the above reaction using a mass spectrometer is as shown in FIG. 2. From the result of FIG. 2, it can be confirmed the peaks of 4083 Da, the mass of CCTF 1 which can be formed when performing PCT with the combination of Primer 1 and Primer 2, and 4351 Da. the mass of CCTF 2 which can be formed when performing PCT with the combination of Primer 3 and Primer 4 (a). These results demonstrated that the PCR amplification product can be analyzed using CCTF formed by CTPO, and that CCTF can be used to accurately amplify and differentiate the target sequence in the reaction product comprising various primers.

Therefore, it was demonstrated that the target nucleic acid sequence can be detected more precisely than the conventional PCR method by performing the PCR using the CCTF marking technique and distinguishing the tag fragments of various lengths through mass analysis using MALDI-TOF MS after performing PCR.

Example 2. Formation of CCTF and Analysis of Inherent Dissociation Temperature Peak of CCTF in Multiple Target PCR The CCTF generated during the PCR reaction is combined with the SCO capable of generating a fluorescence signal at the inherent dissociation temperature to form an intrinsic dissociation temperature peak, which can be observed directly after the PCR process using a real-time PCR instrument. During the PCR reaction, CCTF is formed, and at the same time it is hybridized with the CCTF complementary sequence region of SCO to form a double strand. By measuring the inherent dissociation temperature of SCO seen when the double strand is dissociated into a single strand, the kinds of CCTF can be discriminated and analyzed simultaneously with PCR through a real-time PCR instrument. The SCO used in this example used different fluorescent reporters, respectively, and the inherent dissociation temperature was adjusted to enable discrimination of CCTF.

In this example, CCTF analysis was performed using a real-time PCR instrument using 12 kinds of the causative organisms of the sexually transmitted diseases, 5 types of the causative organisms of gastrointestinal diseases, 9 types of HPV subtypes, 10 types of the causative organisms of the respiratory disease and single base mutation rs6265 nucleic acid of BDNF gene, respectively.

1. Formation of CCTF in multi-target PCR of the causative organisms of the sexually transmitted diseases and analysis of the inherent dissociation temperature peak of CCTF CCTF analysis for Chlamydia trachomatis(CT), Neisseria. gonorrhea (NG) Mycoplasma hominis(MH), Mycoplasma genitalium(MG), Trichomonas vaginalis(TV), Ureaplasma urealyticum(UU), Ureaplasma parvum(UP), Candida albicans(CA), Gardnerella vaginalis(GV), Herpes simplex virus 1(HSV 1), Herpes simplex virus 2(HSV 2), Treponema pallidum(TP), the causatives agents of sexually transmitted diseases and Internal control (IC) DNA was performed using Real-time PCR instrumentation.

1) Primer for Target Sequence Template DNA Constructed by the Sequence-Specific Manner The forward primer used in this example was CTPO and was constructed on the same principle as in Example 1 above. The 5'end of CTPO was composed of 19-20 mers of nucleotide sequences, and was composed of a sequence non-complementary to DNA of the target sequence to form CCTF. The restriction enzyme recognition sequence was then located, and from this up to the 3' end, it was composed of the sequence complementary to each target site was composed to play a role as a primer. The reverse primer was composed of sequence complementary to the target site to be amplified.

In addition, SCO, which forms a complementary bond with CCTF to be a double-stranded template, was positioned by positioning fluorescent offsetting molecules (BHQ-1 or BHQ-2), and the fluorescent reporter molecular was positioned so as to have a certain distance.

Primer information and target sequence information which is amplified and generated are as follows

```
Primer 5:
                                      (SEQ ID. NO: 9)
5'-CCACTCCAGCCGGCTGACA*CCAGGACTTGGTGTGACGCTATC

AGCAT-3'

Primer 6:
                                     (SEQ ID. NO: 10)
5'-GTTTTCAAAACACGGTCGAAAACAAAGTC-3'

Primer 7:
                                     (SEQ ID. NO: 11)
5'-CATCGCCACGAGCCGGTTAA*CCAGGTTGAAACACCGCCCGGA

ACCC-3'

Primer 8:
                                     (SEQ ID. NO: 12)
5'-GCTCCTTATTCGGTTTGACCGGT-3'

Primer 9:
                                     (SEQ ID. NO: 13)
5'-ACTCACGCTAATGGAGCGCA*CCAGGTTTAGCTCCTATTGCCA

ACGTATTGG-3'

Primer 10:
                                     (SEQ ID. NO: 14)
5'-TGTGTGGAGCATCTTGTAATCTTTGGTC-3'

Primer 11:
                                     (SEQ ID. NO: 15)
5'-GCTACCCAGCCGGCTACAAG*CCAGGCTTTTATGGTGCTTATA

TTGGTGGCATG-3'
```

-continued

Primer 12:
(SEQ ID. NO: 16)
5'-CTGTATAACGTTGTGCAGCAGGTC-3'

Primer 13:
(SEQ ID. NO: 17)
TGCCGCGTGATTCGATCCCA*CCAGGTATGTCCGGCACAACATGCGCT-3'

Primer 14:
(SEQ ID. NO: 18)
5'-GAGCTTACGAAGGTCGGAGTTGA-3'

Primer 15:
(SEQ ID. NO: 19)
5'-TCTCATAGCTGGGCCGCTG*CCAGGAAGTAGCATATGATGAAGCACACAACA-3'

Primer 16:
(SEQ ID. NO: 20)
5'-TAATGCAACGTGCATTTGCTTCAAC-3'

Primer 17:
(SEQ ID. NO: 21)
5'-CAGATCGTTGGCACTCTGCGA*CCAGGTTAAAGTAGCATATGATCAAGCTCATTCA-3'

Primer 18:
(SEQ ID. NO: 22)
5'-TTGTAATGATACAACGAGCATCATCATTAAT-3'

Primer 19:
(SEQ ID. NO: 23)
5'-GCTCGTATGCCGCTCCATATA*CCAGGCCAAATCTGGATCTTCCTCTGCATC-3'

Primer 20:
(SEQ ID. NO: 24)
5'-GAGCTTGAGCTGGACCCAGAG-3'

Primer 21:
(SEQ ID. NO: 25)
5'-ACGTGCCGTGCATCGTTGCA*CCAGGCAACCGGCTCCATTTTGGTGGAG-3'

Primer 22:
(SEQ ID. NO: 26)
5'-CGTCACGTCCTTCATCGGTCC-3

Primer 23:
(SEQ ID. NO: 27)
5'-TCGCAGTCCCGTCGAGGAA*CCAGGAGGCCTGGCTATCCGGAGAAAC-3'

Primer 24:
(SEQ ID. NO: 28)
5'-CGTTGTGTTGGCCGCAGGTC-3'

Primer 25:
(SEQ ID. NO: 29)
5'-CTCATAGCTAGGCGCCTG*CCAGGGCTGCACGTGGGTCTGTTGTG-3'

Primer 26:
(SEQ ID. NO: 30)
5'-GGAAACGCAGGCCACGAAACC-3'

Primer 27:
(SEQ ID. NO: 31)
5'-GCTTCGCGTCTCAGGCCTGT*CCAGGGGGCATTACAGTTTTGCGTCATGAC-3'

Primer 28:
(SEQ ID. NO: 32)
5'-CAAGTCTGAGCACTTGCACCG-3'

Primer 29:
(SEQ ID. NO: 33)
5'-CTGTTAGCTCTGCGAGCT*CCAGGGGAGCGACACTTGTTGGTGTTGAC-3'

Primer 30:
(SEQ ID. NO: 34)
5'-TGATGAAATGAAGCCACCCGTGC-3'

SCO 1:
(SEQ ID. NO: 35)
TCGGAGCCAGCGCGGCGTAAAC[T(FAM)]CCACTCCAGCCGGCTGACA[BHQI]

SCO 2:
(SEQ ID. NO: 36)
TACAACAGCAGTACGGAGACGAC[T(HEX)]CATCGCCACGAGCCGGTTAA[BHQI]

SCO 3:
(SEQ ID. NO: 37)
ATTTATTCTTACTCGATGTTAAA[T(HEX)]ACTCACGCTAATGGAGCGCA[BHQI]

SCO 4:
(SEQ ID. NO: 38)
TATATATATATATTATTATAAA[T(CalRed610)]GCTACCCAGCCGGCTACAAG[BHQ2]

SCO 5:
(SEQ ID. NO: 39)
AAGAATAACTACTACAATCTACT[T(Quasar670)]TGCCGCGTGATTCGATCCCA[BHQ2]

SCO 6:
(SEQ ID. NO: 40)
TTATTATTATTATTATTATATA[T(CalRed610)]TCTCATAGCTGGCCGCTG[BHQ2]

SCO 7:
(SEQ ID. NO: 41)
AATCTTCAATGCTTACCGTA[T(FAM)]CAGATCGTTGGCACTCTGCGA[BHQ1]

SCO 8:
(SEQ ID. NO: 42)
AAAATAAATAATATAATATA[T(FAM)]GCTCGTATGCCGCTCCATATA[BHQ1]

SCO 9:
(SEQ ID. NO: 43)
TCGGAGCCAGCGCGGCGTAACG[T(Quasar670)]ACGTGCCGTGCATCGTTGCA[BHQ2]

SCO 10:
(SEQ ID. NO: 44)
AAGAATAACTACTACAATCTAC[T(Quasar705)]TTCGCAGTCCCGTCGAGGAA[BHQ2]

SCO 11:
(SEQ ID. NO: 45)
TCGGAGCCAGCGCGGCGTAA[T(Quasar705)]CTCTCATAGCTAGGCGCCTG[BHQ2]

SCO 12:
(SEQ ID. NO: 46)
AAAATAAATAATATAATATAG[T(Quasar705)]CTTCGCGTCTCA

GGCCTGT[BHQ2]

SCO 13:
(SEQ ID. NO: 47)
AAAATAAATAATATAATATA[T(Quasar670)]TCTGTTAGCTCTG

CGAGCT[BHQ2]

Amplified product 3: GenBank: X52557.1/Position (start-end): 157-227

(SEQ ID. NO: 48)
CCACTCCAGCCGGCTGACA*CCAGG*ACTTGGTGTGACGCTATCAGCAT

GCGTATGGGTTACTATGGTGACTTTGTTTTCGACCGTGTTTTGAAAAC

Amplified product 4: GenBank: X52364.1/Position (start-end): 375-459

(SEQ ID. NO: 49)
CGCCCACCGCATCCCGCGCCCCTCCCTCAGCA*CCAGG*TTGAAACACCG

CCCGGAACCCGATATAATCCGCCCTTCAACATCAGTGAAAATCTTTTTT

TAACCGGTCAAACCGAATAAGGAGC

Amplified product 5: GenBank: AJ243692.1/Position (start-end): 835-944

(SEQ ID. NO: 50)
ACTCACGCTAATGGAGCGCA*CCAGG*TTTAGCTCCTATTGCCAACGTA

TTGGAAAAAAACTTTGGTATTGAAAAAGGATTTATGACAACAGTCCACT

CATATACAGCAGACCAAAGATTACAAGATGCTCCACACA

Amplified product 6: GenBank: U09251.1/Position (start-end): 3462-3687

(SEQ ID. NO: 51)
GCTACCCAGCCGGCTACAAG*CCAGG*CTTTATGGTGCTTATATTGGTGG

CATGCACCATGATCGTCCTTTTAAAAAGTCTGCGAGGATTGTTGGTGAT

GTAATGAGTAAATTCCACCCTCATGGTGATATGGCAATATATGACACCA

TGTCAAGAATGGCTCAAGACTTTTCATTAAGATACCTTTTAATTGATGG

TCATGGTAATTTTGGTTCTATAGATGGTGATAGACCTGCTGCACAACGT

TATACAG

Amplified product 7: GenBank: XM_001582993.1/Position (start-end): 705-768

(SEQ ID. NO: 52)
TGCCGCGTGATTCGATCCCA*CCAGG*TATGTCCGGCACAACATGCGCTT

ATGTCCGGCACAACATGCGCTCTCCGCTTCCCAGGTCAGCTCAACTCCG

ACCTTCGTAAGCTC

Amplified product 8: GenBank: AF085700.2/Position (start-end): 4673-4873

(SEQ ID. NO: 53)
TCTCATAGCTGGGCCGCTG*CCAGG*AAGTAGCATATGATGAAGCACACA

ACAAAATGGCGCATACTGTGTATTTCACTAATTTCTATCGTTCATCAAAA

CCACTATTTTTAGATGAAGAAGACCCAATTAATCCCTGTTTTCAAACTAT

TAGTATGGGTGGGGGTTATGTATCTGGTGAAGTGTATCGTTCTGATTTTG

AAGTTGAAGCAAATGCACGTTGCATTA

Amplified product 9: GenBank: AF085733.2/Position (start-end): 4677-4886

(SEQ ID. NO: 54)
CAGATCGTTGGCACTCTGCGA*CCAGG*TTAAAGTAGCATATGATCAAGC

TCATTCAAAAATGGCACATACTGTCTATTTTACGAATTTTTATCGTTCA

TCTAAACCTTTATTTTTAGATGAAGAAGATCCAATCAACCCCTGTTTTC

AAACAATTAGTATGGGTGGTGGATATGTTTCAGGTGAAATTTATCGTTC

TGATTTTGAAATTAATGATGATGCTCGTTGTATCATTACAA

Amplified product 10: GenBank: M90812.1/Position (start-end): 1736-1811

(SEQ ID. NO: 55)
GCTCGTATGCCGCTCCATATA*CCAGG*CCAAATCTGGATCTTCCTCTG

CATCTGCTTCTGGATCATCAAGCAGCAGCACCAGCTCTGGGTCCAGCTCA

AGCTC

Amplified product 11: GenBank: L08167.1/Position (start-end): 273-434

(SEQ ID. NO: 56)
ACGTGCCGTGCATCGTTGCA*CCAGG*CAACCGGCTCCATTTTGGTGGA

GTCGCTTGATCGTTTTGTGATCGTTTAGTGTGATGATTATTATGTCTAG

AGAGTTAAGCGATAGGCTTTTACTGGTGTATCACTGTAAGGGCGTATTGG

TTGGATGCCTTGGTAGACAGGACCGATGAAGGACGTGACG

Amplified product 12: DQ889502.1/Position (start-end): 123860-124007

(SEQ ID. NO: 57)
TCGCAGTCCCGTCGAGGAA*CCAGG*AGGCCTGGCTATCCGGAGAAACA

GCACACGACTTGGCGTTCTGTGTGTCGCGATGTCTCTGCGCGCAGTCTG

GCATCTGGGCTTTTGGGAAGCCTCGTGGGGGCTGTTCTTGCCGCCACC

CATCGGGGACCTGCGGCCAACACAACG

Amplified product 13: GenBank: EU018100.1/Position (start-end): 561-746

(SEQ ID. NO: 58)
CTCATAGCTAGGCGCCTG*CCAGG*GCTGCACGTGGGTCTGTTGTGGGT

AGAGGTGGGCGGGAGGGCCCCGGCCCCACCGCCCCCCCACAGGCGGC

GCGTGCGGAGGGCGGCCCGTGCGTCCCCCCGGTCCCCGCGGGCCGCCCG

TGGCGCTTCGGTGCCCCCGGTATGGTATTCCGCCCCCAACCCCGGGTTT

CGTGGCCTGCGTTTCC

Amplified product 14: GenBank: U57757.1/Position (start-end): 910-1067

(SEQ ID. NO: 59)
GCTTCGCGTCTCAGGCCTGT*CCAGGGGCATTACAGTTTTGCGTCATG

ACGGCTTTGAAGCTGACGACCTCATTGCAACCCTAGCAAAACGAGTTGC

GGCTGAGCACTGTCATGTTGTGATTATCTCCTCAGATAAAGATGTACTT

CAGCTTGTGTGTGATACGGTGCAAGTGCTCAGACTTG

Amplified product 15: GenBank: NM_001035551.2/Position (start-end): 214-369

(SEQ ID. NO: 60)
CTGTTAGCTCTGCGAGCT*CCAGGGGAGCGACACTTGTTGGTGTTGAC

AAGTTCGGTAACAAATACTACCAGAAGCTAGGCGATACTCAATACGGTAT

GCACAGATGGGTAGAGTATGCTTCAAAGGATCGTTACAACGCATCTCAA

GTACCAGCTGAATGGCACGGGTGGCTTCATTTCATCA

The bold and slanted font of the Primer sequences means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. The sequence of the CCTF produced from the amplified product is as follows.

CCTF 3:
(SEQ ID. NO: 61)
5'-CCTGGTGTCAGCCGGCTGGAGTGG-3'

CCTF 4:
(SEQ ID. NO: 62)
5'-CCTGGTTAACCGGCTCGTGGCGATG-3'

CCTF 5:
(SEQ ID. NO: 63)
5'-CCTGGTGCGCTCCATTAGCGTGAGT-3'

CCTF 6:
(SEQ ID. NO: 64)
5'-CCTGGCTTGTAGCCGGCTGGGTAGC-3'

CCTF 7:
(SEQ ID. NO: 65)
5'-CCTGGTGGGATCGAATCACGCGGCA-3'

CCTF 8:
(SEQ ID. NO: 66)
5'-CCTGGCAGCGGCCCAGCTATGAGA-3'

CCTF 9:
(SEQ ID. NO: 67)
5'-CCTGGTCGCAGAGTGCCAACGATCTG-3'

CCTF 10:
(SEQ ID. NO: 68)
5'-CCTGGTATATGGAGCGGCATACGAGC-3'

CCTF 11:
(SEQ ID. NO: 69)
5'-CCTGGTGCAACGATGCACGGCACGT-3'

CCTF 12:
(SEQ ID. NO: 70)
5'-CCTGGTTCCTCGACGGGACTGCGA-3'

CCTF 13:
(SEQ ID. NO: 71)
5'-CCTGGCAGGCGCCTAGCTATGAG-3'

CCTF 14:
(SEQ ID. NO: 72)
5'-CCTGGACAGGCCTGAGACGCGAAGC-3'

CCTF 15:
(SEQ ID. NO: 73)
5'-CCTGGAGCTCGCAGAGCTAACAG-3'

2) PCR Amplification and Determination of SCO Inherent Dissociation Temperature

PCR reaction was performed using the following CFX96 Real-time PCR (Bio-Rad, USA) with 20 μl of total reaction solution of each of Primer 5, 6, 7, 8, 9, 10, 11, 12, 13, 14, 15, 16, 17, 18, 19, 20, 21, 22, 23, 24, 25, 26, 27, 28, 29, 30 and SCO 1, 2, 3, 4, 5, 6, 7, 8, 9, 10, 11, 12, 13 prepared by adding 0.15 μM, PspGI (NEB, USA) 5U, PCR buffer (1×), MgCl$_2$ 2.5 mM, dNTP 200 μM, h-Taq DNA polymerase (Solgent, Korea) 1.6 U, template DNA of genomic DNA of CT, NO, MH, MG, TV, UU, UP, CA, GV, HSV1, HSV2, TP and IC 100 pg/rxn, respectively.

95° C. 15 mins,

95° C. 30 secs, 63° C. 1 min (50 cycles).

A reaction was performed using a cycle at the denaturation temperature of 95° C. for 15 minutes once, and with a cycle at the denaturation temperature of 95° C. for 30 seconds, and an annealing temperature of 63° C. for 1 minute 50 times. After the reaction, the reaction mixture was cooled to 50° C. in the same apparatus, held at 50° C. for 30 seconds, and then slowly heated from 50° C. to 95° C. to obtain an inherent dissociation temperature analysis curve. Data analysis was performed with Bio-Rad CFX Manager 1.6.

FIG. 3(a) shows the results of multiple inherent dissociation temperature measurements for causative organisms of CT, NO, MH, MG, TV, UU, UP, CA, GV, HSV1, HSV2, TP, IC. The peak was observed at the inherent dissociation temperature that each SCO has (CT: FAM 80° C., NO: HEX 76.5° C., MH: HEX 68° C., MG: CalRed610 67.5° C., TV: Quasar670 71.5° C., UU: CalRed610 77° C., UP: FAM 77° C., CA: FAM 65° C., GV: Quasar670 78.5° C., HSV 1: Quasar705 73.5° C., HSV 2: Quasar705 79° C., TP: Quasar705 66° C., IC: Quasar670 63.5° C.) (a)(b)(c)(d)(e)(f), and no peak of SCO visualizing CCTF was observed when the target sequence was not added in the same composition (g).

Therefore, it was proved that the target nucleic acid sequence can be detected more quickly and simply than the conventional PCR method by analyzing the fluorescence of the SCO using the real-time PCR instrument, simultaneously with the PCR using the marking technique of CCTF.

2. Formation of CCTF in Multi-Target PCR of the Causative Organism for the Gastrointestinal Diseases and Analysis for the Inherent Dissociation Temperature Peak of CCTF CCTF analysis was performed with Real-time PCR instrument for DNA of the causative organisms of the gastrointestinal diseases, Rotavirus A(RVA), Astrovirus (AstV), Adenovirus F40(AdV 40), Adenovirus F41(AdV 41), Norovirus GI(NoV GI), Norovirus GII(NoV GII), and External control (EC).

1) Primer for the Target Sequence of Template DNA Constructed in the Sequence-Specific Manner The forward primer used in this example was CTPO and was constructed on the same principle as in Example 1 above. The 5'end of CTPO was composed of 19-20 mers of nucleotide sequences, and was composed of a sequence non-complementary to DNA of the target sequence so as to form CCTF. The restriction enzyme recognition sequence was consecutively located, and after this up to the 3' end, it was composed of the sequence complementary to each target site to play a role as a primer. The reverse primer was composed of sequence complementary to the target site to be amplified.

In addition, SCO, which forms a complementary bond with CCTF to be a double-stranded template, was positioned by positioning fluorescent offsetting molecules (BHQ-1 or BHQ-2), and the fluorescent reporter molecular was positioned so as to have a certain distance.

Primer information and target sequence information which is amplified and generated are as follows.

Primer 31:
(SEQ ID. NO: 74)
5'-GCAGGAGCCTCTCATCTCG*CCAGGCTCATTTATAGACARCTT CTCACTAATTC-3'

Primer 32:
(SEQ ID. NO: 75)
5'-AGTTTTTTCTGATCCAATYTGYTCTATTTC-3'

Primer 33:
(SEQ ID. NO: 76)
5'-TCAGACGGTTCGAGGCTCC*CCAGGARGATYAAGCGTGGAGTA TAYATGG-3'

Primer 34:
(SEQ ID. NO: 77)
5'-TTTGCGTGCYTCTTCACACGC-3'

Primer 35:
(SEQ ID. NO: 78)
5'-AACGCGAATCGACCGGAT*CCAGGCGCGATGTGTTTGCCGATA AAAC-3'

Primer 37:
(SEQ ID. NO: 79)
5'-CATTGCGTCTGCCCCACTTG-3'

Primer 38:
(SEQ ID. NO: 80)
5'-AACGCGAATCGACCGGAT*CCAGGAAACAAGAACACCTATGCCT ACATGAAC-3'

Primer 39:
(SEQ ID. NO: 81)
5'-ATGTTAACGTCCTTCCTGAAGTTCCAC-3'

Primer 40:
(SEQ ID. NO: 82)
5'-TAGATCGGACTGCGAATCG*CCAGGGAGATCGCRATCTYCTGC CCGA-3

Primer 41:
(SEQ ID. NO: 83)
5'-RGCGTCCTTAGACGCCATCATC-3

Primer 42:
(SEQ ID. NO: 84)
5'-ATCTACAGCGTCGCATCACG*CCAGGCGCAATCTGGCTCCCART TTTGTG-3

Primer 43:
(SEQ ID. NO: 85)
5'-GCGTCAYTCGACGCCATCYTCA-3

Primer 44:
(SEQ ID. NO: 86)
5'-CATAGGTCGAGGTCCTCAC*CCAGGGCAAACTCCGGCATCTACTA ATAGACG-3

Primer 45:
(SEQ ID. NO: 87)
5'-AAGCGGTGATCCGCACAGTG-3

SCO 14:
(SEQ ID. NO: 88)
TCGGCCGATCGTCCATAGAGTCAAGC[T(HEX)]CGCAGGAGCCTCTCA TCTCG[BHQ1]

SCO 15:
(SEQ ID. NO: 89)
TCACGATGAGCGAGTTGAGCTACG[T(Calred 610]ATCAGACGGTTCGAGGCTCC[BHQ2]

SCO 16:
(SEQ ID. NO: 90)
TGTTCAATATATAATGATAATATG[T(Calred610)]AACGCGAAT CGACCGGAT[BHQ2]

SCO 17:
(SEQ ID. NO: 91)
TGTTCAATATATAATGATAATATG[T(Calred610)]AACGCGAA TCGACCGGAT[BHQ2]

SCO 18:
(SEQ ID. NO: 92)
ACATTTATAATACAGTATTTTA[T(FAM)]TAGATCGGACTGCGAAT CG[BHQ1]

SCO 19:
(SEQ ID. NO: 93)
AGCTCCTGCCAGTACTGCCATCCA[T(FAM)]ATCTACAGCGTC GCATCACG[BHQ1]

SCO 20:
(SEQ ID. NO: 94)
TAGTTATAATGAATAACTATTAT[T(HEX)]CATAGGTCGAGGTC CTCAC[BHQ1]

Amplified product 16: GenBank: KT694942.1/Position (start-end): 19-99

(SEQ ID. NO: 95)
GCAGGAGCCTCTCATCTCG *CCAGG*CTCATTTATAGACARCTTCTCAC TAATTCATATTCAGTAGATTTACATGATGAAATAGARCARATTGGATCAG AAAAAACT

Amplified product 17: GenBank: AB000287.1/Position (start-end): 2232-2321

(SEQ ID. NO: 96)
TCAGACGGTTCGAGGCTCC *CCAGG*ARGATYAAGCGTGGAGTATAYAT GGACCTGCTTGTCTCGGGGGCAAGCCCAGGCAATGCATGGTCCCATGCGT GTGAAGARGCACGCAAA

Amplified product 18: GenBank: KM274923.1/Position (start-end): 121-179

(SEQ ID NO: 97)
AACGCGAATCGACCGGAT*CCAGG*CGCGATGTGTTTGCCGATAAAACGT

ACCAACCGGAGCCCCAAGTGGGGCAGACGCAATG

Amplified product 19: GenBank: AB330122.1/Position (start-end): 1407-1691

(SEQ ID NO: 98)
AACGCGAATCGACCGGAT *CCAGG*AAACAAGAACACCTATGCCTACAT

GAACGGTCGGGTGGCGGTTCCTAGCGCCCTCGATACCTACGTAAACATCG

GGGCACGGTGGTCTCCAGATCCCATGGACAATGTTAACCCCTTCAATCAC

CACCGTAACGCCGGTCTGCGCTATCGATCCATGCTCTTGGGCAACGGGCG

TTACGTACCCTTCCACATTCAAGTCCCCCAGAAGTTTTTTGCCATTAAAA

ATCTCCTCCTCTTACCGGGTTCCTACACCTACGAGTGGAACTTCAGGAAG

GACGTTAACAT

Amplified product 20: GenBank: LN854564.1/Position (start-end): 5325-5378

(SEQ ID NO: 99)
TAGATCGGACTGCGAATCG * CCAGG*GAGATCGCRATCTYCTGCCCGAA

TTCGTAAATGATGATGGCGTCTAAGGACGCY

Amplified product 21: GenBank: KT202798.1/Position (start-end): 5060-5107

(SEQ ID NO: 100)
ATCTACAGCGTCGCATCACG * CCAGG*CGCAATCTGGCTCCCARTTTTG

TGAATGARGATGGCGTCGARTGACGC

Amplified product 22: GenBank: EF204940.1/Position (start-end): 1707-1878

(SEQ ID NO: 101)
CATAGGTCGAGGTCCTCAC* CCAGG*GCAAACTCCGGCATCTACTAATAG

ACGCCGGCCATTCAAACATGAGGATTACCCATGTCGAAGACAACAAAGAA

GTTCAACTCTTTATGTATTGATCTTCCTCGCGATCTTTCTCTCGAAATTT

ACCAATCAATTGCTTCTGTCGCTACTGGAAGCGGTGATCCGCACAGTG

The bold and slanted font of the Primer sequence means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. The sequence of the CCTF produced from the amplified product is as follows.

CCTF 16:
(SEQ ID NO: 102)
5'-CCTGGTGTCAGCCGGCTGGAGTGG-3'

CCTF 17:
(SEQ ID NO: 103)
5'-CCTGGTTAACCGGCTCGTGGCGATG-3'

CCTF 18:
(SEQ ID NO: 104)
5'-CCTGGTGCGCTCCATTAGCGTGAGT-3'

CCTF 19:
(SEQ ID NO: 105)
5'-CCTGGCTTGTAGCCGGCTGGGTAGC-3'

CCTF 20:
(SEQ ID NO: 106)
5'-CCTGGTGGGATCGAATCACGCGGCA-3'

CCTF 21:
(SEQ ID NO: 107)
5'-CCTGGCAGCGGCCCAGCTATGAGA-3'

CCTF 22:
(SEQ ID NO: 108)
5'-CCTGGTCGCAGAGTGCCAACGATCTG-3'

CCTF 23:
(SEQ ID NO: 109)
5'-CCTGGTATATGGAGCGGCATACGAGC-3'

CCTF 24:
(SEQ ID NO: 110)
5'-CCTGGTGCAACGATGCACGGCACGT-3'

CCTF 25:
(SEQ ID NO: 111)
5'-CCTGGTTCCTCGACGGGACTGCGA-3'

CCTF 26:
(SEQ ID NO: 112)
5'-CCTGGCAGGCGCCTAGCTATGAG-3'

CCTF 27:
(SEQ ID NO: 113)
5'-CCTGGACAGGCCTGAGACGCGAAGC-3'

CCTF 28:
(SEQ ID NO: 114)
5'-CCTGGAGCTCGCAGAGCTAACAG-3'

2) PCR Amplification and Determination of the Inherent Dissociation Temperature of SCO The following PCR reaction was performed using CFX96 Real-time PCR (Bio-Rad, USA) with 20 µl of total reaction solution of each of Primer 31, 32, 33, 34, 35, 36, 37, 38, 39, 40, 41, 42, 43, 44, 45 and SCO 14, 15, 16, 17, 18, 19, 20 prepared by adding 0.15 µM, PspGI (NEB, USA) 1U, PCR buffer (1×), MgCl$_2$ 2.5 mM, dNTP 200 µM, DTT 0.1 mM, RNase Inhibitor 1U, SuperiorScript III (Enzynomics, Korea) 1 U and the nucleic acid of the genomic RNA of RVA, AstV, AdV 40, AdV41, NoV GI, NoV GII and EC(MS2 phage) 1×10$^{-4}$ pg/rxn, respectively.

55° C. 20 mins, 95° C. 10 mins
95° C. 30 secs, 63° C. 1 mins (50 cycles).

A reverse transcription reaction was performed using a cycle at the denaturation temperature of 55° C. for 20 minutes once, and with a cycle at the denaturation temperature of 95° C. for 10 minutes 1 time, and with a cycle at an annealing temperature of 63° C. for 1 minute 50 times repeatedly. After the reaction, the reaction mixture was cooled to 50° C. in the same apparatus, held at 50° C. for 30 seconds, and then slowly heated from 50° C. to 95° C. to obtain an inherent dissociation temperature analysis curve. Data analysis was performed with Bio-Rad CFX Manager 1.6.

FIG. 4 shows the results of multiple inherent dissociation temperature measurements for causative organisms of RVA, AstV, AdV 40, AdV 41, NoV GI, NoV GII. It was identified that the peak was observed at the inherent dissociation temperature that each SCO has: RVA: HEX 78° C., AstV: CalRed610 78° C., AdV 40: CalRed610 67° C., AdV 41: CalRed610 67° C., NoV GI: FAM 68° C., NoV GiI: FAM 84° C., EC: HEX 69° C. (a)(b)(c)(d), and no peak of SCO visualizing CCTF was observed when the target sequence was not added in the same composition (e).

Therefore, it was proved that the target nucleic acid sequence can be detected more quickly and simply than the conventional PCR method by analyzing the fluorescence of the SCO using the real-time PCR instrument, simultaneously with the PCR using the marking technique of CCTF.

3. Formation of CCTF and Analysis for the Inherent Dissociation Temperature Peak of CCTF in Multi-Target PCR for Detecting the Human Papillomavirus CCTF analysis was performed with Real-time PCR instrument for DNA of subtypes of Human Papillomavirus (HPV), 16 type, 18 type, 33 type, 35 type, 51 type, 53 type, 59 type, 68a type, 82 type and Internal control (IC).

1) Primer of the Target Sequence Template DNA, Constructed in the Sequence-Specific Manner The forward primer used in this example was CTPO and was constructed on the same principle as in Example 1 above. The 5'end of CTPO was composed of 19~20 mers of nucleotide sequences, and was composed of a sequence non-complementary to DNA of the target sequence to form CCTF. The restriction enzyme recognition sequence was consecutively located, and after this up to the 3' end, a sequence complementary to each target site was composed to play a role as a primer. The reverse primer was composed of sequence complementary to the target site to be amplified.

In addition, SCO, which forms a complementary bond with CCTF to be a double-stranded template, was positioned by positioning fluorescent offsetting molecules (BHQ-1 or BHQ-2), and the fluorescent reporter molecular was positioned so as to have a certain distance.

Primer information and target sequence information which is amplified and generated are as follows.

```
Primer 46:
                                      (SEQ ID. NO: 115)
5'-CTCTGATAGCGACTGCTCGCA*CCAGGATAATATAAGGGGTCGG

TGGACCGG-3'

Primer 47:
                                      (SEQ ID. NO: 116)
5'-CTCCATGCATGATTACAGCTGGGTT-3'

Primer 48:
                                      (SEQ ID. NO: 117)
5'-ATCGGTCTCCTGAAAGCTGCG*CCAGGCAGAAGGTACAGACGGG

GAGGGC-3'

Primer 49:
                                      (SEQ ID. NO: 118)
5'-CACCTCCAGCCGCTCCCCTAAT-3'

Primer 50:
                                      (SEQ ID. NO: 119)
5'-CTGGCGTAGAGCACTTACGCT*CCAGGCAACGATAACCGACCAC

CACAAGCA-3'

Primer 51:
                                      (SEQ ID. NO: 120)
5'-CGGGGTCTGCACAGAACAGCTTT-3'

Primer 52:
                                      (SEQ ID. NO: 121)
5'-CTGGCGTAGAGCACTTACGCT*CCAGGAGGACCCAGCTGAACGA

CCTTACAA-3'

Primer 53:
                                      (SEQ ID. NO: 122)
5'-CTGTCCACCGTCCACCGATGTTATG-3'

Primer 54:
                                      (SEQ ID. NO: 123)
5'-CTGGCGTAGAGCACTTACGCT*CCAGGGCTGGCAACGTACACGACAA

CG-3'

Primer 55:
                                      (SEQ ID. NO: 124)
5'-GCTGTACAACGCGAAGGGTGTC-3'

Primer 56:
                                      (SEQ ID. NO: 125)
5'-CTGGCGTAGAGCACTTACGCT*CCAGGTCCACCTATGCACCGAA

ACCTCCAA-3'

Primer 57:
                                      (SEQ ID. NO: 126)
5'TGCAGTGACGAGTCCCCGTGTAGTA-3'

Primer 58:
                                      (SEQ ID. NO: 127)
5'-CTGGCGTAGAGCACTTACGCT*CCAGGGACTGTACACCGTATGC

AGCGTG-3'

Primer 59:
                                      (SEQ ID. NO: 128)
5'-GCGTATCAGCAGCTCATGTAA-3'

Primer 60:
                                      (SEQ ID. NO: 129)
5'-CTGGCGTAGAGCACTTACGCT*CCAGGACAAACTCGACGTCGTC

TCGGAA-3'

Primer 61:
                                      (SEQ ID. NO: 130)
5'-CAGGTCACCACAACAAAGGCTCCGT-3'

Primer 62:
                                      (SEQ ID. NO: 131)
5'-ATCAGGACGCAGCCGGTTCT*CCAGGCCAAGGACAGGTACGGCT

GTCATC-3'

Primer 63:
                                      (SEQ ID. NO: 132)
5'-GGTGCCCTTGAGGTTGTCCAGGTG-3'

SCO 21:
                                      (SEQ ID. NO: 133)
GAGACGTTTAAGTCCGCGACCGCTC[T(HEX)]CTGATAGCGACTGC

TCGCA[BHQ1]

SCO 22:
                                      (SEQ ID. NO: 134)
CAGGCGACGTCCATATGGTGCGCTA[T(FAM)]CGGTCTCCTGAAAG

CTGCG[BHQ1]

SCO 23:
                                      (SEQ ID. NO: 135)
CCCTTAGGTAACGTCTGGC[T(Qusar 670)]GGCGTAGAGCACTTAC

GCT[BHQ 2]
```

-continued

SCO 24:

(SEQ ID. NO: 136)
AAACTTTAATTATTGTATA[T(FAM)]CAGGACGCAGCCGGTTCT

[BHQ 1]

Amplified product 23: GenBank: LC193821.1/Position (start-end): 480-571

(SEQ ID. NO: 137)
CTCTGATAGCGACTGCTCGCA *CCAGG*ATAATATAAGGGGTCGGTGGA

CCGGTCGATGTATGTCTTGTTGCAGATCATCAAGAACACGTAGAGAAACC

CAGCTGTAATCATGCATGGAG

Amplified product 24: GenBank: KC470209.1/Position (start-end): 538-747

(SEQ ID. NO: 138)
ATCGGTCTCCTGAAAGCTGCG *CCAGG*CACGACAGGAACGACTCCAAC

GACGCAGAGAAACACAAGTATAATATTAAGTATGCATGGACCTAAGGCAA

CATTGCAAGACATTGTATTGCATTTAGAGCCCCAAAATGAAATTCCGGTT

GACCTTCTATGTCACGAGCAATTAAGCGACTCAGAGGAAGAAAACGATGA

AATAGATGGAGTTAATCATCAACATTTACCAGCCCGACG

Amplified product 25: GenBank: KU298894.1/Position (start-end): 535-860

(SEQ ID. NO: 139)
CTGGCGTAGAGCACTTACGCT *CCAGG*ACGCCATGAGAGGACACAAGC

CAACGTTAAAGGAATATGTTTTAGATTTATATCCTGAACCAACTGACCTA

TACTGCTATGAGCAATTAAGTGACAGCTCAGATGAGGATGAAGGCTTGGA

CCGGCCAGATGGACAAGCACAACCAGCCACAGCTGATTACTACATTGTAA

CCTGTTGTCACACTTGTAACACCACAGTTCGTTTATGTGTCAACAGTACA

GCAAGTGACCTACGAACCATACAGCAACTACTTATGGGCACAGTGAATAT

TGTGTGCCCTACCTGTGCACAACAATAAACATCATCTACAATGGCCGATC

CTGAA

Amplified product 26: GenBank: M74117.1/Position (start-end): 117-509

(SEQ ID. NO: 140)
CTGGCGTAGAGCACTTACGCT *CCAGG*AGGAGGACCCAGCTGAACGAC

CTTACAAACTGCATGATTTGTGCAACGAGGTAGAAGAAAGCATCCATGAA

ATTTGTTTGAATTGTGTATACTGCAAACAAGAATTACAGCGGAGTGAGGT

ATATGACTTTGCATGCTATGATTTGTGTATAGTATATAGAGAAGGCCAGC

CATATGGAGTATGCATGAAATGTTTAAAATTTTATTCAAAAATAAGTGAA

TATAGATGGTATAGATAGTGTGTATGGAGAAACGTTAGAAAAACAATG

CAACAAACAGTTATGTCATTTATTAATTAGGTGTATTACATGTCAAAAAC

CGCTGTGTCCAGTTGAAAAGCAAAGACATTTAGAAGAAAAAAAACGATTC

CATAACATCGGTGGACGGTGGACAG

Amplified product 27: GenBank: KU298905.1/Position (start-end): 512-812

(SEQ ID. NO: 141)
CTGGCGTAGAGCACTTACGCT *CCAGG*GCTGGCAACGTACACGACAAC

GTAACGAAACCCAAGTGTAATAAAGCCATGCGTGGTAATGTACCACAATT

AAAAGATGTAGTATTGCATTTAACACCACAGACTGAAATTGACTTGCAAT

GCTACGAGCAATTTGACAGCTCAGAGGAGGAGGATGAAGTAGATAATATG

CGTGACCAGCTACCAGAAAGACGGGCTGGACAGGCTACGTGTTACAGAAT

TGAAGCTCCGTGTTGCAGGTGTTCAAGTGTAGTACAACTGGCAGTGGAAA

GCAGTGGAGACACCCTTCGCGTTGTACAGC

Amplified product 28: GenBank: KU298906.1/Position (start-end): 3374-3558

(SEQ ID. NO: 142)
CTGGCGTAGAGCACTTACGCT *CCAGG*TCCACCTATGCACCGAAACCT

CCAAGACCTCCGCATTGTCCGTGGGTGCCAAAGACACACACCTACAACCA

CCACAGAAACGACGACGACCAGACGTCACAGACTCCAGAAACACCAAGTA

CCCCAACAACCTTTTGCGGGGACAACAATCCGTGGACAGTACTACACGGG

GACTCGTCACTGCA

Amplified product 29: GenBank: KU298922.1/Position (start-end): 226-366

(SEQ ID. NO: 143)
CTGGCGTAGAGCACTTACGCT *CCAGG*GTTAAGACCGAAAACGGTGCA

TATAAAGGTAGTTAGAAAGAAAAGGGCAACGGCATGGCACGCTTTGAGGA

TCCTACACAACGACCATACAAACTGCCTGACTTGAGCACAACATTGAATA

TTCCTCTGCATGATATTCGC

Amplified product 30: GenBank: KC470271.1/Position (start-end): 3389-3541

(SEQ ID. NO: 144)
CTGGCGTAGAGCACTTACGCT *CCAGG*ATGGCGCTATTTCACAACCCT

GAGGAACGGCCATACAAATTGCCAGACCTGTGCAGGACATTGGACACTAC

ATTGCATGACGTTACAATAGAGTGTGTCTATTGCAGAAGGCAACTACAAC

GGACAGAGGTATATGAATTTGCCTTTAGTGAC

Amplified product 31: GenBank: EF450778.1/Position (start-end): 431-681

(SEQ ID. NO: 145)
GCTCATATGCGGCGCCATTTA*CCAGG*GCAGGTTGCTATCAAGGTTACA

AGACAGGTTTAAGGAGACCAATAGAAACTGGGCATGTGGAGACAGAGAAG

ACTCTTGGGTTTCTGATAGGCACTGACTCTCTCTGCCTATTGGTCTATTT

TCCCACCCTTAGGCTGCTGGTGGTCTACCCTTGGACCCAGAGGTTCTTTG

AGTCCTTTGGGGATCTGTCCACTCCTGATGCTGTTATGGGCAACCCTAAG

GTGAAGGCTCATGGCAAGAAAGTGCTCGG

The bold and slanted font of the Primer sequence means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. The sequence of the CCTF produced from the amplified product is as follows.

```
CCTF 29:
                                    (SEQ ID. NO: 146)
5'-TGCGAGCAGTCGCTATCAGAG-3'

CCTF 30:
                                    (SEQ ID. NO: 147)
5'-CGCAGCTTTCAGGAGACCGAT-3'

CCTF 31:
                                    (SEQ ID. NO: 148)
5'-AGCGTAAGTGCTCTACGCCAG-3'

CCTF 32:
                                    (SEQ ID. NO: 149)
5'-AGAACCGGCTGCGTCCTGAT-3'
```

2) PCR Amplification and Determination of the Inherent Dissociation Temperature of SCO The following PCR reaction was performed using CFX96 Real-time PCR (Bio-Rad, USA) with 20 µl of total reaction solution of each of Primer 46, 47, 48, 49, 50, 51, 52, 53, 54, 55, 56, 57, 58, 59, 60, 61, 62, 63 and SCO 21, 22, 23, 24 prepared by adding 0.15 µM, PspGI (NEB, USA) 5U, PCR buffer (1×), MgCl 2 2.5 mM, dNTP 200 µM, h-Taq DNA polymerase (Solgent, Korea) 1.6 U and HPV type 16, type 18, type 33, type 35, type 51, type 53, type 59, type 68a, type 82 and template DNA of genomic DNA of IC 100 pg/rxn, respectively.

95° C. 15 mins,

95° C. 30 secs, 63° C. 1 mins (50 cycles).

A reaction was performed using a cycle at the denaturation temperature of 95° C. for 15 minutes once, and with a cycle at the denaturation temperature of 95° C. for 30 second and at an annealing temperature of 63° C. for 1 minute 50 times repeatedly. After the reaction, the reaction mixture was cooled to 50° C. in the same apparatus, held at 50° C. for 30 seconds, and then slowly heated from 50° C. to 95° C. to obtain an inherent dissociation temperature analysis curve. Data analysis was performed with Bio-Rad CFX Manager 1.6.

FIG. 5 shows the results of multiple inherent dissociation temperature measurements for each target of type 16, type 18, type 33, type 35, type 51, type 53, type 59, type 68a, type 82, IC. It was identified that the peak was observed at the inherent dissociation temperature that each SCO has (type 16: HEX 76.5° C., type 18: FAM 78° C., type 33: Quasar670 71° C., type 35: Quasar670 71° C., type 51: Quasar670 71° C., type 53: Quasar670 71° C., type 59: Quasar670 71° C., type 68 a: Quasar670 71° C., type 82: Quasar670 71° C., IC: Quasar670 67.5° C.) (a)(b)(c)(d), and no peak of SCO visualizing CCTF was observed when the target sequence was not added in the same composition (e).

Therefore, it was proved that the target nucleic acid sequence can be detected more quickly and simply than the conventional PCR method by analyzing the fluorescence of the SCO using the real-time PCR instrument, simultaneously with the PCR using the marking technique of CCTF.

4. Formation of CCTF and Analysis for the Inherent Dissociation Temperature Peak of CCTF in Multi-Target PCR for Detecting the Causative Organism of the Respiratory Diseases CCTF analysis was performed using Real-time PCR instrument of nucleic acids of the causative organisms of the respiratory diseases, Influenza A/H1N1(Flu A/H1N1), Influenza A/H3N2(Flu A/H3N2), Influenza A/H1N1/2009pdm (Flu A/H1N1/2009pdm), Influenza B(Flu B), Parainfluenza 1(PIV1), Parainfluenza 3(PIV3), Respiratory syncytial virus A(RSV A), Respiratory syncytial virus B(RSV B), Human metapneumovirus(MPV), Adenovirus(AdV) and External control (EC).

1) Primer for the Target Sequence of Template DNA, Constructed in the Sequence-Specific Manner The forward primer used in this example was CTPO and was constructed on the same principle as in Example 1 above. The 5'end of CTPO was composed of 19-20 mers of nucleotide sequences, and was composed of a sequence non-complementary to DNA of the target sequence so as to form CCTF. The restriction enzyme recognition sequence was then consecutively located, and after this up to the 3' end, a sequence complementary to each target site was composed to play a role as a primer. The reverse primer was composed of sequence complementary to the target site to be amplified.

In addition, SCO, which forms a complementary bond with CCTF to be a double-stranded template, was positioned by positioning fluorescent offsetting molecules (BHQ-1 or BHQ-2), and the fluorescent reporter molecular was positioned so as to have a certain distance.

Primer information and target sequence information which is amplified and generated are as follows.

```
Primer 64:
                                    (SEQ ID. NO: 150)
5'-TTGCTATGGCTGACGGGGAAGAATGG-3'

Primer 65:
                                    (SEQ ID. NO: 151)
5'-GCCCCGTTGAGAGCACGAAT*CCAGGGGGGTGAATCTTCTGCTT

AATGTGAAGACA C-3'

Primer 66:
                                    (SEQ ID. NO: 152)
5'-GGGCACCATGCAGTACCAAACGGAAC-3'

Primer 67:
                                    (SEQ ID. NO: 153)
5'-CCGTGGCGCGAACTTATCGA*CCAGGATCACACTGAGGGTCTCC

CAATAGAGC-3'

Primer 68:
                                    (SEQ ID. NO: 154)
5'-TCAAAGACTAAGTGGTGCCATGGATGAAC-3'

Primer 69:
                                    (SEQ ID. NO: 155)
5'-AAGTGACCTGCCATTGCGCG*CCAGGTATGTCTACAGCAGAGGG

ACCCAGC-3'

Primer 70:
                                    (SEQ ID. NO: 156)
5'-GGCTTAGAGCACCGCGTCATT*CCAGGTGTCGCTACTGGAAGCG

GTGATC-3'

Primer 71:
                                    (SEQ ID. NO: 157)
5'-GCGATAGCTAAGGTACGACGGGTC-3'

Primer 72:
                                    (SEQ ID. NO: 158)
5'-GTAGATTCGATCCATGCTCCTCTACTACC-3'
```

Primer 73:
(SEQ ID. NO: 159)
5'-CGTCTTACATGCGCAAGCGG*CCAGGTGATATTGAGTTCGGTAATGCAAGATCTGC-3'

Primer 74:
(SEQ ID. NO: 160)
5'-CCATAGAGATGGCAATAGATGAAGAGC-3'

Primer 75:
(SEQ ID. NO: 161)
5'-AGGCGTTCCGCTTCAACGAG*CCAGGTTGTCAGATTCTGTAGCTTGCTCAGTC-3'

Primer 76:
(SEQ ID. NO: 162)
5'-GGTGGTGATCCCAACTTGTTATATCGAAG-3'

Primer 77:
(SEQ ID. NO: 163)
5'-TCCGTCTGCGAAGATCTGAGC*CCAGGTTCAATCTATCRTCTGACAGATCTTGAAGT-3'

Primer 78:
(SEQ ID. NO: 164)
5'-GTGTCACGACGCGCGAATCT*CCAGGAGATCGTGACCAGTATAATAGCTCAACAC-3'

Primer 79:
(SEQ ID. NO: 165)
5'-TTTCAGACAATGCAGGGATAACACCAGC-3'

Primer 80:
(SEQ ID. NO: 166)
5'-CCCAGAACGATTTGCGGCGT*CCAGGCTTGGTCCTCTCTTAGGAGGCAAGC-3'

Primer 81:
(SEQ ID. NO: 167)
5'-AGGATGCTTCGGAGTACCTGAG-3'

Primer 82:
(SEQ ID. NO: 168)
5'-TGCATTGCCGTCGCAGAGAC*CCAGGCAACGGGCACGAAGCGCATC-3'

Primer 83:
(SEQ ID. NO: 169)
GCCCTAATGATAAGACAGGCAGTTGTGG

Primer 84:
(SEQ ID. NO: 170)
5'-ATGCGCTTGGATTGCCGATG*CCAGGAGCCCTGTTAGTTCTGGATGCTGAACA-3'

SCO 33:
(SEQ ID. NO: 171)
CTTATAGATTATA[T(FAM)]TGCCCCGTTGAGAGCACGAAT[BHQ1]

SCO 34:
(SEQ ID. NO: 172)
CTAAGTAAGCCTATATCGAAT[T(FAM)]CCGTGGCGCGAACTTATCGA[BHQ1]

SCO 35:
(SEQ ID. NO: 173)
CGTACTGCACTCGCCTACGAC[T(Cal Fluor Red 610)]AAGTGACCTGCCATTGCGCG[BHQ2]

SCO 36:
(SEQ ID. NO: 174)
CTTATAAGTTACA[T(Cal Fluor Red 610)]GGCTTAGAGCACCGCGTCATT[BHQ2]

SCO 37:
(SEQ ID. NO: 175)
CTAATTGTAATAC[T(Quasar 670)]CGTCTTACATGCGCAAGCGG[BHQ2]

SCO 38:
(SEQ ID. NO: 176)
CTAATCGTATGAGATCTATGA[T(Quasar 670)]AGGCGTTCCGCTTCAACGAG[BHQ2]

SCO 39:
(SEQ ID. NO: 177)
TCATAGACATTTA[T(Cal Fluor Gold 540)]TCCGTCTGCGAAGATCTGAGC[BHQ1]

SCO 40:
(SEQ ID. NO: 178)
TACGAATCTGACCTAGTAAGA[T(Cal Fluor Gold 540)]GTGTCACGACGCGCGAATCT[BHQ1]

SCO 41:
(SEQ ID. NO: 179)
TGCCACTAACAGGCCGCTAGA[T(Cal Fluor Gold 540)]CCCAGAACGATTTGCGGCGT[BHQ1]

SCO 42:
(SEQ ID. NO: 180)
TCGAGCGTGCGCCAGATCCA[T(Quasar 670)]TGCATTGCCGTCGCAGAGAC[BHQ2]

SCO 43:
(SEQ ID. NO: 181)
TCGACTGTGCCTGCGTCCGTA[T(FAM)]ATGCGCTTGGATTGCCGATG[BHQ1]

Amplified product 32: GenBank: KU558787.1/Position (start-end): 428-621

(SEQ ID. NO: 182)
TTGCTATGGCTGACGGGGAAGAATGGTTTGTACCCAAACCTGAGCATGTCCTATGTAAACAACAAAGAGAAAGAAGTCCTTGTGCTATGGGTGTTCATCACCCACCTAACATAGGGAACCAAAGGGCCCTCTACCATACAGAAAATGCTTATGTCTCTGTAGTGTCTTCACATTATAGCAGAAGATTCACCCC*CCTGGATTCGTGCTCTCAACGGGGC

Amplified product 33: GenBank: CY221934.1/Position (start-end): 111-296

(SEQ ID. NO: 183)
GGGCACCATGCAGTACCAAACGGAACGATAGTGAAAACAATCACAAATGACCAAATTGAAGTTACTAATGCTACTGAGTTGGTTCAGAATTCCTCAATAGGTGAAATATGCGACAGTCCTCATCAGATCCTTGATGGAGAGAACTGCACACTAATAGATGCTCTATTGGGAGACCCTCAGTGTGAT*CCTGGTCGATAAGTTCGCGCCACGG

Amplified product 34: GenBank: CY221750.1/Position (start-end): 1291-1501

(SEQ ID. NO: 184)
TCAAAGACTAAGTGGTGCCATGGATGAACTCCACAACGAAATACTCGAGC

TGGATGAAAAAGTGGATGACCTCAGAGCTGACACTATAAGCTCACAAATA

GAACTTGCAGTCTTGCTTTCCAACGAAGGAATAATAAACAGTGAAGATGA

GCATCTATTGGCACTTGAGAGAAAACTAAAGAAAATGCTGGGTCCCTCTG

CTGTAGACATA**CCTG*CGCGCAATGGCAGGTCACTT

Amplified product 35: GenBank: JF719743.1/Position (start-end): 1816-1950

(SEQ ID. NO: 185)
GGCTTAGAGCACCGCGTCATT**CCAGG*TGTCGCTACTGGAAGCGGTGA

TCCGCACAGTGACGACTTTACAGCAATTGCTTACTTAAGGGACGAATTGC

TCGCAAAGCATCCGACCTTAGGTTCTGGTAATGACGAGGCGACCCGTCGT

ACCTTAGCTATCGC

Amplified product 36: GenBank: KX639498.1 z/Position (start-end): 4035-4253

(SEQ ID. NO: 186)
GTAGATTCGATCCATGCTCCTCTACTACCATGGTCCAGCCGACTGAGACA

AGGGATGATATATAATGCCAATAAAGTAGCTCTGGCACCCCAATGTCTCC

CAGTCGACAAAGATATCAGATTCAGAGTTGTATTTGTCAACGGAACATCA

CTGGGTACAATCACAATTGCCAAGGTCCCAAAAACTCTTGCAGATCTTGC

ATTACCGAACTCAATATCA**CCTGG*CCGCTTGCGCATGTAAGACG

Amplified product 37: GenBank: KY369876.1/Position (start-end): 1310-1463

(SEQ ID. NO: 187)
CCATAGAGATGGCAATAGATGAAGAGCCAGAACAATTCGAACATAGAGCA

GACCAAGAACAAGATGGGGAACCTCAATCATCTATAATCCAATATGCTTG

GGCAGAAGGAAACAGAAGCGATGACCGGACTGAGCAAGCTACAGAATCTG

ACAA**CCTGG*CTCGTTGAAGCGGAACGCCT

Amplified product 38: GenBank: KX894800.1/Position (start-end): 11378-11529

(SEQ ID. NO: 188)
GGTGGTGATCCCAACTTGTTATATCGAAGTTTCTATAGAAGAACTCCTGA

TTTCCTCACAGAGGCTATAGTTCACTCTGTGTTCATACTTAGTTATTATA

CAAACCATGATTTAAAGGATAAACTTCAAGATCTGTCAGAYGATAGATTG

AA**CCTGG*GCTCAGATCTTCGCAGACGGA

Amplified product 39: GenBank: KY249683.1/Position (start-end): 11465-11577

(SEQ ID. NO: 189)
GGTGGTGATCCTAATTTGTTATATCGAAGCTTTTATAGGAGAACTCCAG

ACTTCCTTACAGAAGCTATAGTACATTCAGTGTTCGTGTTGAGCTATTA

TACTGGTCACGATCT**CCTGG*AGATTCGCGCGTCGTGACAC

Amplified product 40: GenBank: KJ627391.1/Position (start-end): 3631-3933

(SEQ ID. NO: 190)
TTTCAGACAATGCAGGGATAACACCAGCAATATCATTGGACCTAATGAC

TGATGCTGAACTGGCCAGAGCTGTATCATACATGCCAACATCTGCAGGG

CAGATAAAGCTGATGTTGGAGAACCGCGCAATGGTAAGGAGAAAAGGAT

TTGGAATCCTAATAGGGGTCTACGGAAGCTCTGTGATTTACATGGTTCA

ATTGCCGATCTTTGGTGTCATAGATACACCTTGTTGGATAATCAAGGCA

GCTCCCTCTTGCTCAGAAAAAAACGGGAATTATGCTTGCCTCCTAAGAG

AGGACCAAG* *CCTGG*ACGCCGCAAATCGTTCTGGG

Amplified product 41: GenBank: KT963081.1/Position (start-end): 18437-18598

(SEQ ID. NO: 191)
AGGATGCTTCGGAGTACCTGAGTCCGGGTCTGGTGCAGTTCGCCCGTGC

AACAGACACCTACTTCAGTATGGGGAACAAGTTTAGAAACCCCACAGTG

GCGCCCACCCACGATGTGACCACCGACCGTAGCCAGCGACTGATGCTGC

GCTTCGTGCCCGITG* *CCTGG*GTCTCTGCGACGGCAATGCA

Amplified product 42: GenBank: CY221624.1/Position (start-end): 988-1252

(SEQ ID. NO: 192)
GCCCTAATGATAAGACAGGCAGTTGTGGTCCAGTATCGTCTAATGGAGC

AAATGGAGTAAAAGGATTTTCATTCAAATACGGCAATGGTGTTTGGATA

GGGAGAACTAAAAGCATTAGTTCAAGAAAAGGTTTTGAGATGATTTGGG

ATCCGAATGGATGGACTGGGACTGACAATAAATTCTCAATAAAGCAAGA

TATCGTAGGAATAAATGAGTGGTCAGGGTATAGCGGGAGTTTTGTTCAG

CATCCAGAACTAACAGGGCT* *CCTG*CATCGGCAATCCAAGCGCAT

The bold and slanted font of the Primer sequence means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. The sequence of the CCTF produced from the amplified product is as follows.

CCTF 33:
(SEQ ID. NO: 193)
5'-ATTCGTGCTCTCAACGGGGC-3'

CCTF 34:
(SEQ ID. NO: 194)
5'-TCGATAAGTTCGCGCCACGG-3'

CCTF 35:
(SEQ ID. NO: 195)
5'-CGCGCAATGGCAGGTCACTT-3'

CCTF 36:
(SEQ ID. NO: 196)
5'-AATGACGCGGTGCTCTAAGCC-3'

-continued

CCTF 37:
(SEQ ID. NO: 197)
5'-CCGCTTGCGCATGTAAGACG-3'

CCTF 38:
(SEQ ID. NO: 198)
5'-CTCGTTGAAGCGGAACGCCT-3'

CCTF 39:
(SEQ ID. NO: 199)
5'-GCTCAGATCTTCGCAGACGGA-3'

CCTF 40:
(SEQ ID. NO: 200)
5'-AGATTCGCGCGTCGTGACAC-3'

CCTF 41:
(SEQ ID. NO: 201)
5'-ACGCCGCAAATCGTTCTGGG-3'

CCTF 42:
(SEQ ID. NO: 202)
5'-GTCTCTGCGACGGCAATGCA-3'

CCTF 43:
(SEQ ID. NO: 203)
5'-CATCGGCAATCCAAGCGCAT-3'

2) PCR Amplification and Determination of SCO Inherent Dissociation Temperature

The following PCR reaction was performed using CFX96 Real-time PCR (Bio-Rad, USA) with 20 µl of total reaction solution of each of 64, 65, 66, 67, 68, 69, 70, 71, 72, 73, 74, 75, 76, 77, 78, 79, 80, 81, 82, 83, 84 and SCO 33, 34, 35, 36, 37, 38, 39, 40, 41, 42, 43 prepared by adding 0.15 µM, PspGI (NEB, USA) 1U, PCR buffer (1×), MgCl$_2$ 2.5 mM, dNTP 200 µM, DTT 0.1 mM, RNase Inhibitor IU. SuperiorScript III (Enzynomics, Korea) 1U Flu A/H1N1, Flu A/H3N2, Flu A/H1N1/2009pdm, the template nucleic acid of the genomic RNA of Flu B, PIV1, PIV3, RSV A, RSV B, hMPV, ADV and MS2 phage 1×10$^4$ copies/rx, respectively.

55° C. 20 mins, 95° C. 10 mins

95° C. 30 secs, 63° C. 1 min (50 cycles).

A reaction was repeatedly performed with a cycle at the reverse transcription reaction temperature of 55° C. for 20 minutes once, and with a cycle at the denaturation temperature of 95° C. for 30 seconds, and an annealing temperature of 63° C. for 1 minute 50 times repeatedly. After the reaction, the reaction mixture was cooled to 50° C. in the same apparatus, held at 50° C. for 30 seconds, and then slowly heated from 50° C. to 95° C. to obtain an inherent dissociation temperature analysis curve. Data analysis was performed with Bio-Rad CFX Manager 1.6.

FIG. 6 shows the results of multiple inherent dissociation temperature measurements for causative organisms of Flu A/H1N1, Flu A/H3N2, Flu A/H1N1/2009pdm, Flu B, PIV1, PIV3, RSV A, RSV B, hMPV, ADV, EC(Ms2 phage). It was confirmed that the peak was observed at the inherent dissociation temperature that each SCO has (Flu A/H1N1: 67.5° C. Flu A/H3N2: 76.5° C., Flu A/H1N1/2009pdm: 86.5° C., Flu B: 83.5° C., PIV1: 66° C., PIV3: 74° C., RSV A: 63.5° C., RSV B: 72° C., hMPV: 86° C., ADV: 85° C.) (a)(b)(c)(d)(e), and no peak of SCO visualizing CCTF was observed when the target sequence was not added in the same composition (I).

Therefore, it was proved that the target nucleic acid sequence can be detected more quickly and simply than the conventional PCR method by analyzing the fluorescence of the SCO using the real-time PCR instrument, simultaneously with the PCR using the marking technique of CCTF.

5. Formation of CCTF and Analysis for the Inherent Dissociation Temperature Peak of CCTF in Multi-Target PCR for Analyzing the Single Nucleotide Polymorphism Genotype of BDNF Gene CCTF analysis was performed with Real-time PCR instrument for analyzing the genotype of rs6265, single nucleotide polymorphism of BDNF gene.

1) Primer for the Target Sequence of Template DNA, Constructed in the Sequence-Specific Manner The forward primer used in this example was CTPO and was constructed on the same principle as in Example 1 above. The 5'end of CTPO was composed of 19-20 mers of nucleotide sequences, and was composed of a sequence non-complementary to DNA of the target sequence so as to form CCTF. The restriction enzyme recognition sequence was then located, and from this up to the 3' end, a sequence complementary to each target site was composed to play a role as a primer. The reverse primer was composed of sequence complementary to the target site to be amplified.

In addition, SCO, which forms a complementary bond with CCTF to be a double-stranded template, was positioned by positioning fluorescent offsetting molecules (BHQ-1 or BHQ-2), and the fluorescent reporter molecular was positioned so as to have a certain distance.

Primer information and target sequence information which is amplified and generated are as follows.

Primer 85:
(SEQ ID. NO: 204)
5'-ACGAGGCCTGTCCGCTTACTAG*CCAGGCTGGTCCTCATCCAACAG

CTCTTCTATCGC-3'

Primer86:
(SEQ ID. NO: 205)
5'-CCGGGTACGCTAAGTCCGCTAT*CCAGGTTCTGGTCCTCATCCAAC

AGCTCTTCTATCGT-3'

Primer 87:
(SEQ ID. NO: 206)
5'-GACCCATGGGACTCIGGAGAGCGTGAA-3'

Primer 88:
(SEQ ID. NO: 207)
5'-GCTCATATGCGGCGCCATTTA*CCAGGGCAGGTTGCTATCAAGGTT

ACAAGACAG-3'

Primer 89:
(SEQ ID. NO: 208)
5'-CCGAGCACTTTCTTGCCATGAGCC-3'

SCO 44:
(SEQ ID. NO: 209)
GTAGCACGCTTCGAATGGC[T(HEX)]ATACGAGGCCTGTCCGCTTACT

AG[BHQ1]

SCO 45:
(SEQ ID. NO: 210)
GATACGGAGGTCCGAAGGCAG[T(FAM)]GTTGGTTACCCTAACGCGCC

GGA[BHQ1]

SCO 46:
(SEQ ID. NO: 211)
ATTAGTTTAACTATTATATT[T(FAM)]TATGCTCATATGCGGCGCCAT

TTA[BHQ1]

Amplified product 43: GenBank: NT_009237.19/Position (start-end): 27598340-27598451

(SEQ ID. NO: 212)
ACGAGGCCTGTCCGCTTACTAG* CCAGGCTGGTCCTCATCCAACAGC

TCTTCTATCACGTGTTCGAAAGTGTCAGCCAATGATGTCAAGCCTCTTG

AACCTGCCTTGGGCCCATTCACGCTCTCCAGAGTCCCATGGGTC

Amplified product 44: GenBank: NT_009237.19/Position (start-end): 27598338-27598451

(SEQ ID. NO: 213)
CCGGGTACGCTAAGTCCGCTAT* CCAGGTTCTGGTCCTCATCCAAC

AGCTCTTCTATCACGTGTTCGAAAGTGTCAGCCAATGATGTCAAGCCTC

TTGAACCTGCCTTGGGCCCATTCACGCTCTCCAGAGTCCCATGGGTC

Amplified product 45: GenBank: EF450778.1/Position (start-end): 431-681

(SEQ ID. NO: 214)
GCTCATATGCGGCGCCATTTA* CCAGGGCAGGTTGCTATCAAGGTTA

CAAGACAGGTTTAAGGAGACCAATAGAAACTGGGCATGTGGAGACAGAG

AAGACTCTTGGGTTTCTGATAGGCACTGACTCTCTCTGCCTATTGGTCT

ATTTTCCCACCCTTAGGCTGCTGGTGGTGGTCTACCCTTGGACCCAGAG

GTTCTTTGAGTCCTTTGGGGATCTGTCCACTCCTGATGCTGTTATGGGC

AACCCTAAGGTGAAGGCTCATGGCAAGAAAGTGCTCGG

The bold and slanted font of the Primer sequence means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. The sequence of the CCTF produced from the amplified product is as follows.

```
CCTF 44:
                              (SEQ ID. NO: 215)
5'-CTAGTAAGCGGACAGGCCTCGT-3'

CCTF 45:
                              (SEQ ID. NO: 216)
5'-ATAGCGGACTTAGCGTACCCGG-3'

CCTF 46:
                              (SEQ ID. NO: 217)
5'-TAAATGGCGCCGCATATGAG-3'
```

2) PCR Amplification and Determination of SCO Inherent Dissociation

PCR reaction was performed using the following CFX96 Real-time PCR (Bio-Rad, USA) with 20 μl of total reaction solution of each of Primer 85, 86, 87, 88, 89 and SCO 44, 45,46 prepared by adding 0.15 μM, PspGI (NEB, USA) 5U, PCR buffer (1×), MgCl₂ 2.5 mM, dNTP 200 μM, h-Taq DNA polymerase (Solgent, Korea) 1.6 U and Flu A/H1N1. Flu A/H3N2, Flu A/H1N1/2009pdm, the template nucleic acids of the genomic RNA of Flu B, PIV1, PIV3, RSV A, RSV B, hMPV, ADV and MS2 phage 1×10⁻⁴ copies/rxn, respectively. 95° C. 15 mins, 95° C. 30 secs, 63° C. 1 min (50 cycles).

A reaction was performed using a cycle at the denaturation temperature of 95° C. for 15 minutes once, and with a cycle at the denaturation temperature of 95° C. for 30 seconds, and an annealing temperature of 63° C. for 1 minute 50 times repeatedly. After the reaction, the reaction mixture was cooled to 50° C. in the same apparatus, held at 50° C. for 30 seconds, and then slowly heated from 50° C. to 95° C. to obtain an inherent dissociation temperature analysis curve. Data analysis was performed with Bio-Rad CFX Manager 1.6.

FIG. 7 (a) shows the results of multiple inherent dissociation temperature measurements for the genotype of mutant type A/A, wild type G/G and heterozygote A/G of rs6265 and IC. It was identified that the peak was observed at the inherent dissociation temperature that each SCO has (A/A: 76.5° C., A/G: 76.5° C. ≠ 75° C., G/G 75° C., IC: 66° C.) (a)(b)(c)(d), and no peak of SCO visualizing CCTF was observed when the target sequence was not added in the same composition (e).

Therefore, it was proved that the target nucleic acid sequence can be detected more quickly and simply than the conventional PCR method by analyzing the fluorescence of the SCO using the real-time PCR instrument, simultaneously with the PCR using the marking technique of CCTF.

Example 3. Formation of CCTF and Analysis for Ct Graph of CCTF in Multiple Target PCR It has been proved in Example 2 that SCO can be used to confirm whether CCTF is generated with a real-time PCR device. The SCO used in the above method is simultaneously formed during the reaction in which the target sequence is generated during the PCR amplification process, and it is possible to identify CCTF generated by real-time fluorescence analysis. Based on this, the present example demonstrated that a standard curve formation is possible when analyzing the formation of CCTF using SCO in the case of PCR with multiple target sequences.

In order to perform this experiment, the causative organisms of sexually transmitted infections (STI), *Neisseria. gonorrhea* (NG), *Mycoplasma. hominis* (MH), *Ureaplasma. parvum* (UP) were selected.

1. Construction of Specific Primer of Target Template DNA

The forward primer used in this example was constructed based on the method described in the detailed description of the invention above as CPTO. The 5'end of the forward primer was composed of a 19-mer or 21-mer nucleotide sequence, and was composed of non-complementary sequences to DNA of each causative organism so as to form CCTF. The restriction enzyme recognition sequence was then consecutively located. After this up to the 3' end, a sequence complementary to DNA of each causative organism was composed to play a role as a primer. The reverse primer was composed of sequence complementary to the target site of DNA by each causative organism.

In addition, SCO, which forms a dimer with CCTF, was designed to have a double tag, and was separately designed for each causative organism. SCO was designed by positioning quencher (BHQ-1 or BHQ-2) at 3 end, with reporter molecular (each FAM, HEX, CAL Fluor Red 610) positioned at a certain distance, and its sequence was complementary to CCTF sequence to be analyzed.

Primer information and target sequence information which is amplified and generated are as follows.

```
Primer 90:
                                            (SEQ ID. NO: 218)
5'-CTCATCGCCACGAGCCGGTTAA *CCAGG*TTGAAACACCGCCCGGAA
CCC-3'

Primer 91:
                                            (SEQ ID. NO: 219)
5'-GCTCCTTATTCGGTTTGACCGGT-3'

Primer 92:
                                            (SEQ ID. NO: 220)
5'-GCTCGCAGGTACGGCACCATTCA *CCAGG*CAGAAGGTATGATAACA
ACGGTAGAGC-3'

Primer 93:
                                            (SEQ ID. NO: 221)
5'-CCCCTTTGCACCGTTGAGGGG-3'

Primer 94:
                                            (SEQ ID. NO: 222)
5'-AGTCGATTATGTCTGAGGCCGCG *CCAGG*TTAAAGTAGCATATGA
TCAAGCTCATTCA-3'

Primer 95:
                                            (SEQ ID. NO: 223)
5'-GATCCTGACATATAATCATTATCTCCTTTTATAAA-3'

SCO 47:
                                            (SEQ ID. NO: 224)
TC[T(HEX)]CATCGCCACGAGCCGGTTAA[BHQ]

SCO 48:
                                            (SEQ ID. NO: 225)
TG[T(CAL Fluor Red 610)]CGCAGGTACGGCACCATTCA[BHQ2]

SCO 49:
                                            (SEQ ID. NO: 226)
TAG[T(FAM)]CGATTATGTCTGAGGCCGCG[BHQ]
```

Amplified product 46: GenBank: X52364.1/Position (start-end): 375-459

```
                                            (SEQ ID. NO: 227)
CTCATCGCCACGAGCCGGTTAA *CCAGG*TTGAAACACCGCCCGGAAC

CCGATATAATCCGCCCTTCAACATCAGTGAAAATCTTTTTTTAACCGGT

CAAACCGAATAAGGAGC
```

Amplified product 47: GenBank: M31431.1/Position (start-end): 1455-1535

```
                                            (SEQ ID. NO: 228)
GCTCGCAGGTACGGCACCATTCA *CCAGG*CAGAAGGTATGATAACAA

CGGTAGAGCTTTATATGATATTAACTTAGCAAAAATGGAAAACCCCTCA

ACGGTGCAAAGGGG
```

Amplified product 48: GenBank: AF085733.2/Position (start-end): 416-502

```
                                            (SEQ ID. NO: 229)
AGTCGATTATGTCTGAGGCCGCG *CCAGG*GTTTCTGTACACGATCC

AATT[T/c]ACAAATAACATTTACAATTCGTAAAATTTTTTTATAAAAG

GAGATAATGATTATATGTCAGGATC
```

The bold and slanted font of the Primer sequence means the restriction enzyme recognition sequence, and the underline is the complementary sequence of the CCTF produced thereby. the part represented by * is a tag that modified dCTP was inserted into C in the recognition sequence to block the site cleaved by the PspGI restriction enzyme. In SCO, the parentheses mean the position of the nucleotide sequence in which the fluorescent offsetting molecule and the fluorescent reporter are located. Primer and primer corresponding to NG in SCO is the same as those used in Example 2. The sequence of the CCTF produced from the amplified product is as follows.

```
CCTF 47:
                                            (SEQ ID. NO: 230)
5'-CCTGGTTAACCGGCTCGTGGCGATGAG-3'

CCTF 48:
                                            (SEQ ID. NO: 231)
5'-CCTGGTGAATGGTGCCGTACCTGCGAGC-3'

CCTF 49:
                                            (SEQ ID. NO: 232)
5'-CCTGGCGCGGCCTCAGACATAATCGACT-3'
```

2. PCR Amplification and Determination of SCO Inherent Dissociation

PCR reaction was performed using the following CFX96 Real-time PCR (Bio-Rad, USA) with 20 μl of total reaction solution obtained by adding three kinds of the specific forward primers and three kinds of reverse primers of each target sequence, as mentioned in the above primer design, and three kinds of SCO to be 0.15 μM, respectively, and adding PspGI (NEB, USA) 2 U, PCR buffer (1×), $MgCl_2$ 2.5 mM, dNTP 200 μM, h-Taq DNA polymerase (Solgent, Korea) 1.6 U, and contained the template DNA diluted by 10-folds with 100 pg/μl genomic DNA proven by the conventional quantitation method for each causative organism.

95° C. 15 mins,
95° C. 30 secs, 63° C. 1 min (50 cycles).

A reaction was repeatedly performed with a cycle at the denaturation temperature of 95° C. for 15 minutes once, and with a cycle at the denaturation temperature of 95° C. for 30 seconds, and an annealing temperature of 63° C. for 1 minute 50 times. In addition, fluorescence signals were collected at the annealing stage, and the data analysis was performed with Bio-Rad CFX Manager 1.6. Cycle threshold (Ct) was started with an algebraic amplifier using a known number of DNA concentrations to create a standard curve for the strain.

As shown in (a) of FIG. 8, the expected fluorescence amplification curves of SCO could be observed with each of different graphs depending on the concentration of the template. Also, any peak was observed when the template DNA was not added (b). As the results showing fluorescence amplification curves and standards of SCO represented by the experimental condition of Polymerase Chain Reaction of NO (solid line), MG (dotted line), and UP (circle), dilutions for genomic DNA of each causative organism diluted by 10-folds starting from the concentration of 100 pg, graph (a) indicates the fluorescence amplification curve drawn when the three target sequences are present at the same time by the concentration, graph (b) is the negative result drawn when all three target sequences are not included. When the graph corresponding to NO in graph (a) is represented by the single fluorescence amplification curve and thus the standard curve, it can be represented by (c) and (d), respectively. The graph corresponding to MG can be expressed by (e) and (f), respectively, and the curve corresponding to UP can be represented by (g) and (h), respectively.

Regression coefficient ($r^2$) in the linear regression analysis of the standard curve was represented by NO 0.9982, MG 0.999, UP 0.9992, respectively. The slope of the regression plot was NG −3.85, MG −3.89, and UP −3.66, respectively. It could be identified that the respective amplification efficiency ($E=10^{[-1/slope]}-1$) was 81.8% for NO, 80.7% for MG and 87.6% for UP, respectively, and thus, they were listed in the proper range of between 80 and 120%.

From this Example, when reading the different CCTFs by each of causal organisms using the real-time PCR instrument, it was demonstrated that the relative amount of CCTF to be generated by measuring a degree of the real-time fluorescence of SCO is grasped, and by using this, the Ct value is confirmed, and therefore, the identifying of the target sequence is possible.

The invention claimed is:

1. A primer comprising:
a random nucleic acid sequence non-complementary to a target sequence, having 5 to 50 nucleotides in length, wherein the random sequence is located at the 5'end of the primer;
a restriction enzyme recognition sequence; and
a nucleic acid sequence complementary to the target sequence, wherein the primer comprises one sequence selected from the group consisting of SEQ ID NOs: 1, 3, 9, 11, 13, 15, 17, 19, 21, 23, 25, 27, 29, 31, 33, 74, 76, 78, 80, 82, 84, 86, 115, 117, 119, 121, 123, 125, 127, 129, 131, 151, 153, 155, 156, 159, 161, 163, 164, 166, 168, 170, 204, 205, 207, 218, 220 and 222.

* * * * *

```
                              SEQUENCE LISTING

<160> NUMBER OF SEQ ID NOS: 232

<210> SEQ ID NO 1
    <211> LENGTH: 47
    <212> TYPE: DNA
    <213> ORGANISM: Artificial Sequence
    <220> FEATURE:
    <223> OTHER INFORMATION: primer

<400> SEQUENCE: 1
tgaactatcc tggtccgacg tttcggttgt gttgaaacac cgcccgg              47

<210> SEQ ID NO 2
    <211> LENGTH: 22
    <212> TYPE: DNA
    <213> ORGANISM: Artificial Sequence
    <220> FEATURE:
    <223> OTHER INFORMATION: primer

<400> SEQUENCE: 2
gctccttatt cggtttgacc gg                                         22

<210> SEQ ID NO 3
    <211> LENGTH: 41
    <212> TYPE: DNA
    <213> ORGANISM: Artificial Sequence
    <220> FEATURE:
    <223> OTHER INFORMATION: primer

<400> SEQUENCE: 3
atctatgata cctggtttag ctcctattgc caacgtattg g                    41

<210> SEQ ID NO 4
    <211> LENGTH: 28
    <212> TYPE: DNA
    <213> ORGANISM: Artificial Sequence
    <220> FEATURE:
    <223> OTHER INFORMATION: primer

<400> SEQUENCE: 4
tgtgtggagc atcttgtaat ctttggtc                                   28

<210> SEQ ID NO 5
    <211> LENGTH: 117
    <212> TYPE: DNA
    <213> ORGANISM: Artificial Sequence
    <220> FEATURE:
    <223> OTHER INFORMATION: product

<400> SEQUENCE: 5
tgaactatcc tggtccgacg tttcggttgt gttgaaacac cgcccggaac ccgatataat    60
ccgcccttca acatcagtga aaatcttttt tttaaccggt caaaccgaat aaggagc     117

<210> SEQ ID NO 6
    <211> LENGTH: 125
    <212> TYPE: DNA
    <213> ORGANISM: Artificial Sequence
    <220> FEATURE:
    <223> OTHER INFORMATION: product
```

```
<400> SEQUENCE: 6
atctatgata cctggtttag ctcctattgc caacgtattg gaaaaaaact ttggtattga    60
aaaaggattt atgacaacag tccactcata tacagcagac caaagattac aagatgctcc   120
acaca                                                               125

<210> SEQ ID NO 7
<211> LENGTH: 13
<212> TYPE: DNA
<213> ORGANISM: Artificial Sequence
<220> FEATURE:
<223> OTHER INFORMATION: CCTF

<400> SEQUENCE: 7
ccaggatagt tca                                                       13

<210> SEQ ID NO 8
<211> LENGTH: 15
<212> TYPE: DNA
<213> ORGANISM: Artificial Sequence
<220> FEATURE:
<223> OTHER INFORMATION: CCTF

<400> SEQUENCE: 8
ccaggtatca tagat                                                     15

<210> SEQ ID NO 9
<211> LENGTH: 47
<212> TYPE: DNA
<213> ORGANISM: Artificial Sequence
<220> FEATURE:
<223> OTHER INFORMATION: primer

<400> SEQUENCE: 9
ccactccagc cggctgacac caggacttgg tgtgacgcta tcagcat                  47

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
gttttcaaaa cacggtcgaa aacaaagtc                                      29

<210> SEQ ID NO 11
<211> LENGTH: 46
<212> TYPE: DNA
<213> ORGANISM: Artificial Sequence
<220> FEATURE:
<223> OTHER INFORMATION: primer

<400> SEQUENCE: 11
catcgccacg agccggttaa ccaggttgaa acaccgcccg gaaccc                   46

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
gctccttatt cggtttgacc ggt                                            23
```

```
<210> SEQ ID NO 13
<211> LENGTH: 51
<212> TYPE: DNA
<213> ORGANISM: Artificial Sequence
<220> FEATURE:
<223> OTHER INFORMATION: primer

<400> SEQUENCE: 13
actcacgcta atggagcgca ccaggtttag ctcctattgc caacgtattg g          51

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
tgtgtggagc atcttgtaat ctttggtc                                    28

<210> SEQ ID NO 15
<211> LENGTH: 52
<212> TYPE: DNA
<213> ORGANISM: Artificial Sequence
<220> FEATURE:
<223> OTHER INFORMATION: primer

<400> SEQUENCE: 15
gctacccagc cggctacaag ccaggcttta tggtgcttat attggtggca tg         52

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
ctgtataacg ttgtgcagca ggtc                                        24

<210> SEQ ID NO 17
<211> LENGTH: 47
<212> TYPE: DNA
<213> ORGANISM: Artificial Sequence
<220> FEATURE:
<223> OTHER INFORMATION: primer

<400> SEQUENCE: 17
tgccgcgtga ttcgatccca ccaggtatgt ccggcacaac atgcgct               47

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
gagcttacga aggtcggagt tga                                         23

<210> SEQ ID NO 19
<211> LENGTH: 51
<212> TYPE: DNA
<213> ORGANISM: Artificial Sequence
<220> FEATURE:
<223> OTHER INFORMATION: primer
```

<400> SEQUENCE: 19
tctcatagct gggccgctgc caggaagtag catatgatga agcacacaac a     51

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
taatgcaacg tgcatttgct tcaac     25

<210> SEQ ID NO 21
<211> LENGTH: 55
<212> TYPE: DNA
<213> ORGANISM: Artificial Sequence
<220> FEATURE:
<223> OTHER INFORMATION: primer

<400> SEQUENCE: 21
cagatcgttg gcactctgcg accaggttaa agtagcatat gatcaagctc attca     55

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22
ttgtaatgat acaacgagca tcatcattaa t     31

<210> SEQ ID NO 23
<211> LENGTH: 51
<212> TYPE: DNA
<213> ORGANISM: Artificial Sequence
<220> FEATURE:
<223> OTHER INFORMATION: primer

<400> SEQUENCE: 23
gctcgtatgc cgctccatat accaggccaa atctggatct tcctctgcat c     51

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
gagcttgagc tggacccaga g     21

<210> SEQ ID NO 25
<211> LENGTH: 48
<212> TYPE: DNA
<213> ORGANISM: Artificial Sequence
<220> FEATURE:
<223> OTHER INFORMATION: primer

<400> SEQUENCE: 25
acgtgccgtg catcgttgca ccaggcaacc ggctccattt tggtggag     48

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
cgtcacgtcc ttcatcggtc c                                            21

<210> SEQ ID NO 27
<211> LENGTH: 46
<212> TYPE: DNA
<213> ORGANISM: Artificial Sequence
<220> FEATURE:
<223> OTHER INFORMATION: primer

<400> SEQUENCE: 27
tcgcagtccc gtcgaggaac caggaggcct ggctatccgg agaaac                 46

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cgttgtgttg gccgcaggtc                                              20

<210> SEQ ID NO 29
<211> LENGTH: 44
<212> TYPE: DNA
<213> ORGANISM: Artificial Sequence
<220> FEATURE:
<223> OTHER INFORMATION: primer

<400> SEQUENCE: 29
ctcatagcta ggcgcctgcc agggctgcac gtgggtctgt tgtg                   44

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ggaaacgcag gccacgaaac c                                            21

<210> SEQ ID NO 31
<211> LENGTH: 50
<212> TYPE: DNA
<213> ORGANISM: Artificial Sequence
<220> FEATURE:
<223> OTHER INFORMATION: primer

<400> SEQUENCE: 31
gcttcgcgtc tcaggcctgt ccaggggca ttacagtttt gcgtcatgac              50

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
caagtctgag cacttgcacc g                                             21

<210> SEQ ID NO 33
<211> LENGTH: 47
<212> TYPE: DNA
<213> ORGANISM: Artificial Sequence
<220> FEATURE:
<223> OTHER INFORMATION: primer

<400> SEQUENCE: 33
ctgttagctc tgcgagctcc aggggagcga cacttgttgg tgttgac                 47

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
tgatgaaatg aagccacccg tgc                                           23

<210> SEQ ID NO 35
<211> LENGTH: 41
<212> TYPE: DNA
<213> ORGANISM: Artificial Sequence
<220> FEATURE:
<223> OTHER INFORMATION: SCO

<400> SEQUENCE: 35
tcggagccag cgcggcgtaa acccactcca gccggctgac a                       41

<210> SEQ ID NO 36
<211> LENGTH: 44
<212> TYPE: DNA
<213> ORGANISM: Artificial Sequence
<220> FEATURE:
<223> OTHER INFORMATION: SCO

<400> SEQUENCE: 36
tacaacagca gtacggagac gactcatcgc cacgagccgg ttaa                    44

<210> SEQ ID NO 37
<211> LENGTH: 44
<212> TYPE: DNA
<213> ORGANISM: Artificial Sequence
<220> FEATURE:
<223> OTHER INFORMATION: SCO

<400> SEQUENCE: 37
atttattctt actcgatgtt aaatactcac gctaatggag cgca                    44

<210> SEQ ID NO 38
<211> LENGTH: 43
<212> TYPE: DNA
<213> ORGANISM: Artificial Sequence
<220> FEATURE:
<223> OTHER INFORMATION: SCO

<400> SEQUENCE: 38
tatatatata tattattata aatgctaccc agccggctac aag                     43

```
<210> SEQ ID NO 39
<211> LENGTH: 44
<212> TYPE: DNA
<213> ORGANISM: Artificial Sequence
<220> FEATURE:
<223> OTHER INFORMATION: SCO

<400> SEQUENCE: 39
aagaataact actacaatct actttgccgc gtgattcgat ccca             44

<210> SEQ ID NO 40
<211> LENGTH: 42
<212> TYPE: DNA
<213> ORGANISM: Artificial Sequence
<220> FEATURE:
<223> OTHER INFORMATION: SCO

<400> SEQUENCE: 40
ttattattat tattattata tattctcata gctgggccgc tg               42

<210> SEQ ID NO 41
<211> LENGTH: 42
<212> TYPE: DNA
<213> ORGANISM: Artificial Sequence
<220> FEATURE:
<223> OTHER INFORMATION: SCO

<400> SEQUENCE: 41
aatcttcaat gcttaccgta tcagatcgtt ggcactctgc ga               42

<210> SEQ ID NO 42
<211> LENGTH: 42
<212> TYPE: DNA
<213> ORGANISM: Artificial Sequence
<220> FEATURE:
<223> OTHER INFORMATION: SCO

<400> SEQUENCE: 42
aaaataaata atataatata tgctcgtatg ccgctccata ta               42

<210> SEQ ID NO 43
<211> LENGTH: 43
<212> TYPE: DNA
<213> ORGANISM: Artificial Sequence
<220> FEATURE:
<223> OTHER INFORMATION: SCO

<400> SEQUENCE: 43
tcggagccag cgcggcgtaa cgtacgtgcc gtgcatcgtt gca              43

<210> SEQ ID NO 44
<211> LENGTH: 43
<212> TYPE: DNA
<213> ORGANISM: Artificial Sequence
<220> FEATURE:
<223> OTHER INFORMATION: SCO

<400> SEQUENCE: 44
aagaataact actacaatct actttcgcag tcccgtcgag gaa              43

<210> SEQ ID NO 45
<211> LENGTH: 41
<212> TYPE: DNA
<213> ORGANISM: Artificial Sequence
<220> FEATURE:
<223> OTHER INFORMATION: SCO
```

<400> SEQUENCE: 45
tcggagccag cgcggcgtaa tctctcatag ctaggcgcct g                          41

<210> SEQ ID NO 46
<211> LENGTH: 41
<212> TYPE: DNA
<213> ORGANISM: Artificial Sequence
<220> FEATURE:
<223> OTHER INFORMATION: SCO

<400> SEQUENCE: 46
aaaataaata atataatata gtcttcgcgt ctcaggcctg t                          41

<210> SEQ ID NO 47
<211> LENGTH: 40
<212> TYPE: DNA
<213> ORGANISM: Artificial Sequence
<220> FEATURE:
<223> OTHER INFORMATION: SCO

<400> SEQUENCE: 47
aaaataaata atataatata ttctgttagc tctgcgagct                            40

<210> SEQ ID NO 48
<211> LENGTH: 95
<212> TYPE: DNA
<213> ORGANISM: Artificial Sequence
<220> FEATURE:
<223> OTHER INFORMATION: product

<400> SEQUENCE: 48
ccactccagc cggctgacac caggacttgg tgtgacgcta tcagcatgcg tatgggttac      60
tatggtgact ttgttttcga ccgtgttttg aaaac                                 95

<210> SEQ ID NO 49
<211> LENGTH: 122
<212> TYPE: DNA
<213> ORGANISM: Artificial Sequence
<220> FEATURE:
<223> OTHER INFORMATION: product

<400> SEQUENCE: 49
cgcccaccgc atcccgcgcc cctccctcag caccaggttg aaacaccgcc cggaacccga      60
tataatccgc ccttcaacat cagtgaaaat cttttttttaa ccggtcaaac cgaataagga    120
gc                                                                    122

<210> SEQ ID NO 50
<211> LENGTH: 135
<212> TYPE: DNA
<213> ORGANISM: Artificial Sequence
<220> FEATURE:
<223> OTHER INFORMATION: product

<400> SEQUENCE: 50
actcacgcta atggagcgca ccaggtttag ctcctattgc caacgtattg gaaaaaaact      60
ttggtattga aaaggatttt atgacaacag tccactcata tacagcagac caaagattac    120
aagatgctcc acaca                                                      135

<210> SEQ ID NO 51
<211> LENGTH: 251
<212> TYPE: DNA
<213> ORGANISM: Artificial Sequence
<220> FEATURE:
<223> OTHER INFORMATION: product

<400> SEQUENCE: 51

```
gctacccagc cggctacaag ccaggctttta tggtgcttat attggtggca tgcaccatga    60
tcgtcctttt aaaaagtctg cgaggattgt tggtgatgta atgagtaaat tccaccctca   120
tggtgatatg gcaatatatg acaccatgtc aagaatggct caagactttt cattaagata   180
ccttttaatt gatggtcatg gtaattttgg ttctatagat ggtgatagac ctgctgcaca   240
acgttataca g                                                        251
```

<210> SEQ ID NO 52
<211> LENGTH: 111
<212> TYPE: DNA
<213> ORGANISM: Artificial Sequence
<220> FEATURE:
<223> OTHER INFORMATION: product

<400> SEQUENCE: 52

```
tgccgcgtga ttcgatccca ccaggtatgt ccggcacaac atgcgcttat gtccggcaca    60
acatgcgctc tccgcttccc aggtcagctc aactccgacc ttcgtaagct c            111
```

<210> SEQ ID NO 53
<211> LENGTH: 225
<212> TYPE: DNA
<213> ORGANISM: Artificial Sequence
<220> FEATURE:
<223> OTHER INFORMATION: product

<400> SEQUENCE: 53

```
tctcatagct gggccgctgc caggaagtag catatgatga agcacacaac aaaatggcgc    60
atactgtgta tttcactaat ttctatcgtt catcaaaacc actatttta gatgaagaag   120
acccaattaa tccctgtttt caaactatta gtatgggtgg gggttatgta tctggtgaag   180
tgtatcgttc tgattttgaa gttgaagcaa atgcacgttg catta                   225
```

<210> SEQ ID NO 54
<211> LENGTH: 236
<212> TYPE: DNA
<213> ORGANISM: Artificial Sequence
<220> FEATURE:
<223> OTHER INFORMATION: product

<400> SEQUENCE: 54

```
cagatcgttg gcactctgcg accaggttaa agtagcatat gatcaagctc attcaaaaat    60
ggcacatact gtctatttta cgaatttta tcgttcatct aaaccttttat ttttagatga   120
agaagatcca atcaacccct gttttcaaac aattagtatg ggtggtggat atgtttcagg   180
tgaaatttat cgttctgatt ttgaaattaa tgatgatgct cgttgtatca ttacaa       236
```

<210> SEQ ID NO 55
<211> LENGTH: 102
<212> TYPE: DNA
<213> ORGANISM: Artificial Sequence
<220> FEATURE:
<223> OTHER INFORMATION: product

<400> SEQUENCE: 55

```
gctcgtatgc cgctccatat accaggccaa atctggatct tcctctgcat ctgcttctgg    60
atcatcaagc agcagcacca gctctgggtc cagctcaagc tc                      102
```

```
<210> SEQ ID NO 56
<211> LENGTH: 187
<212> TYPE: DNA
<213> ORGANISM: Artificial Sequence
<220> FEATURE:
<223> OTHER INFORMATION: product

<400> SEQUENCE: 56
acgtgccgtg catcgttgca ccaggcaacc ggctccattt tggtggagtc gcttgatcgt      60
tttgtgatcg tttagtgtga tgatttatta tgtctagaga gttaagcgat aggcttttac     120
tggtgtatca ctgtaagggc gtattggttg gatgccttgg tagacaggac cgatgaagga    180
cgtgacg                                                               187

<210> SEQ ID NO 57
<211> LENGTH: 172
<212> TYPE: DNA
<213> ORGANISM: Artificial Sequence
<220> FEATURE:
<223> OTHER INFORMATION: product

<400> SEQUENCE: 57
tcgcagtccc gtcgaggaac caggaggcct ggctatccgg agaaacagca cacgacttgg      60
cgttctgtgt gtcgcgatgt ctctgcgcgc agtctggcat ctggggcttt tgggaagcct    120
cgtgggggct gttcttgccg ccacccatcg gggacctgcg gccaacacaa cg            172

<210> SEQ ID NO 58
<211> LENGTH: 209
<212> TYPE: DNA
<213> ORGANISM: Artificial Sequence
<220> FEATURE:
<223> OTHER INFORMATION: product

<400> SEQUENCE: 58
ctcatagcta ggcgcctgcc agggctgcac gtgggtctgt tgtgggtaga ggtgggcggg      60
gagggccccg ccccaccgc ccccccaca ggcggcgcgt gcggagggcg gcccgtgcgt      120
ccccccggtc cccgcgggcc gcccgtggcg ctcggtgccc ccggtatggt attccgcccc   180
caaccccggg tttcgtggcc tgcgtttcc                                       209

<210> SEQ ID NO 59
<211> LENGTH: 183
<212> TYPE: DNA
<213> ORGANISM: Artificial Sequence
<220> FEATURE:
<223> OTHER INFORMATION: product

<400> SEQUENCE: 59
gcttcgcgtc tcaggcctgt ccaggggggca ttacagtttt gcgtcatgac ggctttgaag     60
ctgacgacct cattgcaacc ctagcaaaac gagttgcggc tgagcactgt catgttgtga   120
ttatctcctc agataaagat gtacttcagc ttgtgtgtga tacggtgcaa gtgctcagac   180
ttg                                                                   183

<210> SEQ ID NO 60
<211> LENGTH: 183
<212> TYPE: DNA
<213> ORGANISM: Artificial Sequence
<220> FEATURE:
<223> OTHER INFORMATION: product
```

<400> SEQUENCE: 60
ctgttagctc tgcgagctcc aggggagcga cacttgttgg tgttgacaag ttcggtaaca    60
aatactacca gaagctaggc gatactcaat acggtatgca cagatgggta gagtatgctt   120
caaaggatcg ttacaacgca tctcaagtac cagctgaatg gcacgggtgg cttcatttca   180
tca                                                                 183

<210> SEQ ID NO 61
<211> LENGTH: 24
<212> TYPE: DNA
<213> ORGANISM: Artificial Sequence
<220> FEATURE:
<223> OTHER INFORMATION: CCTF

<400> SEQUENCE: 61
cctggtgtca gccggctgga gtgg                                           24

<210> SEQ ID NO 62
<211> LENGTH: 25
<212> TYPE: DNA
<213> ORGANISM: Artificial Sequence
<220> FEATURE:
<223> OTHER INFORMATION: CCTF

<400> SEQUENCE: 62
cctggttaac cggctcgtgg cgatg                                          25

<210> SEQ ID NO 63
<211> LENGTH: 25
<212> TYPE: DNA
<213> ORGANISM: Artificial Sequence
<220> FEATURE:
<223> OTHER INFORMATION: CCTF

<400> SEQUENCE: 63
cctggtgcgc tccattagcg tgagt                                          25

<210> SEQ ID NO 64
<211> LENGTH: 25
<212> TYPE: DNA
<213> ORGANISM: Artificial Sequence
<220> FEATURE:
<223> OTHER INFORMATION: CCTF

<400> SEQUENCE: 64
cctggcttgt agccggctgg gtagc                                          25

<210> SEQ ID NO 65
<211> LENGTH: 25
<212> TYPE: DNA
<213> ORGANISM: Artificial Sequence
<220> FEATURE:
<223> OTHER INFORMATION: CCTF

<400> SEQUENCE: 65
cctggtggga tcgaatcacg cggca                                          25

<210> SEQ ID NO 66
<211> LENGTH: 24
<212> TYPE: DNA
<213> ORGANISM: Artificial Sequence
<220> FEATURE:
<223> OTHER INFORMATION: CCTF

<400> SEQUENCE: 66
cctggcagcg gcccagctat gaga                                          24

<210> SEQ ID NO 67
<211> LENGTH: 26
<212> TYPE: DNA
<213> ORGANISM: Artificial Sequence
<220> FEATURE:
<223> OTHER INFORMATION: CCTF

<400> SEQUENCE: 67
cctggtcgca gagtgccaac gatctg                                        26

<210> SEQ ID NO 68
<211> LENGTH: 26
<212> TYPE: DNA
<213> ORGANISM: Artificial Sequence
<220> FEATURE:
<223> OTHER INFORMATION: CCTF

<400> SEQUENCE: 68
cctggtatat ggagcggcat acgagc                                        26

<210> SEQ ID NO 69
<211> LENGTH: 25
<212> TYPE: DNA
<213> ORGANISM: Artificial Sequence
<220> FEATURE:
<223> OTHER INFORMATION: CCTF

<400> SEQUENCE: 69
cctggtgcaa cgatgcacgg cacgt                                         25

<210> SEQ ID NO 70
<211> LENGTH: 24
<212> TYPE: DNA
<213> ORGANISM: Artificial Sequence
<220> FEATURE:
<223> OTHER INFORMATION: CCTF

<400> SEQUENCE: 70
cctggttcct cgacgggact gcga                                          24

<210> SEQ ID NO 71
<211> LENGTH: 23
<212> TYPE: DNA
<213> ORGANISM: Artificial Sequence
<220> FEATURE:
<223> OTHER INFORMATION: CCTF

<400> SEQUENCE: 71
cctggcaggc gcctagctat gag                                           23

<210> SEQ ID NO 72
<211> LENGTH: 25
<212> TYPE: DNA
<213> ORGANISM: Artificial Sequence
<220> FEATURE:
<223> OTHER INFORMATION: CCTF

<400> SEQUENCE: 72
cctggacagg cctgagacgc gaagc                                         25

<210> SEQ ID NO 73
<211> LENGTH: 23
<212> TYPE: DNA
<213> ORGANISM: Artificial Sequence
<220> FEATURE:
<223> OTHER INFORMATION: CCTF

<400> SEQUENCE: 73
cctggagctc gcagagctaa cag                                       23

<210> SEQ ID NO 74
<211> LENGTH: 53
<212> TYPE: DNA
<213> ORGANISM: Artificial Sequence
<220> FEATURE:
<223> OTHER INFORMATION: primer

<400> SEQUENCE: 74
gcaggagcct ctcatctcgc caggctcatt tatagacarc ttctcactaa ttc      53

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
agttttttct gatccaatyt gytctatttc                                30

<210> SEQ ID NO 76
<211> LENGTH: 49
<212> TYPE: DNA
<213> ORGANISM: Artificial Sequence
<220> FEATURE:
<223> OTHER INFORMATION: primer

<400> SEQUENCE: 76
tcagacggtt cgaggctccc caggargaty aagcgtggag tatayatgg           49

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
tttgcgtgcy tcttcacacg c                                         21

<210> SEQ ID NO 78
<211> LENGTH: 46
<212> TYPE: DNA
<213> ORGANISM: Artificial Sequence
<220> FEATURE:
<223> OTHER INFORMATION: primer

<400> SEQUENCE: 78
aacgcgaatc gaccggatcc aggcgcgatg tgtttgccga taaaac              46

<210> SEQ ID NO 79
<211> LENGTH: 20
<212> TYPE: DNA
<213> ORGANISM: Artificial Sequence
<220> FEATURE:
<223> OTHER INFORMATION: primer

```
<400> SEQUENCE: 79
cattgcgtct gccccacttg                                              20

<210> SEQ ID NO 80
<211> LENGTH: 51
<212> TYPE: DNA
<213> ORGANISM: Artificial Sequence
<220> FEATURE:
<223> OTHER INFORMATION: primer

<400> SEQUENCE: 80
aacgcgaatc gaccggatcc aggaaacaag aacacctatg cctacatgaa c           51

<210> SEQ ID NO 81
<211> LENGTH: 27
<212> TYPE: DNA
<213> ORGANISM: Artificial Sequence
<220> FEATURE:
<223> OTHER INFORMATION: primer

<400> SEQUENCE: 81
atgttaacgt ccttcctgaa gttccac                                      27

<210> SEQ ID NO 82
<211> LENGTH: 46
<212> TYPE: DNA
<213> ORGANISM: Artificial Sequence
<220> FEATURE:
<223> OTHER INFORMATION: primer

<400> SEQUENCE: 82
tagatcggac tgcgaatcgc cagggagatc gcratctyct gcccga                 46

<210> SEQ ID NO 83
<211> LENGTH: 22
<212> TYPE: DNA
<213> ORGANISM: Artificial Sequence
<220> FEATURE:
<223> OTHER INFORMATION: primer

<400> SEQUENCE: 83
rgcgtcctta gacgccatca tc                                           22

<210> SEQ ID NO 84
<211> LENGTH: 49
<212> TYPE: DNA
<213> ORGANISM: Artificial Sequence
<220> FEATURE:
<223> OTHER INFORMATION: primer

<400> SEQUENCE: 84
atctacagcg tcgcatcacg ccaggcgcaa tctggctccc artttttgtg             49

<210> SEQ ID NO 85
<211> LENGTH: 22
<212> TYPE: DNA
<213> ORGANISM: Artificial Sequence
<220> FEATURE:
<223> OTHER INFORMATION: primer

<400> SEQUENCE: 85
gcgtcaytcg acgccatcyt ca                                           22
```

```
<210> SEQ ID NO 86
<211> LENGTH: 51
<212> TYPE: DNA
<213> ORGANISM: Artificial Sequence
<220> FEATURE:
<223> OTHER INFORMATION: primer

<400> SEQUENCE: 86
cataggtcga ggtcctcacc cagggcaaac tccggcatct actaatagac g          51

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
aagcggtgat ccgcacagtg                                             20

<210> SEQ ID NO 88
<211> LENGTH: 47
<212> TYPE: DNA
<213> ORGANISM: Artificial Sequence
<220> FEATURE:
<223> OTHER INFORMATION: SCO

<400> SEQUENCE: 88
tcggccgatc gtccatagag tcaagctcgc aggagcctct catctcg                47

<210> SEQ ID NO 89
<211> LENGTH: 45
<212> TYPE: DNA
<213> ORGANISM: Artificial Sequence
<220> FEATURE:
<223> OTHER INFORMATION: SCO

<400> SEQUENCE: 89
tcacgatgag cgagttgagc tacgtatcag acggttcgag gctcc                  45

<210> SEQ ID NO 90
<211> LENGTH: 43
<212> TYPE: DNA
<213> ORGANISM: Artificial Sequence
<220> FEATURE:
<223> OTHER INFORMATION: SCO

<400> SEQUENCE: 90
tgttcaatat ataatgataa tatgtaacgc gaatcgaccg gat                    43

<210> SEQ ID NO 91
<211> LENGTH: 43
<212> TYPE: DNA
<213> ORGANISM: Artificial Sequence
<220> FEATURE:
<223> OTHER INFORMATION: SCO

<400> SEQUENCE: 91
tgttcaatat ataatgataa tatgtaacgc gaatcgaccg gat                    43

<210> SEQ ID NO 92
<211> LENGTH: 42
<212> TYPE: DNA
<213> ORGANISM: Artificial Sequence
<220> FEATURE:
<223> OTHER INFORMATION: SCO
```

<400> SEQUENCE: 92
acatttataa tacagtattt tattagatcg gactgcgaat cg                           42

<210> SEQ ID NO 93
<211> LENGTH: 45
<212> TYPE: DNA
<213> ORGANISM: Artificial Sequence
<220> FEATURE:
<223> OTHER INFORMATION: SCO

<400> SEQUENCE: 93
agctcctgcc agtactgcca tccatatcta cagcgtcgca tcacg                        45

<210> SEQ ID NO 94
<211> LENGTH: 43
<212> TYPE: DNA
<213> ORGANISM: Artificial Sequence
<220> FEATURE:
<223> OTHER INFORMATION: SCO

<400> SEQUENCE: 94
tagttataat gaataactat tattcatagg tcgaggtcct cac                          43

<210> SEQ ID NO 95
<211> LENGTH: 105
<212> TYPE: DNA
<213> ORGANISM: Artificial Sequence
<220> FEATURE:
<223> OTHER INFORMATION: product

<400> SEQUENCE: 95
gcaggagcct ctcatctcgc caggctcatt tatagacarc ttctcactaa ttcatattca        60
gtagatttac atgatgaaat agarcaratt ggatcagaaa aaact                       105

<210> SEQ ID NO 96
<211> LENGTH: 114
<212> TYPE: DNA
<213> ORGANISM: Artificial Sequence
<220> FEATURE:
<223> OTHER INFORMATION: product

<400> SEQUENCE: 96
tcagacggtt cgaggctccc caggargaty aagcgtggag tatayatgga cctgcttgtc        60 tcggggggcaa gcccaggcaa tgcatggtcc catgcgtgtg aagargcacg caaa            114

<210> SEQ ID NO 97
<211> LENGTH: 82
<212> TYPE: DNA
<213> ORGANISM: Artificial Sequence
<220> FEATURE:
<223> OTHER INFORMATION: product

<400> SEQUENCE: 97
aacgcgaatc gaccggatcc aggcgcgatg tgtttgccga taaaacgtac caaccggagc        60
cccaagtggg gcagacgcaa tg                                                 82

<210> SEQ ID NO 98
<211> LENGTH: 308
<212> TYPE: DNA
<213> ORGANISM: Artificial Sequence
<220> FEATURE:
<223> OTHER INFORMATION: product

<400> SEQUENCE: 98

```
aacgcgaatc gaccggatcc aggaaacaag aacacctatg cctacatgaa cggtcgggtg    60
gcggttccta gcgccctcga tacctacgta aacatcgggg cacggtggtc tccagatccc   120
atggacaatg ttaaccccttt caatcaccac cgtaacgccg gtctgcgcta tcgatccatg   180
ctcttgggca acgggcgtta cgtacccttc cacattcaag tcccccagaa gttttttgcc   240
attaaaaatc tcctcctctt accgggttcc tacacctacg agtggaactt caggaaggac   300
gttaacat                                                            308
```

<210> SEQ ID NO 99
<211> LENGTH: 78
<212> TYPE: DNA
<213> ORGANISM: Artificial Sequence
<220> FEATURE:
<223> OTHER INFORMATION: product

<400> SEQUENCE: 99

```
tagatcggac tgcgaatcgc cagggagatc gcratctyct gcccgaattc gtaaatgatg    60
atggcgtcta aggacgcy                                                  78
```

<210> SEQ ID NO 100
<211> LENGTH: 73
<212> TYPE: DNA
<213> ORGANISM: Artificial Sequence
<220> FEATURE:
<223> OTHER INFORMATION: product

<400> SEQUENCE: 100

```
atctacagcg tcgcatcacg ccaggcgcaa tctggctccc arttttgtga atgargatgg    60
cgtcgartga cgc                                                       73
```

<210> SEQ ID NO 101
<211> LENGTH: 196
<212> TYPE: DNA
<213> ORGANISM: Artificial Sequence
<220> FEATURE:
<223> OTHER INFORMATION: product

<400> SEQUENCE: 101

```
cataggtcga ggtcctcacc cagggcaaac tccggcatct actaatagac gccggccatt    60
caaacatgag gattacccat gtcgaagaca acaaagaagt tcaactcttt atgtattgat   120
cttcctcgcg atctttctct cgaaatttac caatcaattg cttctgtcgc tactggaagc   180
ggtgatccgc acagtg                                                   196
```

<210> SEQ ID NO 102
<211> LENGTH: 24
<212> TYPE: DNA
<213> ORGANISM: Artificial Sequence
<220> FEATURE:
<223> OTHER INFORMATION: CCTF

<400> SEQUENCE: 102

```
cctggtgtca gccggctgga gtgg                                           24
```

<210> SEQ ID NO 103
<211> LENGTH: 25
<212> TYPE: DNA
<213> ORGANISM: Artificial Sequence
<220> FEATURE:
<223> OTHER INFORMATION: CCTF

```
<400> SEQUENCE: 103
cctggttaac cggctcgtgg cgatg                                        25

<210> SEQ ID NO 104
<211> LENGTH: 25
<212> TYPE: DNA
<213> ORGANISM: Artificial Sequence
<220> FEATURE:
<223> OTHER INFORMATION: CCTF

<400> SEQUENCE: 104
cctggtgcgc tccattagcg tgagt                                        25

<210> SEQ ID NO 105
<211> LENGTH: 25
<212> TYPE: DNA
<213> ORGANISM: Artificial Sequence
<220> FEATURE:
<223> OTHER INFORMATION: CCTF

<400> SEQUENCE: 105
cctggcttgt agccggctgg gtagc                                        25

<210> SEQ ID NO 106
<211> LENGTH: 25
<212> TYPE: DNA
<213> ORGANISM: Artificial Sequence
<220> FEATURE:
<223> OTHER INFORMATION: CCTF

<400> SEQUENCE: 106
cctggtggga tcgaatcacg cggca                                        25

<210> SEQ ID NO 107
<211> LENGTH: 24
<212> TYPE: DNA
<213> ORGANISM: Artificial Sequence
<220> FEATURE:
<223> OTHER INFORMATION: CCTF

<400> SEQUENCE: 107
cctggcagcg gcccagctat gaga                                         24

<210> SEQ ID NO 108
<211> LENGTH: 26
<212> TYPE: DNA
<213> ORGANISM: Artificial Sequence
<220> FEATURE:
<223> OTHER INFORMATION: CCTF

<400> SEQUENCE: 108
cctggtcgca gagtgccaac gatctg                                       26

<210> SEQ ID NO 109
<211> LENGTH: 26
<212> TYPE: DNA
<213> ORGANISM: Artificial Sequence
<220> FEATURE:
<223> OTHER INFORMATION: CCTF

<400> SEQUENCE: 109
cctggtatat ggagcggcat acgagc                                       26
```

```
<210> SEQ ID NO 110
<211> LENGTH: 25
<212> TYPE: DNA
<213> ORGANISM: Artificial Sequence
<220> FEATURE:
<223> OTHER INFORMATION: CCTF

<400> SEQUENCE: 110
cctggtgcaa cgatgcacgg cacgt                                          25

<210> SEQ ID NO 111
<211> LENGTH: 24
<212> TYPE: DNA
<213> ORGANISM: Artificial Sequence
<220> FEATURE:
<223> OTHER INFORMATION: CCTF

<400> SEQUENCE: 111
cctggttcct cgacgggact gcga                                           24

<210> SEQ ID NO 112
<211> LENGTH: 23
<212> TYPE: DNA
<213> ORGANISM: Artificial Sequence
<220> FEATURE:
<223> OTHER INFORMATION: CCTF

<400> SEQUENCE: 112
cctggcaggc gcctagctat gag                                            23

<210> SEQ ID NO 113
<211> LENGTH: 25
<212> TYPE: DNA
<213> ORGANISM: Artificial Sequence
<220> FEATURE:
<223> OTHER INFORMATION: CCTF

<400> SEQUENCE: 113
cctggacagg cctgagacgc gaagc                                          25

<210> SEQ ID NO 114
<211> LENGTH: 23
<212> TYPE: DNA
<213> ORGANISM: Artificial Sequence
<220> FEATURE:
<223> OTHER INFORMATION: CCTF

<400> SEQUENCE: 114
cctggagctc gcagagctaa cag                                            23

<210> SEQ ID NO 115
<211> LENGTH: 51
<212> TYPE: DNA
<213> ORGANISM: Artificial Sequence
<220> FEATURE:
<223> OTHER INFORMATION: primer

<400> SEQUENCE: 115
ctctgatagc gactgctcgc accaggataa tataagggt cggtggaccg g              51

<210> SEQ ID NO 116
<211> LENGTH: 25
<212> TYPE: DNA
<213> ORGANISM: Artificial Sequence
<220> FEATURE:
<223> OTHER INFORMATION: primer
```

<400> SEQUENCE: 116
ctccatgcat gattacagct gggtt                                              25

<210> SEQ ID NO 117
<211> LENGTH: 49
<212> TYPE: DNA
<213> ORGANISM: Artificial Sequence
<220> FEATURE:
<223> OTHER INFORMATION: primer

<400> SEQUENCE: 117
atcggtctcc tgaaagctgc gccaggcaga aggtacagac ggggagggc                    49

<210> SEQ ID NO 118
<211> LENGTH: 22
<212> TYPE: DNA
<213> ORGANISM: Artificial Sequence
<220> FEATURE:
<223> OTHER INFORMATION: primer

<400> SEQUENCE: 118
cacctccagc cgctccccta at                                                 22

<210> SEQ ID NO 119
<211> LENGTH: 51
<212> TYPE: DNA
<213> ORGANISM: Artificial Sequence
<220> FEATURE:
<223> OTHER INFORMATION: primer

<400> SEQUENCE: 119
ctggcgtaga gcacttacgc tccaggcaac gataaccgac caccacaagc a                 51

<210> SEQ ID NO 120
<211> LENGTH: 23
<212> TYPE: DNA
<213> ORGANISM: Artificial Sequence
<220> FEATURE:
<223> OTHER INFORMATION: primer

<400> SEQUENCE: 120
cggggtctgc acagaacagc ttt                                                23

<210> SEQ ID NO 121
<211> LENGTH: 51
<212> TYPE: DNA
<213> ORGANISM: Artificial Sequence
<220> FEATURE:
<223> OTHER INFORMATION: primer

<400> SEQUENCE: 121
ctggcgtaga gcacttacgc tccaggagga cccagctgaa cgaccttaca a                 51

<210> SEQ ID NO 122
<211> LENGTH: 25
<212> TYPE: DNA
<213> ORGANISM: Artificial Sequence
<220> FEATURE:
<223> OTHER INFORMATION: primer

<400> SEQUENCE: 122
ctgtccaccg tccaccgatg ttatg                                              25

```
<210> SEQ ID NO 123
<211> LENGTH: 48
<212> TYPE: DNA
<213> ORGANISM: Artificial Sequence
<220> FEATURE:
<223> OTHER INFORMATION: primer

<400> SEQUENCE: 123
ctggcgtaga gcacttacgc tccagggctg gcaacgtaca cgacaacg                         48

<210> SEQ ID NO 124
<211> LENGTH: 22
<212> TYPE: DNA
<213> ORGANISM: Artificial Sequence
<220> FEATURE:
<223> OTHER INFORMATION: primer

<400> SEQUENCE: 124
gctgtacaac gcgaagggtg tc                                                     22

<210> SEQ ID NO 125
<211> LENGTH: 51
<212> TYPE: DNA
<213> ORGANISM: Artificial Sequence
<220> FEATURE:
<223> OTHER INFORMATION: primer

<400> SEQUENCE: 125
ctggcgtaga gcacttacgc tccaggtcca cctatgcacc gaaacctcca a                     51

<210> SEQ ID NO 126
<211> LENGTH: 25
<212> TYPE: DNA
<213> ORGANISM: Artificial Sequence
<220> FEATURE:
<223> OTHER INFORMATION: primer

<400> SEQUENCE: 126
tgcagtgacg agtccccgtg tagta                                                  25

<210> SEQ ID NO 127
<211> LENGTH: 49
<212> TYPE: DNA
<213> ORGANISM: Artificial Sequence
<220> FEATURE:
<223> OTHER INFORMATION: primer

<400> SEQUENCE: 127
ctggcgtaga gcacttacgc tccagggact gtacaccgta tgcagcgtg                        49

<210> SEQ ID NO 128
<211> LENGTH: 21
<212> TYPE: DNA
<213> ORGANISM: Artificial Sequence
<220> FEATURE:
<223> OTHER INFORMATION: primer

<400> SEQUENCE: 128
gcgtatcagc agctcatgta a                                                      21

<210> SEQ ID NO 129
<211> LENGTH: 49
<212> TYPE: DNA
<213> ORGANISM: Artificial Sequence
<220> FEATURE:
<223> OTHER INFORMATION: primer
```

<400> SEQUENCE: 129
ctggcgtaga gcacttacgc tccaggacaa actcgacgtc gtctcggaa					49

<210> SEQ ID NO 130
<211> LENGTH: 25
<212> TYPE: DNA
<213> ORGANISM: Artificial Sequence
<220> FEATURE:
<223> OTHER INFORMATION: primer

<400> SEQUENCE: 130
caggtcacca caacaaaggc tccgt					25

<210> SEQ ID NO 131
<211> LENGTH: 49
<212> TYPE: DNA
<213> ORGANISM: Artificial Sequence
<220> FEATURE:
<223> OTHER INFORMATION: primer

<400> SEQUENCE: 131
atcaggacgc agccggttct ccaggccaag gacaggtacg gctgtcatc					49

<210> SEQ ID NO 132
<211> LENGTH: 24
<212> TYPE: DNA
<213> ORGANISM: Artificial Sequence
<220> FEATURE:
<223> OTHER INFORMATION: primer

<400> SEQUENCE: 132
ggtgcccttg aggttgtcca ggtg					24

<210> SEQ ID NO 133
<211> LENGTH: 45
<212> TYPE: DNA
<213> ORGANISM: Artificial Sequence
<220> FEATURE:
<223> OTHER INFORMATION: SCO

<400> SEQUENCE: 133
gagacgttta agtccgcgac cgctctctga tagcgactgc tcgca					45

<210> SEQ ID NO 134
<211> LENGTH: 45
<212> TYPE: DNA
<213> ORGANISM: Artificial Sequence
<220> FEATURE:
<223> OTHER INFORMATION: SCO

<400> SEQUENCE: 134
caggcgacgt ccatatggtg cgctatcggt ctcctgaaag ctgcg					45

<210> SEQ ID NO 135
<211> LENGTH: 39
<212> TYPE: DNA
<213> ORGANISM: Artificial Sequence
<220> FEATURE:
<223> OTHER INFORMATION: SCO

<400> SEQUENCE: 135
cccttaggta acgtctggct ggcgtagagc acttacgct					39

<210> SEQ ID NO 136
<211> LENGTH: 38
<212> TYPE: DNA
<213> ORGANISM: Artificial Sequence
<220> FEATURE:
<223> OTHER INFORMATION: SCO

<400> SEQUENCE: 136
aaactttaat tattgtatat caggacgcag ccggttct                             38

<210> SEQ ID NO 137
<211> LENGTH: 118
<212> TYPE: DNA
<213> ORGANISM: Artificial Sequence
<220> FEATURE:
<223> OTHER INFORMATION: product

<400> SEQUENCE: 137
ctctgatagc gactgctcgc accaggataa tataaggggt cggtggaccg gtcgatgtat      60
gtcttgttgc agatcatcaa gaacacgtag agaaacccag ctgtaatcat gcatggag      118

<210> SEQ ID NO 138
<211> LENGTH: 236
<212> TYPE: DNA
<213> ORGANISM: Artificial Sequence
<220> FEATURE:
<223> OTHER INFORMATION: product

<400> SEQUENCE: 138
atcggtctcc tgaaagctgc gccaggcacg acaggaacga ctccaacgac gcagagaaac      60
acaagtataa tattaagtat gcatggacct aaggcaacat tgcaagacat tgtattgcat    120
ttagagcccc aaaatgaaat tccggttgac cttctatgtc acgagcaatt aagcgactca    180
gaggaagaaa acgatgaaat agatggagtt aatcatcaac atttaccagc ccgacg        236

<210> SEQ ID NO 139
<211> LENGTH: 352
<212> TYPE: DNA
<213> ORGANISM: Artificial Sequence
<220> FEATURE:
<223> OTHER INFORMATION: product

<400> SEQUENCE: 139
ctggcgtaga gcacttacgc tccaggacgc catgagagga cacaagccaa cgttaaagga      60
atatgtttta gatttatatc ctgaaccaac tgacctatac tgctatgagc aattaagtga    120
cagctcagat gaggatgaag gcttggaccg gccagatgga caagcacaac cagccacagc    180
tgattactac attgtaacct gttgtcacac ttgtaacacc acagttcgtt tatgtgtcaa    240
cagtacagca agtgacctac gaaccataca gcaactactt atgggcacag tgaatattgt    300
gtgccctacc tgtgcacaac aataaacatc atctacaatg ccgatcctg aa             352

<210> SEQ ID NO 140
<211> LENGTH: 419
<212> TYPE: DNA
<213> ORGANISM: Artificial Sequence
<220> FEATURE:
<223> OTHER INFORMATION: product

<400> SEQUENCE: 140
ctggcgtaga gcacttacgc tccaggagga cccagctgaa cgaccttaca aactgcatga      60
tttgtgcaac gaggtagaag aaagcatcca tgaaatttgt ttgaattgtg tatactgcaa    120

```
acaagaatta cagcggagtg aggtatatga ctttgcatgc tatgatttgt gtatagtata    180
tagagaaggc cagccatatg gagtatgcat gaaatgttta aaattttatt caaaaataag    240
tgaatataga tggtatagat atagtgtgta tggagaaacg ttagaaaaac aatgcaacaa    300
acagttatgt catttattaa ttaggtgtat tacatgtcaa aaaccgctgt gtccagttga    360
aaagcaaaga catttagaag aaaaaaaacg attccataac atcggtggac ggtggacag     419

<210> SEQ ID NO 141
<211> LENGTH: 327
<212> TYPE: DNA
<213> ORGANISM: Artificial Sequence
<220> FEATURE:
<223> OTHER INFORMATION: product

<400> SEQUENCE: 141
ctggcgtaga gcacttacgc tccagggctg gcaacgtaca cgacaacgta acgaaaccca     60
agtgtaataa agccatgcgt ggtaatgtac cacaattaaa agatgtagta ttgcatttaa    120
caccacagac tgaaattgac ttgcaatgct acgagcaatt tgacagctca gaggaggagg    180
atgaagtaga taatatgcgt gaccagctac cagaaagacg ggctggacag gctacgtgtt    240
acagaattga agctccgtgt tgcaggtgtt caagtgtagt acaactggca gtggaaagca    300
gtggagacac ccttcgcgtt gtacagc                                        327

<210> SEQ ID NO 142
<211> LENGTH: 211
<212> TYPE: DNA
<213> ORGANISM: Artificial Sequence
<220> FEATURE:
<223> OTHER INFORMATION: product

<400> SEQUENCE: 142
ctggcgtaga gcacttacgc tccaggtcca cctatgcacc gaaacctcca agacctccgc     60
attgtccgtg ggtgccaaag acacacacct acaaccacca cagaaacgac gacgaccaga    120
cgtcacagac tccagaaaca ccaagtaccc caacaacctt tgcggggac aacaatccgt    180 ggacagtact acacggggac tcgtcactgc a                                   211

<210> SEQ ID NO 143
<211> LENGTH: 167
<212> TYPE: DNA
<213> ORGANISM: Artificial Sequence
<220> FEATURE:
<223> OTHER INFORMATION: product

<400> SEQUENCE: 143
ctggcgtaga gcacttacgc tccagggtta agaccgaaaa cggtgcatat aaaggtagtt     60
agaaagaaaa gggcaacggc atggcacgct ttgaggatcc tacacaacga ccatacaaac    120
tgcctgactt gagcacaaca ttgaatattc ctctgcatga tattcgc                  167

<210> SEQ ID NO 144
<211> LENGTH: 179
<212> TYPE: DNA
<213> ORGANISM: Artificial Sequence
<220> FEATURE:
<223> OTHER INFORMATION: product
```

```
<400> SEQUENCE: 144
ctggcgtaga gcacttacgc tccaggatgg cgctatttca caaccctgag gaacggccat      60
acaaattgcc agacctgtgc aggacattgg acactacatt gcatgacgtt acaatagagt     120
gtgtctattg cagaaggcaa ctacaacgga cagaggtata tgaatttgcc tttagtgac      179

<210> SEQ ID NO 145
<211> LENGTH: 277
<212> TYPE: DNA
<213> ORGANISM: Artificial Sequence
<220> FEATURE:
<223> OTHER INFORMATION: product

<400> SEQUENCE: 145
gctcatatgc ggcgccattt accagggcag gttgctatca aggttacaag acaggtttaa      60
ggagaccaat agaaactggg catgtggaga cagagaagac tcttgggttt ctgataggca     120
ctgactctct ctgcctattg gtctattttc ccacccttag gctgctggtg gtctacccct     180
ggacccagag gttctttgag tcctttgggg atctgtccac tcctgatgct gttatgggca    240
accctaaggt gaaggctcat ggcaagaaag tgctcgg                              277

<210> SEQ ID NO 146
<211> LENGTH: 21
<212> TYPE: DNA
<213> ORGANISM: Artificial Sequence
<220> FEATURE:
<223> OTHER INFORMATION: CCTF

<400> SEQUENCE: 146
tgcgagcagt cgctatcaga g                                               21

<210> SEQ ID NO 147
<211> LENGTH: 21
<212> TYPE: DNA
<213> ORGANISM: Artificial Sequence
<220> FEATURE:
<223> OTHER INFORMATION: CCTF

<400> SEQUENCE: 147
cgcagctttc aggagaccga t                                               21

<210> SEQ ID NO 148
<211> LENGTH: 21
<212> TYPE: DNA
<213> ORGANISM: Artificial Sequence
<220> FEATURE:
<223> OTHER INFORMATION: CCTF

<400> SEQUENCE: 148
agcgtaagtg ctctacgcca g                                               21

<210> SEQ ID NO 149
<211> LENGTH: 20
<212> TYPE: DNA
<213> ORGANISM: Artificial Sequence
<220> FEATURE:
<223> OTHER INFORMATION: CCTF

<400> SEQUENCE: 149
agaaccggct gcgtcctgat                                                 20
```

```
<210> SEQ ID NO 150
<211> LENGTH: 26
<212> TYPE: DNA
<213> ORGANISM: Artificial Sequence
<220> FEATURE:
<223> OTHER INFORMATION: primer

<400> SEQUENCE: 150
ttgctatggc tgacggggaa gaatgg                                          26

<210> SEQ ID NO 151
<211> LENGTH: 56
<212> TYPE: DNA
<213> ORGANISM: Artificial Sequence
<220> FEATURE:
<223> OTHER INFORMATION: primer

<400> SEQUENCE: 151
gccccgttga gagcacgaat ccagggggt gaatcttctg cttaatgtga agacac         56

<210> SEQ ID NO 152
<211> LENGTH: 26
<212> TYPE: DNA
<213> ORGANISM: Artificial Sequence
<220> FEATURE:
<223> OTHER INFORMATION: primer

<400> SEQUENCE: 152
gggcaccatg cagtaccaaa cggaac                                          26

<210> SEQ ID NO 153
<211> LENGTH: 52
<212> TYPE: DNA
<213> ORGANISM: Artificial Sequence
<220> FEATURE:
<223> OTHER INFORMATION: primer

<400> SEQUENCE: 153
ccgtggcgcg aacttatcga ccaggatcac actgagggtc tcccaataga gc             52

<210> SEQ ID NO 154
<211> LENGTH: 29
<212> TYPE: DNA
<213> ORGANISM: Artificial Sequence
<220> FEATURE:
<223> OTHER INFORMATION: primer

<400> SEQUENCE: 154
tcaaagacta agtggtgcca tggatgaac                                       29

<210> SEQ ID NO 155
<211> LENGTH: 50
<212> TYPE: DNA
<213> ORGANISM: Artificial Sequence
<220> FEATURE:
<223> OTHER INFORMATION: primer

<400> SEQUENCE: 155
aagtgacctg ccattgcgcg ccaggtatgt ctacagcaga gggacccagc                50

<210> SEQ ID NO 156
<211> LENGTH: 49
<212> TYPE: DNA
<213> ORGANISM: Artificial Sequence
<220> FEATURE:
<223> OTHER INFORMATION: primer
```

<400> SEQUENCE: 156
ggcttagagc accgcgtcat tccaggtgtc gctactggaa gcggtgatc                49

<210> SEQ ID NO 157
<211> LENGTH: 24
<212> TYPE: DNA
<213> ORGANISM: Artificial Sequence
<220> FEATURE:
<223> OTHER INFORMATION: primer

<400> SEQUENCE: 157
gcgatagcta aggtacgacg ggtc                                           24

<210> SEQ ID NO 158
<211> LENGTH: 29
<212> TYPE: DNA
<213> ORGANISM: Artificial Sequence
<220> FEATURE:
<223> OTHER INFORMATION: primer

<400> SEQUENCE: 158
gtagattcga tccatgctcc tctactacc                                      29

<210> SEQ ID NO 159
<211> LENGTH: 55
<212> TYPE: DNA
<213> ORGANISM: Artificial Sequence
<220> FEATURE:
<223> OTHER INFORMATION: primer

<400> SEQUENCE: 159
cgtcttacat gcgcaagcgg ccaggtgata ttgagttcgg taatgcaaga tctgc         55

<210> SEQ ID NO 160
<211> LENGTH: 27
<212> TYPE: DNA
<213> ORGANISM: Artificial Sequence
<220> FEATURE:
<223> OTHER INFORMATION: primer

<400> SEQUENCE: 160
ccatagagat ggcaatagat gaagagc                                        27

<210> SEQ ID NO 161
<211> LENGTH: 52
<212> TYPE: DNA
<213> ORGANISM: Artificial Sequence
<220> FEATURE:
<223> OTHER INFORMATION: primer

<400> SEQUENCE: 161
aggcgttccg cttcaacgag ccaggttgtc agattctgta gcttgctcag tc            52

<210> SEQ ID NO 162
<211> LENGTH: 29
<212> TYPE: DNA
<213> ORGANISM: Artificial Sequence
<220> FEATURE:
<223> OTHER INFORMATION: primer

<400> SEQUENCE: 162
ggtggtgatc ccaacttgtt atatcgaag                                      29

```
<210> SEQ ID NO 163
<211> LENGTH: 56
<212> TYPE: DNA
<213> ORGANISM: Artificial Sequence
<220> FEATURE:
<223> OTHER INFORMATION: primer

<400> SEQUENCE: 163
tccgtctgcg aagatctgag cccaggttca atctatcrtc tgacagatct tgaagt       56

<210> SEQ ID NO 164
<211> LENGTH: 54
<212> TYPE: DNA
<213> ORGANISM: Artificial Sequence
<220> FEATURE:
<223> OTHER INFORMATION: primer

<400> SEQUENCE: 164
gtgtcacgac gcgcgaatct ccaggagatc gtgaccagta taatagctca acac         54

<210> SEQ ID NO 165
<211> LENGTH: 28
<212> TYPE: DNA
<213> ORGANISM: Artificial Sequence
<220> FEATURE:
<223> OTHER INFORMATION: primer

<400> SEQUENCE: 165
tttcagacaa tgcagggata acaccagc                                      28

<210> SEQ ID NO 166
<211> LENGTH: 50
<212> TYPE: DNA
<213> ORGANISM: Artificial Sequence
<220> FEATURE:
<223> OTHER INFORMATION: primer

<400> SEQUENCE: 166
cccagaacga tttgcggcgt ccaggcttgg tcctctctta ggaggcaagc               50

<210> SEQ ID NO 167
<211> LENGTH: 22
<212> TYPE: DNA
<213> ORGANISM: Artificial Sequence
<220> FEATURE:
<223> OTHER INFORMATION: primer

<400> SEQUENCE: 167
aggatgcttc ggagtacctg ag                                            22

<210> SEQ ID NO 168
<211> LENGTH: 45
<212> TYPE: DNA
<213> ORGANISM: Artificial Sequence
<220> FEATURE:
<223> OTHER INFORMATION: primer

<400> SEQUENCE: 168
tgcattgccg tcgcagagac ccaggcaacg ggcacgaagc gcatc                   45

<210> SEQ ID NO 169
<211> LENGTH: 28
<212> TYPE: DNA
<213> ORGANISM: Artificial Sequence
<220> FEATURE:
<223> OTHER INFORMATION: primer
```

<400> SEQUENCE: 169
gccctaatga taagacaggc agttgtgg					28

<210> SEQ ID NO 170
<211> LENGTH: 52
<212> TYPE: DNA
<213> ORGANISM: Artificial Sequence
<220> FEATURE:
<223> OTHER INFORMATION: primer

<400> SEQUENCE: 170
atgcgcttgg attgccgatg ccaggagccc tgttagttct ggatgctgaa ca					52

<210> SEQ ID NO 171
<211> LENGTH: 35
<212> TYPE: DNA
<213> ORGANISM: Artificial Sequence
<220> FEATURE:
<223> OTHER INFORMATION: SCO

<400> SEQUENCE: 171
cttatagatt atattgcccc gttgagagca cgaat					35

<210> SEQ ID NO 172
<211> LENGTH: 42
<212> TYPE: DNA
<213> ORGANISM: Artificial Sequence
<220> FEATURE:
<223> OTHER INFORMATION: SCO

<400> SEQUENCE: 172
ctaagtaagc ctatatcgaa ttccgtggcg cgaacttatc ga					42

<210> SEQ ID NO 173
<211> LENGTH: 42
<212> TYPE: DNA
<213> ORGANISM: Artificial Sequence
<220> FEATURE:
<223> OTHER INFORMATION: SCO

<400> SEQUENCE: 173
cgtactgcac tcgcctacga ctaagtgacc tgccattgcg cg					42

<210> SEQ ID NO 174
<211> LENGTH: 35
<212> TYPE: DNA
<213> ORGANISM: Artificial Sequence
<220> FEATURE:
<223> OTHER INFORMATION: SCO

<400> SEQUENCE: 174
cttataagtt acatggctta gagcaccgcg tcatt					35

<210> SEQ ID NO 175
<211> LENGTH: 34
<212> TYPE: DNA
<213> ORGANISM: Artificial Sequence
<220> FEATURE:
<223> OTHER INFORMATION: SCO

<400> SEQUENCE: 175
ctaattgtaa tactcgtctt acatgcgcaa gcgg					34

<210> SEQ ID NO 176
<211> LENGTH: 42
<212> TYPE: DNA
<213> ORGANISM: Artificial Sequence
<220> FEATURE:
<223> OTHER INFORMATION: SCO

<400> SEQUENCE: 176
ctaatcgtat gagatctatg ataggcgttc cgcttcaacg ag                         42

<210> SEQ ID NO 177
<211> LENGTH: 35
<212> TYPE: DNA
<213> ORGANISM: Artificial Sequence
<220> FEATURE:
<223> OTHER INFORMATION: SCO

<400> SEQUENCE: 177
tcatagacat ttattccgtc tgcgaagatc tgagc                                 35

<210> SEQ ID NO 178
<211> LENGTH: 42
<212> TYPE: DNA
<213> ORGANISM: Artificial Sequence
<220> FEATURE:
<223> OTHER INFORMATION: SCO

<400> SEQUENCE: 178
tacgaatctg acctagtaag atgtgtcacg acgcgcgaat ct                         42

<210> SEQ ID NO 179
<211> LENGTH: 42
<212> TYPE: DNA
<213> ORGANISM: Artificial Sequence
<220> FEATURE:
<223> OTHER INFORMATION: SCO

<400> SEQUENCE: 179
tgccactaac aggccgctag atcccagaac gatttgcggc gt                         42

<210> SEQ ID NO 180
<211> LENGTH: 41
<212> TYPE: DNA
<213> ORGANISM: Artificial Sequence
<220> FEATURE:
<223> OTHER INFORMATION: SCO

<400> SEQUENCE: 180
tcgagcgtgc gccagatcca ttgcattgcc gtcgcagaga c                          41

<210> SEQ ID NO 181
<211> LENGTH: 42
<212> TYPE: DNA
<213> ORGANISM: Artificial Sequence
<220> FEATURE:
<223> OTHER INFORMATION: SCO

<400> SEQUENCE: 181
tcgactgtgc ctgcgtccgt atatgcgctt ggattgccga tg                         42

<210> SEQ ID NO 182
<211> LENGTH: 219
<212> TYPE: DNA
<213> ORGANISM: Artificial Sequence
<220> FEATURE:
<223> OTHER INFORMATION: product

```
<400> SEQUENCE: 182
ttgctatggc tgacggggaa gaatggtttg tacccaaacc tgagcatgtc ctatgtaaac      60
aacaaagaga aagaagtcct tgtgctatgg ggtgttcatc acccacctaa catagggaac    120
caaagggccc tctaccatac agaaaatgct tatgtctctg tagtgtcttc acattatagc    180
agaagattca ccccctgga ttcgtgctct caacggggc                            219

<210> SEQ ID NO 183
<211> LENGTH: 211
<212> TYPE: DNA
<213> ORGANISM: Artificial Sequence
<220> FEATURE:
<223> OTHER INFORMATION: product

<400> SEQUENCE: 183
gggcaccatg cagtaccaaa cggaacgata gtgaaaacaa tcacaaatga ccaaattgaa      60
gttactaatg ctactgagtt ggttcagaat tcctcaatag gtgaaatatg cgacagtcct    120
catcagatcc ttgatggaga gaactgcaca ctaatagatg ctctattggg agaccctcag    180
tgtgatcctg gtcgataagt tcgcgccacg g                                   211

<210> SEQ ID NO 184
<211> LENGTH: 236
<212> TYPE: DNA
<213> ORGANISM: Artificial Sequence
<220> FEATURE:
<223> OTHER INFORMATION: product

<400> SEQUENCE: 184
tcaaagacta agtggtgcca tggatgaact ccacaacgaa atactcgagc tggatgaaaa      60
agtggatgac ctcagagctg acactataag ctcacaaata gaacttgcag tcttgctttc    120
caacgaagga ataataaaca gtgaagatga gcatctattg gcacttgaga gaaaactaaa    180
gaaaatgctg ggtccctctg ctgtagacat acctggcgcg caatggcagg tcactt        236

<210> SEQ ID NO 185
<211> LENGTH: 161
<212> TYPE: DNA
<213> ORGANISM: Artificial Sequence
<220> FEATURE:
<223> OTHER INFORMATION: product

<400> SEQUENCE: 185
ggcttagagc accgcgtcat tccaggtgtc gctactggaa gcggtgatcc gcacagtgac      60
gactttacag caattgctta cttaagggac gaattgctcg caaagcatcc gaccttaggt    120
tctggtaatg acgaggcgac ccgtcgtacc ttagctatcg c                        161

<210> SEQ ID NO 186
<211> LENGTH: 244
<212> TYPE: DNA
<213> ORGANISM: Artificial Sequence
<220> FEATURE:
<223> OTHER INFORMATION: product

<400> SEQUENCE: 186
gtagattcga tccatgctcc tctactacca tggtccagcc gactgagaca agggatgata      60
tataatgcca ataaagtagc tctggcaccc caatgtctcc cagtcgacaa agatatcaga    120
ttcagagttg tatttgtcaa cggaacatca ctgggtacaa tcacaattgc caaggtccca    180
```

```
aaaactcttg cagatcttgc attaccgaac tcaatatcac ctggccgctt gcgcatgtaa    240
gacg                                                                 244
```

<210> SEQ ID NO 187
<211> LENGTH: 179
<212> TYPE: DNA
<213> ORGANISM: Artificial Sequence
<220> FEATURE:
<223> OTHER INFORMATION: product

<400> SEQUENCE: 187

```
ccatagagat ggcaatagat gaagagccag aacaattcga acatagagca gaccaagaac     60
aagatgggga acctcaatca tctataatcc aatatgcttg ggcagaagga aacagaagcg    120
atgaccggac tgagcaagct acagaatctg acaacctggc tcgttgaagc ggaacgcct    179
```

<210> SEQ ID NO 188
<211> LENGTH: 178
<212> TYPE: DNA
<213> ORGANISM: Artificial Sequence
<220> FEATURE:
<223> OTHER INFORMATION: product

<400> SEQUENCE: 188

```
ggtggtgatc ccaacttgtt atatcgaagt ttctatagaa gaactcctga tttcctcaca     60
gaggctatag ttcactctgt gttcatactt agttattata caaaccatga tttaaaggat    120
aaacttcaag atctgtcaga ygatagattg aacctgggct cagatcttcg cagacgga     178
```

<210> SEQ ID NO 189
<211> LENGTH: 138
<212> TYPE: DNA
<213> ORGANISM: Artificial Sequence
<220> FEATURE:
<223> OTHER INFORMATION: product

<400> SEQUENCE: 189

```
ggtggtgatc ctaatttgtt atatcgaagc ttttataggs gaactccaga cttccttaca     60
gaagctatag tacattcagt gttcgtgttg agctattata ctggtcacga tctcctggag    120
attcgcgcgt cgtgacac                                                  138
```

<210> SEQ ID NO 190
<211> LENGTH: 328
<212> TYPE: DNA
<213> ORGANISM: Artificial Sequence
<220> FEATURE:
<223> OTHER INFORMATION: product

<400> SEQUENCE: 190

```
tttcagacaa tgcagggata acaccagcaa tatcattgga cctaatgact gatgctgaac     60
tggccagagc tgtatcatac atgccaacat ctgcagggca gataaagctg atgttggaga    120
accgcgcaat ggtaaggaga aaaggatttg gaatcctaat aggggtctac ggaagctctg    180
tgatttacat ggttcaattg ccgatctttg tgtcataga tacaccttgt tggataatca    240
aggcagctcc ctcttgctca gaaaaaaacg ggaattatgc ttgcctccta agagaggacc    300
aagcctggac gccgcaaatc gttctggg                                       328
```

<210> SEQ ID NO 191
<211> LENGTH: 187
<212> TYPE: DNA
<213> ORGANISM: Artificial Sequence

```
<220> FEATURE:
<223> OTHER INFORMATION: product

<400> SEQUENCE: 191
aggatgcttc ggagtacctg agtccgggtc tggtgcagtt cgcccgtgca acagacacct      60
acttcagtat ggggaacaag tttagaaacc ccacagtggc gcccaccac gatgtgacca      120 ccgaccgtag ccagcgactg atgctgcgct tcgtgcccgt tgcctgggtc tctgcgacgg     180
caatgca                                                                187

<210> SEQ ID NO 192
<211> LENGTH: 290
<212> TYPE: DNA
<213> ORGANISM: Artificial Sequence
<220> FEATURE:
<223> OTHER INFORMATION: product

<400> SEQUENCE: 192
gccctaatga taagacaggc agttgtggtc cagtatcgtc taatggagca aatggagtaa     60 aaggatttc attcaaatac ggcaatggtg tttggatagg gagaactaaa agcattagtt      120
caagaaaagg ttttgagatg atttgggatc cgaatggatg gactgggact gacaataaat     180
tctcaataaa gcaagatatc gtaggaataa atgagtggtc agggtatagc gggagttttg     240
ttcagcatcc agaactaaca gggctcctgg catcggcaat ccaagcgcat                290

<210> SEQ ID NO 193
<211> LENGTH: 20
<212> TYPE: DNA
<213> ORGANISM: Artificial Sequence
<220> FEATURE:
<223> OTHER INFORMATION: CCTF

<400> SEQUENCE: 193
attcgtgctc tcaacggggc                                                  20

<210> SEQ ID NO 194
<211> LENGTH: 20
<212> TYPE: DNA
<213> ORGANISM: Artificial Sequence
<220> FEATURE:
<223> OTHER INFORMATION: CCTF

<400> SEQUENCE: 194
tcgataagtt cgcgccacgg                                                  20

<210> SEQ ID NO 195
<211> LENGTH: 20
<212> TYPE: DNA
<213> ORGANISM: Artificial Sequence
<220> FEATURE:
<223> OTHER INFORMATION: CCTF

<400> SEQUENCE: 195
cgcgcaatgg caggtcactt                                                  20

<210> SEQ ID NO 196
<211> LENGTH: 21
<212> TYPE: DNA
<213> ORGANISM: Artificial Sequence
<220> FEATURE:
<223> OTHER INFORMATION: CCTF
```

```
<400> SEQUENCE: 196
aatgacgcgg tgctctaagc c                                              21

<210> SEQ ID NO 197
<211> LENGTH: 20
<212> TYPE: DNA
<213> ORGANISM: Artificial Sequence
<220> FEATURE:
<223> OTHER INFORMATION: CCTF

<400> SEQUENCE: 197
ccgcttgcgc atgtaagacg                                                20

<210> SEQ ID NO 198
<211> LENGTH: 20
<212> TYPE: DNA
<213> ORGANISM: Artificial Sequence
<220> FEATURE:
<223> OTHER INFORMATION: CCTF

<400> SEQUENCE: 198
ctcgttgaag cggaacgcct                                                20

<210> SEQ ID NO 199
<211> LENGTH: 21
<212> TYPE: DNA
<213> ORGANISM: Artificial Sequence
<220> FEATURE:
<223> OTHER INFORMATION: CCTF

<400> SEQUENCE: 199
gctcagatct tcgcagacgg a                                              21

<210> SEQ ID NO 200
<211> LENGTH: 20
<212> TYPE: DNA
<213> ORGANISM: Artificial Sequence
<220> FEATURE:
<223> OTHER INFORMATION: CCTF

<400> SEQUENCE: 200
agattcgcgc gtcgtgacac                                                20

<210> SEQ ID NO 201
<211> LENGTH: 20
<212> TYPE: DNA
<213> ORGANISM: Artificial Sequence
<220> FEATURE:
<223> OTHER INFORMATION: CCTF

<400> SEQUENCE: 201
acgccgcaaa tcgttctggg                                                20

<210> SEQ ID NO 202
<211> LENGTH: 20
<212> TYPE: DNA
<213> ORGANISM: Artificial Sequence
<220> FEATURE:
<223> OTHER INFORMATION: CCTF

<400> SEQUENCE: 202
gtctctgcga cggcaatgca                                                20
```

```
<210> SEQ ID NO 203
<211> LENGTH: 20
<212> TYPE: DNA
<213> ORGANISM: Artificial Sequence
<220> FEATURE:
<223> OTHER INFORMATION: CCTF

<400> SEQUENCE: 203
catcggcaat ccaagcgcat                                              20

<210> SEQ ID NO 204
<211> LENGTH: 57
<212> TYPE: DNA
<213> ORGANISM: Artificial Sequence
<220> FEATURE:
<223> OTHER INFORMATION: primer

<400> SEQUENCE: 204
acgaggcctg tccgcttact agccaggctg gtcctcatcc aacagctctt ctatcgc     57

<210> SEQ ID NO 205
<211> LENGTH: 59
<212> TYPE: DNA
<213> ORGANISM: Artificial Sequence
<220> FEATURE:
<223> OTHER INFORMATION: primer

<400> SEQUENCE: 205
ccgggtacgc taagtccgct atccaggttc tggtcctcat ccaacagctc ttctatcgt   59

<210> SEQ ID NO 206
<211> LENGTH: 27
<212> TYPE: DNA
<213> ORGANISM: Artificial Sequence
<220> FEATURE:
<223> OTHER INFORMATION: primer

<400> SEQUENCE: 206
gacccatggg actctggaga gcgtgaa                                      27

<210> SEQ ID NO 207
<211> LENGTH: 54
<212> TYPE: DNA
<213> ORGANISM: Artificial Sequence
<220> FEATURE:
<223> OTHER INFORMATION: primer

<400> SEQUENCE: 207
gctcatatgc ggcgccattt accagggcag gttgctatca aggttacaag acag        54

<210> SEQ ID NO 208
<211> LENGTH: 24
<212> TYPE: DNA
<213> ORGANISM: Artificial Sequence
<220> FEATURE:
<223> OTHER INFORMATION: primer

<400> SEQUENCE: 208
ccgagcactt tcttgccatg agcc                                         24

<210> SEQ ID NO 209
<211> LENGTH: 44
<212> TYPE: DNA
<213> ORGANISM: Artificial Sequence
<220> FEATURE:
<223> OTHER INFORMATION: SCO
```

<400> SEQUENCE: 209
gtagcacgct tcgaatggct atacgaggcc tgtccgctta ctag        44

<210> SEQ ID NO 210
<211> LENGTH: 45
<212> TYPE: DNA
<213> ORGANISM: Artificial Sequence
<220> FEATURE:
<223> OTHER INFORMATION: SCO

<400> SEQUENCE: 210
gatacggagg tccgaaggca gtgttggtta ccctaacgcg ccgga        45

<210> SEQ ID NO 211
<211> LENGTH: 45
<212> TYPE: DNA
<213> ORGANISM: Artificial Sequence
<220> FEATURE:
<223> OTHER INFORMATION: SCO

<400> SEQUENCE: 211
attagtttaa ctattatatt ttatgctcat atgcggcgcc attta        45

<210> SEQ ID NO 212
<211> LENGTH: 139
<212> TYPE: DNA
<213> ORGANISM: Artificial Sequence
<220> FEATURE:
<223> OTHER INFORMATION: product

<400> SEQUENCE: 212
acgaggcctg tccgcttact agccaggctg gtcctcatcc aacagctctt ctatcacgtg        60
ttcgaaagtg tcagccaatg atgtcaagcc tcttgaacct gccttgggcc cattcacgct       120
ctccagagtc ccatgggtc                                                   139

<210> SEQ ID NO 213
<211> LENGTH: 141
<212> TYPE: DNA
<213> ORGANISM: Artificial Sequence
<220> FEATURE:
<223> OTHER INFORMATION: product

<400> SEQUENCE: 213
ccgggtacgc taagtccgct atccaggttc tggtcctcat ccaacagctc ttctatcacg        60
tgttcgaaag tgtcagccaa tgatgtcaag cctcttgaac ctgccttggg cccattcacg       120
ctctccagag tcccatgggt c                                                141

<210> SEQ ID NO 214
<211> LENGTH: 277
<212> TYPE: DNA
<213> ORGANISM: Artificial Sequence
<220> FEATURE:
<223> OTHER INFORMATION: product

<400> SEQUENCE: 214
gctcatatgc ggcgccattt accagggcag gttgctatca aggttacaag acaggtttaa        60
ggagaccaat agaaactggg catgtggaga cagagaagac tcttgggttt ctgataggca       120
ctgactctct ctgcctattg gtctattttc ccacccttag gctgctggtg gtctacccctt      180 ggacccagag gttctttgag tcctttgggg atctgtccac tcctgatgct gttatgggca       240
accctaaggt gaaggctcat ggcaagaaag tgctcgg                                277

```
<210> SEQ ID NO 215
<211> LENGTH: 22
<212> TYPE: DNA
<213> ORGANISM: Artificial Sequence
<220> FEATURE:
<223> OTHER INFORMATION: CCTF

<400> SEQUENCE: 215
ctagtaagcg gacaggcctc gt                                               22

<210> SEQ ID NO 216
<211> LENGTH: 22
<212> TYPE: DNA
<213> ORGANISM: Artificial Sequence
<220> FEATURE:
<223> OTHER INFORMATION: CCTF

<400> SEQUENCE: 216
atagcggact tagcgtaccc gg                                               22

<210> SEQ ID NO 217
<211> LENGTH: 20
<212> TYPE: DNA
<213> ORGANISM: Artificial Sequence
<220> FEATURE:
<223> OTHER INFORMATION: CCTF

<400> SEQUENCE: 217
taaatggcgc cgcatatgag                                                  20

<210> SEQ ID NO 218
<211> LENGTH: 48
<212> TYPE: DNA
<213> ORGANISM: Artificial Sequence
<220> FEATURE:
<223> OTHER INFORMATION: primer

<400> SEQUENCE: 218
ctcatcgcca cgagccggtt aaccaggttg aaacaccgcc cggaaccc                   48

<210> SEQ ID NO 219
<211> LENGTH: 23
<212> TYPE: DNA
<213> ORGANISM: Artificial Sequence
<220> FEATURE:
<223> OTHER INFORMATION: primer

<400> SEQUENCE: 219
gctccttatt cggtttgacc ggt                                              23

<210> SEQ ID NO 220
<211> LENGTH: 55
<212> TYPE: DNA
<213> ORGANISM: Artificial Sequence
<220> FEATURE:
<223> OTHER INFORMATION: primer

<400> SEQUENCE: 220
gctcgcaggt acggcaccat tcaccaggca gaaggtatga taacaacggt agagc           55

<210> SEQ ID NO 221
<211> LENGTH: 21
<212> TYPE: DNA
<213> ORGANISM: Artificial Sequence
<220> FEATURE:
<223> OTHER INFORMATION: primer
```

```
<400> SEQUENCE: 221
cccctttgca ccgttgaggg g                                      21

<210> SEQ ID NO 222
<211> LENGTH: 57
<212> TYPE: DNA
<213> ORGANISM: Artificial Sequence
<220> FEATURE:
<223> OTHER INFORMATION: primer

<400> SEQUENCE: 222
agtcgattat gtctgaggcc gcgccaggtt aaagtagcat atgatcaagc tcattca    57

<210> SEQ ID NO 223
<211> LENGTH: 35
<212> TYPE: DNA
<213> ORGANISM: Artificial Sequence
<220> FEATURE:
<223> OTHER INFORMATION: primer

<400> SEQUENCE: 223
gatcctgaca tataatcatt atctcctttt ataaa                       35

<210> SEQ ID NO 224
<211> LENGTH: 23
<212> TYPE: DNA
<213> ORGANISM: Artificial Sequence
<220> FEATURE:
<223> OTHER INFORMATION: SCO

<400> SEQUENCE: 224
tctcatcgcc acgagccggt taa                                    23

<210> SEQ ID NO 225
<211> LENGTH: 23
<212> TYPE: DNA
<213> ORGANISM: Artificial Sequence
<220> FEATURE:
<223> OTHER INFORMATION: SCO

<400> SEQUENCE: 225
tgtcgcaggt acggcaccat tca                                    23

<210> SEQ ID NO 226
<211> LENGTH: 24
<212> TYPE: DNA
<213> ORGANISM: Artificial Sequence
<220> FEATURE:
<223> OTHER INFORMATION: SCO

<400> SEQUENCE: 226
tagtcgatta tgtctgaggc cgcg                                   24

<210> SEQ ID NO 227
<211> LENGTH: 112
<212> TYPE: DNA
<213> ORGANISM: Artificial Sequence
<220> FEATURE:
<223> OTHER INFORMATION: product

<400> SEQUENCE: 227
ctcatcgcca cgagccggtt aaccaggttg aaacaccgcc cggaacccga tataatccgc    60
ccttcaacat cagtgaaaat cttttttttaa ccggtcaaac cgaataagga gc          112
```

-continued

```
<210> SEQ ID NO 228
<211> LENGTH: 109
<212> TYPE: DNA
<213> ORGANISM: Artificial Sequence
<220> FEATURE:
<223> OTHER INFORMATION: product

<400> SEQUENCE: 228
gctcgcaggt acggcaccat tcaccaggca gaaggtatga taacaacggt agagctttat    60
atgatattaa cttagcaaaa atggaaaacc cctcaacggt gcaaagggg              109

<210> SEQ ID NO 229
<211> LENGTH: 115
<212> TYPE: DNA
<213> ORGANISM: Artificial Sequence
<220> FEATURE:
<223> OTHER INFORMATION: product

<400> SEQUENCE: 229
agtcgattat gtctgaggcc gcgccagggt ttctgtacac gatccaatty acaaataaca    60
tttacaattc gtaaaatttt tttataaaag gagataatga ttatatgtca ggatc        115

<210> SEQ ID NO 230
<211> LENGTH: 27
<212> TYPE: DNA
<213> ORGANISM: Artificial Sequence
<220> FEATURE:
<223> OTHER INFORMATION: SCO

<400> SEQUENCE: 230
cctggttaac cggctcgtgg cgatgag                                        27

<210> SEQ ID NO 231
<211> LENGTH: 28
<212> TYPE: DNA
<213> ORGANISM: Artificial Sequence
<220> FEATURE:
<223> OTHER INFORMATION: SCO

<400> SEQUENCE: 231
cctggtgaat ggtgccgtac ctgcgagc                                       28

<210> SEQ ID NO 232
<211> LENGTH: 28
<212> TYPE: DNA
<213> ORGANISM: Artificial Sequence
<220> FEATURE:
<223> OTHER INFORMATION: SCO

<400> SEQUENCE: 232
cctggcgcgg cctcagacat aatcgact                                       28
```